US012758627B2

(12) United States Patent
Reeves et al.

(10) Patent No.: US 12,758,627 B2
(45) Date of Patent: Oct. 13, 2026

(54) IMMUNOGENIC PEPTIDE

(71) Applicant: UCL Ventures Limited, London (GB)

(72) Inventors: Matthew Bryan Reeves, London (GB); Ilona Anna Baraniak, London (GB); Paul David Griffiths, London (GB)

(73) Assignee: UCL BUSINESS LTD, London (GB)

( * ) Notice: Subject to any disclaimer, the term of this patent is extended or adjusted under 35 U.S.C. 154(b) by 564 days.

(21) Appl. No.: 18/267,241

(22) PCT Filed: Dec. 17, 2021

(86) PCT No.: PCT/GB2021/053351
§ 371 (c)(1),
(2) Date: Jun. 14, 2023

(87) PCT Pub. No.: WO2022/129937
PCT Pub. Date: Jun. 23, 2022

(65) Prior Publication Data

US 2024/0058437 A1 Feb. 22, 2024

(30) Foreign Application Priority Data

Dec. 18, 2020 (GB) ..................................... 2020135

(51) Int. Cl.

| | |
|---|---|
| ***A61K 39/245*** | (2006.01) |
| ***A61K 45/06*** | (2006.01) |
| ***A61P 31/22*** | (2006.01) |
| ***C07K 14/045*** | (2006.01) |
| ***C07K 16/00*** | (2006.01) |
| ***C07K 16/08*** | (2026.01) |
| ***C07K 16/085*** | (2026.01) |

(52) U.S. Cl.
CPC ............ *A61K 39/245* (2013.01); *A61K 45/06* (2013.01); *A61P 31/22* (2018.01); *C07K 14/045* (2013.01); *C07K 16/089* (2023.08)

(58) Field of Classification Search
CPC .. C07K 2317/76; C07K 16/00; C07K 16/089; C12N 15/86; A61K 39/245
See application file for complete search history.

(56) References Cited

U.S. PATENT DOCUMENTS

| | | | |
|---|---|---|---|
| 4,642,333 | A | 2/1987 | Person |
| 8,153,129 | B2 | 4/2012 | Funaro et al. |
| 9,346,874 | B2 | 5/2016 | Grawunder et al. |
| 2010/0322953 | A1 | 12/2010 | Leng et al. |

FOREIGN PATENT DOCUMENTS

| | | | |
|---|---|---|---|
| CN | 101780277 | A | 7/2010 |
| EP | 2308895 | A1 | 4/2011 |
| EP | 2420572 | A1 | 2/2012 |
| WO | WO-2008084410 | A3 | 7/2008 |
| WO | WO-2011/076883 | A1 | 6/2011 |
| WO | WO-2015/089340 | A1 | 6/2015 |
| WO | WO-2018/209125 | A1 | 11/2018 |
| WO | WO-2020/191181 | A1 | 9/2020 |

OTHER PUBLICATIONS

Potzsch et al., B cell repertoire analysis identifies new antigenic domains on glycoprotein B of human cytomegalovirus which are target of neutralizing antibodies, PLOS Pathog., 7(8):e1002172 (2011).
Great Britain Application No. 2020135.6, Search Report, mailed Jun. 14, 2021.
International Application No. PCT/GB2021/053351, International Search Report and Written Opinion, mailed Mar. 30, 2022.
Pass et al., A subunit cytomegalovirus vaccine based on recombinant envelope glycoprotein B and a new adjuvant, J. Infect. Dis., 180(4):970-5).
Kabat et al., 1991, 5th Ed. Public Health Service, National Institutes of Health, Bethesda, MD, 647-669.
Groff et al., Biotechnology Advances 2015, 33(8): 1787-1798.
Dangi et al., Front Pharmacol. 2018; 9: 630.
Schub et al., J. Immunol 2009; 183:6819-6830.
Wagner et al., J. Biol. Chem. 2019; 294:5790-5804.
Stripecke et al., Blood 2016; 128: 5721.
Ali et al., J. Infectious Diseases 2020; 222: 853-862.
Griffiths et al., 2011 Lancet 377 1256-1263.
Bernstein et al. 2016, Vaccine 34(3) 313-9).
Heldwein EE et al. (2006), Science, 313: 217-220.
Backovic M et al. (2009), Proc. Natl. Acad. Sci. U.S.A, 106: 2880-2885.
Burke, HG and Heldwein, EE (2015), PLoS Pathogens, 11(10): e100530.
Baraniak et al. 2019 J. Infect. Dis. 220(2) 228-232.
Baraniak et al, Proc Natl Acad Sci U S A. 2018 115(24):6273-6278.
Lefranc et al, 2009 Nar 37:D1006-D1012.
Lefranc 2003, Leukemia 17: 260-266.
Sharma S et al., HCMV gB Shares Structural and Functional Properties With gB Proteins From Other Herpesviruses, Virology, Jan. 20, 2013, vol. 435, Issue 2, pp. 239-249.
Altschul S F et al., Basic Local Alignment Search Tool, J. Mol. Biol., 1990, vol. 215, Issue 3, pp. 403-410.
Ausubel F M et al., Short Protocols in Molecular Biology, 1999, 4th Edition, Ch. 18.
Coffin et al., "Retroviruses" 1997 Cold Spring Harbour Laboratory Press Eds: JM Coffin, SM Hughes, HE Varmus, pp. 758-763.

(Continued)

*Primary Examiner* — Barry A Chestnut
(74) *Attorney, Agent, or Firm* — MARSHALL, GERSTEIN & BORUN LLP

(57) ABSTRACT

The invention provides a human herpesvirus immunogenic peptide comprising a novel antigenic domain (AD) of glycoprotein B, termed AD-6. The invention also provides a nucleic acid sequence encoding said immunogenic peptide and an inhibitor that binds to said 5 immunogenic peptide. Also provided are an immunogenic composition, a pharmaceutical composition and a vaccine comprising said immunogenic peptide, nucleic acid sequence or inhibitor, and methods of treating or preventing a human herpesvirus infection.

11 Claims, 12 Drawing Sheets

Specification includes a Sequence Listing.

(56) References Cited

OTHER PUBLICATIONS

EMBL—EBIENA No. AAR31620.1.
EMBL—EBIENA No. AAA45774.1.
EMBL—EBIENA No. AAA46009.1.
EMBL—EBIENA No. CAA24806.1.
Tatusova T A et al., Blast 2 Sequences, A New Tool For Comparing Protein and Nucleotide Sequences, FEMS Microbiology Letters, 1999, 174: pp. 247-250.
Tatusova T A et al., Erratum to "Blast 2 Sequences, A New Tool for Comparing Protein and Nucleotide Sequences", FEMS Microbiol. Lett, 1999, 177, pp. 187-188.
Lewis et al., Human Immunodeficiency Virus Infection of Cells Arrested in the Cell Cycle, EMBO J., 11(8): 3053-8 (Aug. 1992).
NCBI Reference Sequence: NC_006273.2.
DTU Health Tec., TMHMM Algorithm Prediction of Transmembrane Helices in Proteins http://www.cbs.dtu.dk/services/TMHMM-2.0/.
UniProt Accession No. Q777B0.
UniProtKB Accession No. F5HB53.
UniProtKB Accession No. P06437.
UniProtKB Accession No. P06473.

A

B

A

B

SEQUENCE LISTING

```
<160> NUMBER OF SEQ ID NOS: 28

<210> SEQ ID NO 1
<211> LENGTH: 906
<212> TYPE: PRT
<213> ORGANISM: Human cytomegalovirus

<400> SEQUENCE: 1

Met Glu Ser Arg Ile Trp Cys Leu Val Val Cys Val Asn Leu Cys Ile
1               5                   10                  15

Val Cys Leu Gly Ala Ala Val Ser Ser Ser Ser Thr Ser His Ala Thr
            20                  25                  30

Ser Ser Thr His Asn Gly Ser His Thr Ser Arg Thr Thr Ser Ala Gln
        35                  40                  45

Thr Arg Ser Val Tyr Ser Gln His Val Thr Ser Ser Glu Ala Val Ser
    50                  55                  60

His Arg Ala Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Ile Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
    130                 135                 140

Lys Val Leu Thr Phe Arg Arg Ser Tyr Ala Tyr Ile Tyr Thr Thr Tyr
145                 150                 155                 160

Leu Leu Gly Ser Asn Thr Glu Tyr Val Ala Pro Pro Met Trp Glu Ile
                165                 170                 175

His His Ile Asn Lys Phe Ala Gln Cys Tyr Ser Ser Tyr Ser Arg Val
            180                 185                 190

Ile Gly Gly Thr Val Phe Val Ala Tyr His Arg Asp Ser Tyr Glu Asn
        195                 200                 205

Lys Thr Met Gln Leu Ile Pro Asp Asp Tyr Ser Asn Thr His Ser Thr
    210                 215                 220
```

```
Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Leu Thr Ile Thr Thr
                245                 250                 255

Ala Arg Ser Lys Tyr Pro Tyr His Phe Phe Ala Thr Ser Thr Gly Asp
            260                 265                 270

Val Val Tyr Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
    290                 295                 300

Ile Val Ser Asp Phe Gly Arg Pro Asn Ala Ala Pro Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
    370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Ser Gly Gly Leu Val Val Phe Trp Gln
            420                 425                 430

Gly Ile Lys Gln Lys Ser Leu Val Glu Leu Glu Arg Leu Ala Asn Arg
        435                 440                 445

Ser Ser Leu Asn Ile Thr His Arg Thr Arg Arg Ser Thr Ser Asp Asn
    450                 455                 460

Asn Thr Thr His Leu Ser Ser Met Glu Ser Val His Asn Leu Val Tyr
465                 470                 475                 480

Ala Gln Leu Gln Phe Thr Tyr Asp Thr Leu Arg Gly Tyr Ile Asn Arg
                485                 490                 495

Ala Leu Ala Gln Ile Ala Glu Ala Trp Cys Val Asp Gln Arg Arg Thr
            500                 505                 510

Leu Glu Val Phe Lys Glu Leu Ser Lys Ile Asn Pro Ser Ala Ile Leu
        515                 520                 525

Ser Ala Ile Tyr Asn Lys Pro Ile Ala Ala Arg Phe Met Gly Asp Val
    530                 535                 540

Leu Gly Leu Ala Ser Cys Val Thr Ile Asn Gln Thr Ser Val Lys Val
545                 550                 555                 560

Leu Arg Asp Met Asn Val Lys Glu Ser Pro Gly Arg Cys Tyr Ser Arg
                565                 570                 575

Pro Val Val Ile Phe Asn Phe Ala Asn Ser Ser Tyr Val Gln Tyr Gly
            580                 585                 590

Gln Leu Gly Glu Asp Asn Glu Ile Leu Leu Gly Asn His Arg Thr Glu
        595                 600                 605

Glu Cys Gln Leu Pro Ser Leu Lys Ile Phe Ile Ala Gly Asn Ser Ala
    610                 615                 620

Tyr Glu Tyr Val Asp Tyr Leu Phe Lys Arg Met Ile Asp Leu Ser Ser
625                 630                 635                 640

Ile Ser Thr Val Asp Ser Met Ile Ala Leu Asp Ile Asp Pro Leu Glu
```

```
                645                 650                 655

Asn Thr Asp Phe Arg Val Leu Glu Leu Tyr Ser Gln Lys Glu Leu Arg
            660                 665                 670

Ser Ser Asn Val Phe Asp Leu Glu Glu Ile Met Arg Glu Phe Asn Ser
        675                 680                 685

Tyr Lys Gln Arg Val Lys Tyr Val Glu Asp Lys Val Val Asp Pro Leu
    690                 695                 700

Pro Pro Tyr Leu Lys Gly Leu Asp Asp Leu Met Ser Gly Leu Gly Ala
705                 710                 715                 720

Ala Gly Lys Ala Val Gly Val Ala Ile Gly Ala Val Gly Gly Ala Val
                725                 730                 735

Ala Ser Val Val Glu Gly Val Ala Thr Phe Leu Lys Asn Pro Phe Gly
            740                 745                 750

Ala Phe Thr Ile Ile Leu Val Ala Ile Ala Val Val Ile Ile Thr Tyr
        755                 760                 765

Leu Ile Tyr Thr Arg Gln Arg Arg Leu Cys Thr Gln Pro Leu Gln Asn
    770                 775                 780

Leu Phe Pro Tyr Leu Val Ser Ala Asp Gly Thr Thr Val Thr Ser Gly
785                 790                 795                 800

Ser Thr Lys Asp Thr Ser Leu Gln Ala Pro Pro Ser Tyr Glu Glu Ser
                805                 810                 815

Val Tyr Asn Ser Gly Arg Lys Gly Pro Gly Pro Pro Ser Ser Asp Ala
            820                 825                 830

Ser Thr Ala Ala Pro Pro Tyr Thr Asn Glu Gln Ala Tyr Gln Met Leu
        835                 840                 845

Leu Ala Leu Ala Arg Leu Asp Ala Glu Gln Arg Ala Gln Gln Asn Gly
    850                 855                 860

Thr Asp Ser Leu Asp Gly Gln Thr Gly Thr Gln Asp Lys Gly Gln Lys
865                 870                 875                 880

Pro Asn Leu Leu Asp Arg Leu Arg His Arg Lys Asn Gly Tyr Arg His
                885                 890                 895

Leu Lys Asp Ser Asp Glu Glu Glu Asn Val
            900                 905


<210> SEQ ID NO 2
<211> LENGTH: 2721
<212> TYPE: DNA
<213> ORGANISM: Human cytomegalovirus

<400> SEQUENCE: 2

atggaatcca ggatctggtg cctggtagtc tgcgttaacc tgtgtatcgt ctgtctgggt      60

gctgcggttt cctcttctag tacttcccat gcaacttctt ctactcacaa tggaagccat     120

acttctcgta cgacgtctgc tcaaacccgg tcagtctatt ctcaacacgt aacgtcttct     180

gaagccgtca gtcatagagc caacgagact atctacaaca ctaccctcaa gtacggagat     240

gtggtgggag tcaacactac caagtacccc tatcgcgtgt gttctatggc ccagggtacg     300

gatcttattc gctttgaacg taatatcatc tgcacctcga tgaagcctat caatgaagac     360

ttggatgagg gcatcatggt ggtctacaag cgcaacatcg tggcgcacac ctttaaggta     420

cgggtctacc aaaaggtttt gacgtttcgt cgtagctacg cttacatcta caccacttat     480

ctgctgggca gcaatacgga atacgtggcg cctcctatgt gggagattca tcacatcaac     540

aagtttgctc aatgctacag ttcctacagc cgcgttatag gaggcacggt tttcgtggca     600

tatcataggg acagttatga aaacaaaacc atgcaattaa ttcccgacga ttattccaac     660
```

```
acccacagta cccgttacgt gacggtcaag gatcagtggc acagccgcgg cagcacctgg    720

ctctatcgtg agacctgtaa tctgaactgt atgctgacca tcactactgc gcgctccaag    780

tatccttatc attttttgc aacttccacg ggtgatgtgg tttacatttc tcctttctac    840

aacggaacca atcgcaatgc cagctacttt ggagaaaacg ccgacaagtt tttcattttc    900

ccgaactaca ccatcgtttc cgactttgga agacccaacg ctgcgccaga aacccatagg    960

ttggtggctt ttctcgaacg tgccgactcg gtgatctctt gggatataca ggacgagaag   1020

aatgtcacct gccagctcac cttctgggaa gcctcggaac gtactatccg ttccgaagcc   1080

gaagactcgt accacttttc ttctgccaaa atgactgcaa cttttctgtc taagaaacaa   1140

gaagtgaaca tgtccgactc cgcgctggac tgcgtacgtg atgaggctat aaataagtta   1200

cagcagattt tcaatacttc atacaatcaa acatatgaaa aatacggaaa cgtgtccgtc   1260

ttcgaaacca gcggcggtct ggtggtgttc tggcaaggca tcaagcaaaa atctttggtg   1320

gaattggaac gtttggccaa tcgatccagt ctgaatatca ctcataggac cagaagaagt   1380

acgagtgaca ataatacaac tcatttgtcc agcatggaat cggtgcacaa tctggtctac   1440

gcccagctgc agttcaccta tgacacgttg cgcggttaca tcaaccgggc gctggcgcaa   1500

atcgcagaag cctggtgtgt ggatcaacgg cgcaccctag aggtcttcaa ggaactcagc   1560

aagatcaacc cgtcagccat tctctcggcc atttacaaca aaccgattgc cgcgcgtttc   1620

atgggtgatg tcttgggcct ggccagctgc gtgaccatca accaaaccag cgtcaaggtg   1680

ctgcgtgata tgaacgtgaa ggaatcgcca ggacgctgct actcacgacc cgtggtcatc   1740

tttaatttcg ccaacagctc gtacgtgcag tacggtcaac tgggcgagga caacgaaatc   1800

ctgttgggca accaccgcac tgaggaatgt cagcttccca gcctcaagat cttcatcgcc   1860

gggaactcgg cctacgagta cgtggactac ctcttcaaac gcatgattga cctcagcagt   1920

atctccaccg tcgacagcat gatcgccctg gatatcgacc cgctggaaaa taccgacttc   1980

agggtactgg aactttactc gcagaaagag ctgcgttcca gcaacgtttt tgacctcgaa   2040

gagatcatgc gcgaattcaa ctcgtacaag cagcgggtaa agtacgtgga ggacaaggta   2100

gtcgacccgc taccgcccta cctcaagggt ctggacgacc tcatgagcgg cctgggcgcc   2160

gcgggaaagg ccgttggcgt agccattggg gccgtgggtg gcgcggtggc ctccgtggtc   2220

gaaggcgttg ccaccttcct caaaaacccc ttcggagcct tcaccatcat cctcgtggcc   2280

atagccgtag tcattatcac ttatttgatc tatactcgac agcggcgtct gtgcacgcag   2340

ccgctgcaga acctctttcc ctatctggtg tccgccgacg ggaccaccgt gacgtcgggc   2400

agcaccaaag acacgtcgtt acaggctccg ccttcctacg aggaaagtgt ttataattct   2460

ggtcgcaaag gaccgggacc accgtcgtct gatgcatcca cggcggctcc gccttacacc   2520

aacgagcagg cttaccagat gcttctggcc ctggcccgtc tggacgcaga gcagcgagcg   2580

cagcagaacg gtacagattc tttggacgga cagactggca cgcaggacaa gggacagaag   2640

cctaacctgc tagaccggct gcgacatcgc aaaaacggct acagacactt gaaagactcc   2700

gacgaagaag agaacgtctg a                                             2721
```

<210> SEQ ID NO 3
<211> LENGTH: 904
<212> TYPE: PRT
<213> ORGANISM: Artificial Sequence
<220> FEATURE:
<223> OTHER INFORMATION: illustrative HSV-1 (strain KOS) gB sequence

<400> SEQUENCE: 3

Met His Gln Gly Ala Pro Ser Trp Gly Arg Arg Trp Phe Val Val Trp
1 5 10 15

Ala Leu Leu Gly Leu Thr Leu Gly Val Leu Val Ala Ser Ala Ala Pro
20 25 30

Thr Ser Pro Gly Thr Pro Gly Val Ala Ala Ala Thr Gln Ala Ala Asn
35 40 45

Gly Gly Pro Ala Thr Pro Ala Pro Pro Pro Leu Gly Ala Ala Pro Thr
50 55 60

Gly Asp Pro Lys Pro Lys Lys Asn Lys Lys Pro Lys Asn Pro Thr Pro
65 70 75 80

Pro Arg Pro Ala Gly Asp Asn Ala Thr Val Ala Ala Gly His Ala Thr
85 90 95

Leu Arg Glu His Leu Arg Asp Ile Lys Ala Glu Asn Thr Asp Ala Asn
100 105 110

Phe Tyr Val Cys Pro Pro Pro Thr Gly Ala Thr Val Val Gln Phe Glu
115 120 125

Gln Pro Arg Arg Cys Pro Thr Arg Pro Glu Gly Gln Asn Tyr Thr Glu
130 135 140

Gly Ile Ala Val Val Phe Lys Glu Asn Ile Ala Pro Tyr Lys Phe Lys
145 150 155 160

Ala Thr Met Tyr Tyr Lys Asp Val Thr Val Ser Gln Val Trp Phe Gly
165 170 175

His Arg Tyr Ser Gln Phe Met Gly Ile Phe Glu Asp Arg Ala Pro Val
180 185 190

Pro Phe Glu Glu Val Ile Asp Lys Ile Asn Ala Lys Gly Val Cys Arg
195 200 205

Ser Thr Ala Lys Tyr Val Arg Asn Asn Leu Glu Thr Thr Ala Phe His
210 215 220

Arg Asp Asp His Glu Thr Asp Met Glu Leu Lys Pro Ala Asn Ala Ala
225 230 235 240

Thr Arg Thr Ser Arg Gly Trp His Thr Thr Asp Leu Lys Tyr Asn Pro
245 250 255

Ser Arg Val Glu Ala Phe His Arg Tyr Gly Thr Thr Val Asn Cys Ile
260 265 270

Val Glu Glu Val Asp Ala Arg Ser Val Tyr Pro Tyr Asp Glu Phe Val
275 280 285

Leu Ala Thr Gly Asp Phe Val Tyr Met Ser Pro Phe Tyr Gly Tyr Arg
290 295 300

Glu Gly Ser His Thr Glu His Thr Thr Tyr Ala Ala Asp Arg Phe Lys
305 310 315 320

Gln Val Asp Gly Phe Tyr Ala Arg Asp Leu Thr Thr Lys Ala Arg Ala
325 330 335

Thr Ala Pro Thr Thr Arg Asn Leu Leu Thr Thr Pro Lys Phe Thr Val
340 345 350

Ala Trp Asp Trp Val Pro Lys Arg Pro Ser Val Cys Thr Met Thr Lys
355 360 365

Trp Gln Glu Val Asp Glu Met Leu Arg Ser Glu Tyr Gly Gly Ser Phe
370 375 380

Arg Phe Ser Ser Asp Ala Ile Ser Thr Thr Phe Thr Thr Asn Leu Thr
385 390 395 400

Glu Tyr Pro Leu Ser Arg Val Asp Leu Gly Asp Cys Ile Gly Lys Asp
405 410 415

```
Ala Arg Asp Ala Met Asp Arg Ile Phe Ala Arg Arg Tyr Asn Ala Thr
            420                 425                 430

His Ile Lys Val Gly Gln Pro Gln Tyr Tyr Gln Ala Asn Gly Gly Phe
        435                 440                 445

Leu Ile Ala Tyr Gln Pro Leu Leu Ser Asn Thr Leu Ala Glu Leu Tyr
    450                 455                 460

Val Arg Glu His Leu Arg Glu Gln Ser Arg Lys Pro Pro Asn Pro Thr
465                 470                 475                 480

Pro Pro Pro Pro Gly Ala Ser Ala Asn Ala Ser Val Glu Arg Ile Lys
                485                 490                 495

Thr Thr Ser Ser Ile Glu Phe Ala Arg Leu Gln Phe Thr Tyr Asn His
            500                 505                 510

Ile Gln Arg His Val Asn Asp Met Leu Gly Arg Val Ala Ile Ala Trp
        515                 520                 525

Cys Glu Leu Gln Asn His Glu Leu Thr Leu Trp Asn Glu Ala Arg Lys
    530                 535                 540

Leu Asn Pro Asn Ala Ile Ala Ser Val Thr Val Gly Arg Arg Val Ser
545                 550                 555                 560

Ala Arg Met Leu Gly Asp Val Met Ala Val Ser Thr Cys Val Pro Val
                565                 570                 575

Ala Ala Asp Asn Val Ile Val Gln Asn Ser Met Arg Ile Ser Ser Arg
            580                 585                 590

Pro Gly Ala Cys Tyr Ser Arg Pro Leu Val Ser Phe Arg Tyr Glu Asp
        595                 600                 605

Gln Gly Pro Leu Val Glu Gly Gln Leu Gly Glu Asn Asn Glu Leu Arg
    610                 615                 620

Leu Thr Arg Asp Ala Ile Glu Pro Cys Thr Val Gly His Arg Arg Tyr
625                 630                 635                 640

Phe Thr Phe Gly Gly Gly Tyr Val Tyr Phe Glu Glu Tyr Ala Tyr Ser
                645                 650                 655

His Gln Leu Ser Arg Ala Asp Ile Thr Thr Val Ser Thr Phe Ile Asp
            660                 665                 670

Leu Asn Ile Thr Met Leu Glu Asp His Glu Phe Val Pro Leu Glu Val
        675                 680                 685

Tyr Thr Arg His Glu Ile Lys Asp Ser Gly Leu Leu Asp Tyr Thr Glu
    690                 695                 700

Val Gln Arg Arg Asn Gln Leu His Asp Leu Arg Phe Ala Asp Ile Asp
705                 710                 715                 720

Thr Val Ile His Ala Asp Ala Asn Ala Ala Met Phe Ala Gly Leu Gly
                725                 730                 735

Ala Phe Phe Glu Gly Met Gly Asp Leu Gly Arg Ala Val Gly Lys Val
            740                 745                 750

Val Met Gly Ile Val Gly Gly Val Val Ser Ala Val Ser Gly Val Ser
        755                 760                 765

Ser Phe Met Ser Asn Pro Phe Gly Ala Leu Ala Val Gly Leu Leu Val
    770                 775                 780

Leu Ala Gly Leu Ala Ala Ala Phe Phe Ala Phe Arg Tyr Val Met Arg
785                 790                 795                 800

Leu Gln Ser Asn Pro Met Lys Ala Leu Tyr Pro Leu Thr Thr Lys Glu
                805                 810                 815

Leu Lys Asn Pro Thr Asn Pro Asp Ala Ser Gly Glu Gly Glu Glu Gly
            820                 825                 830
```

```
Gly Asp Phe Asp Glu Ala Lys Leu Ala Glu Ala Arg Glu Met Ile Arg
        835                 840                 845

Tyr Met Ala Leu Val Ser Ala Met Glu Arg Thr Glu His Lys Ala Lys
    850                 855                 860

Lys Lys Gly Thr Ser Ala Leu Leu Ser Ala Lys Val Thr Asp Met Val
865                 870                 875                 880

Met Arg Lys Arg Arg Asn Thr Asn Tyr Thr Gln Val Pro Asn Lys Asp
                885                 890                 895

Gly Asp Ala Asp Glu Asp Asp Leu
            900


<210> SEQ ID NO 4
<211> LENGTH: 2715
<212> TYPE: DNA
<213> ORGANISM: Artificial Sequence
<220> FEATURE:
<223> OTHER INFORMATION: illustrative HSV-1 (strain KOS) gB sequence

<400> SEQUENCE: 4

atgcaccagg gcgcccccctc gtgggggcgc cggtggttcg tcgtatgggc gctcttgggg     60

ttgacgctgg gggtcctggt ggcgtcggcg gctccgactt cccccggcac gcctggggtc    120

gcggccgcga cccaggcggc gaacgggggc cctgccactc cggcgccgcc gccccttggc    180

gccgccccaa cgggggaccc gaaaccgaag aagaacaaaa aaccgaaaaa cccaacgcca    240

ccacgccccg ccggcgacaa cgcgaccgtc gccgcgggcc acgccaccct gcgcgagcac    300

ctgcgggaca tcaaggcgga gaacaccgat gcaaactttt acgtgtgccc accccccacg    360

ggcgccacgg tggtgcagtt cgagcagccg cgccgctgcc cgacccggcc cgagggtcag    420

aactacacgg agggcatcgc ggtggtcttc aaggagaaca tcgccccgta caagttcaag    480

gccaccatgt actacaaaga cgtcaccgtt tcgcaggtgt ggttcggcca ccgctactcc    540

cagtttatgg ggatctttga ggaccgcgcc cccgtcccct tcgaggaggt gatcgacaag    600

atcaacgcca agggggtctg tcggtccacg gccaagtacg tgcgcaacaa cctggagacc    660

accgcgtttc accgggacga ccacgagacc gacatggagc tgaaaccggc caacgccgcg    720

acccgcacga gccggggctg gcacaccacc gacctcaagt acaacccctc gcgggtggag    780

gcgttccacc ggtacgggac gacggtaaac tgcatcgtcg aggaggtgga cgcgcgctcg    840

gtgtacccgt acgacgagtt tgtgctggcg actggcgact ttgtgtacat gtccccgttt    900

tacggctacc gggaggggtc gcacaccgaa cacaccacgt acgccgccga ccgcttcaag    960

caggtcgacg gcttctacgc gcgcgacctc accaccaagg cccgggccac ggcgccgacc   1020

acccggaacc tgctcacgac ccccaagttc accgtggcct gggactgggt gccaaagcgc   1080

ccgtcggtct gcaccatgac caagtggcag gaagtggacg agatgctgcg ctccgagtac   1140

ggcggctcct tccgattctc ctccgacgcc atatccacca ccttcaccac caacctgacc   1200

gagtacccgc tctcgcgcgt ggacctgggg gactgcatcg gcaaggacgc ccgcgacgcc   1260

atggaccgca tcttcgcccg caggtacaac gcgacgcaca tcaaggtggg ccagccgcag   1320

tactaccagg ccaatggggg ctttctgatc gcgtaccagc cccttctcag caacacgctc   1380

gcggagctgt acgtgcggga acacctccga gagcagagcc gcaagccccc aaaccccacg   1440

cccccgccgc ccggggccag cgccaacgcg tccgtggagc gcatcaagac cacctcctcc   1500

atcgagttcg cccggctgca gtttacgtac aaccacatac agcgccatgt caacgatatg   1560

ttgggccgcg ttgccatcgc gtggtgcgag ctacagaatc acgagctgac cctgtggaac   1620
```

gaggcccgca agctgaaccc caacgccatc gcctcggtca ccgtgggccg gcgggtgagc 1680
gcgcggatgc tcggcgacgt gatggccgtc tccacgtgcg tgccggtcgc cgcggacaac 1740
gtgatcgtcc aaaactcgat gcgcatcagc tcgcggcccg gggcctgcta cagccgcccc 1800
ctggtcagct ttcggtacga agaccagggc ccgttggtcg aggggcagct gggggagaac 1860
aacgagctgc ggctgacgcg cgatgcgatc gagccgtgca ccgtgggaca ccggcgctac 1920
ttcaccttcg gtgggggcta cgtgtacttc gaggagtacg cgtactccca ccagctgagc 1980
cgcgccgaca tcaccaccgt cagcaccttc atcgacctca acatcaccat gctggaggat 2040
cacgagtttg tcccccctgga ggtgtacacc cgccacgaga tcaaggacag cggcctgctg 2100
gactacacgg aggtccagcg ccgcaaccag ctgcacgacc tgcgcttcgc cgacatcgac 2160
acggtcatcc acgccgacgc caacgccgcc atgttcgcgg gcctgggcgc gttcttcgag 2220
gggatgggcg acctggggcg cgcggtcggc aaggtggtga tgggcatcgt gggcggcgtg 2280
gtatcggccg tgtcgggcgt gtcctccttc atgtccaacc cctttggggc gctggccgtg 2340
ggtctgttgg tcctggccgg cctggcggcg gccttcttcg cctttcgtta cgtcatgcgg 2400
ctgcagagca accccatgaa ggccctgtac cctctaacca ccaaggagct caagaacccc 2460
accaacccgg acgcgtccgg ggagggcgag gagggcggcg actttgacga ggccaagcta 2520
gccgaggcca gggagatgat acggtacatg gccctggtgt cggccatgga gcgcacggaa 2580
cacaaggcca agaagaaggg cacgagcgcg ctgctcagcg ccaaggtcac cgacatggtc 2640
atgcgcaagc gccgcaacac caactacacc caagttccca acaaagacgg tgacgccgac 2700
gaggacgacc tgtga 2715

<210> SEQ ID NO 5
<211> LENGTH: 857
<212> TYPE: PRT
<213> ORGANISM: Artificial Sequence
<220> FEATURE:
<223> OTHER INFORMATION: illustrative EBV (strain B958) gB sequence

<400> SEQUENCE: 5

Met Thr Arg Arg Arg Val Leu Ser Val Val Val Leu Leu Ala Ala Leu
1 5 10 15

Ala Cys Arg Leu Gly Ala Gln Thr Pro Glu Gln Pro Ala Pro Pro Ala
20 25 30

Thr Thr Val Gln Pro Thr Ala Thr Arg Gln Gln Thr Ser Phe Pro Phe
35 40 45

Arg Val Cys Glu Leu Ser Ser His Gly Asp Leu Phe Arg Phe Ser Ser
50 55 60

Asp Ile Gln Cys Pro Ser Phe Gly Thr Arg Glu Asn His Thr Glu Gly
65 70 75 80

Leu Leu Met Val Phe Lys Asp Asn Ile Ile Pro Tyr Ser Phe Lys Val
85 90 95

Arg Ser Tyr Thr Lys Ile Val Thr Asn Ile Leu Ile Tyr Asn Gly Trp
100 105 110

Tyr Ala Asp Ser Val Thr Asn Arg His Glu Glu Lys Phe Ser Val Asp
115 120 125

Ser Tyr Glu Thr Asp Gln Met Asp Thr Ile Tyr Gln Cys Tyr Asn Ala
130 135 140

Val Lys Met Thr Lys Asp Gly Leu Thr Arg Val Tyr Val Asp Arg Asp
145 150 155 160

Gly Val Asn Ile Thr Val Asn Leu Lys Pro Thr Gly Gly Leu Ala Asn

```
                165                 170                 175

Gly Val Arg Arg Tyr Ala Ser Gln Thr Glu Leu Tyr Asp Ala Pro Gly
            180                 185                 190

Trp Leu Ile Trp Thr Tyr Arg Thr Arg Thr Thr Val Asn Cys Leu Ile
        195                 200                 205

Thr Asp Met Met Ala Lys Ser Asn Ser Pro Phe Asp Phe Phe Val Thr
    210                 215                 220

Thr Thr Gly Gln Thr Val Glu Met Ser Pro Phe Tyr Asp Gly Lys Asn
225                 230                 235                 240

Lys Glu Thr Phe His Glu Arg Ala Asp Ser Phe His Val Arg Thr Asn
                245                 250                 255

Tyr Lys Ile Val Asp Tyr Asp Asn Arg Gly Thr Asn Pro Gln Gly Glu
            260                 265                 270

Arg Arg Ala Phe Leu Asp Lys Gly Thr Tyr Thr Leu Ser Trp Lys Leu
        275                 280                 285

Glu Asn Arg Thr Ala Tyr Cys Pro Leu Gln His Trp Gln Thr Phe Asp
    290                 295                 300

Ser Thr Ile Ala Thr Glu Thr Gly Lys Ser Ile His Phe Val Thr Asp
305                 310                 315                 320

Glu Gly Thr Ser Ser Phe Val Thr Asn Thr Thr Val Gly Ile Glu Leu
                325                 330                 335

Pro Asp Ala Phe Lys Cys Ile Glu Glu Gln Val Asn Lys Thr Met His
            340                 345                 350

Glu Lys Tyr Glu Ala Val Gln Asp Arg Tyr Thr Lys Gly Gln Glu Ala
        355                 360                 365

Ile Thr Tyr Phe Ile Thr Ser Gly Gly Leu Leu Leu Ala Trp Leu Pro
    370                 375                 380

Leu Thr Pro Arg Ser Leu Ala Thr Val Lys Asn Leu Thr Glu Leu Thr
385                 390                 395                 400

Thr Pro Thr Ser Ser Pro Pro Ser Ser Pro Ser Pro Pro Ala Pro Ser
                405                 410                 415

Ala Ala Arg Gly Ser Thr Pro Ala Ala Val Leu Arg Arg Arg Arg Arg
            420                 425                 430

Asp Ala Gly Asn Ala Thr Thr Pro Val Pro Pro Thr Ala Pro Gly Lys
        435                 440                 445

Ser Leu Gly Thr Leu Asn Asn Pro Ala Thr Val Gln Ile Gln Phe Ala
    450                 455                 460

Tyr Asp Ser Leu Arg Arg Gln Ile Asn Arg Met Leu Gly Asp Leu Ala
465                 470                 475                 480

Arg Ala Trp Cys Leu Glu Gln Lys Arg Gln Asn Met Val Leu Arg Glu
                485                 490                 495

Leu Thr Lys Ile Asn Pro Thr Thr Val Met Ser Ser Ile Tyr Gly Lys
            500                 505                 510

Ala Val Ala Ala Lys Arg Leu Gly Asp Val Ile Ser Val Ser Gln Cys
        515                 520                 525

Val Pro Val Asn Gln Ala Thr Val Thr Leu Arg Lys Ser Met Arg Val
    530                 535                 540

Pro Gly Ser Glu Thr Met Cys Tyr Ser Arg Pro Leu Val Ser Phe Ser
545                 550                 555                 560

Phe Ile Asn Asp Thr Lys Thr Tyr Glu Gly Gln Leu Gly Thr Asp Asn
                565                 570                 575

Glu Ile Phe Leu Thr Lys Lys Met Thr Glu Val Cys Gln Ala Thr Ser
            580                 585                 590
```

Gln Tyr Tyr Phe Gln Ser Gly Asn Glu Ile His Val Tyr Asn Asp Tyr
595 600 605

His His Phe Lys Thr Ile Glu Leu Asp Gly Ile Ala Thr Leu Gln Thr
610 615 620

Phe Ile Ser Leu Asn Thr Ser Leu Ile Glu Asn Ile Asp Phe Ala Ser
625 630 635 640

Leu Glu Leu Tyr Ser Arg Asp Glu Gln Arg Ala Ser Asn Val Phe Asp
645 650 655

Leu Glu Gly Ile Phe Arg Glu Tyr Asn Phe Gln Ala Gln Asn Ile Ala
660 665 670

Gly Leu Arg Lys Asp Leu Asp Asn Ala Val Ser Asn Gly Arg Asn Gln
675 680 685

Phe Val Asp Gly Leu Gly Glu Leu Met Asp Ser Leu Gly Ser Val Gly
690 695 700

Gln Ser Ile Thr Asn Leu Val Ser Thr Val Gly Gly Leu Phe Ser Ser
705 710 715 720

Leu Val Ser Gly Phe Ile Ser Phe Phe Lys Asn Pro Phe Gly Gly Met
725 730 735

Leu Ile Leu Val Leu Val Ala Gly Val Val Ile Leu Val Ile Ser Leu
740 745 750

Thr Arg Arg Thr Arg Gln Met Ser Gln Gln Pro Val Gln Met Leu Tyr
755 760 765

Pro Gly Ile Asp Glu Leu Ala Gln Gln His Ala Ser Gly Glu Gly Pro
770 775 780

Gly Ile Asn Pro Ile Ser Lys Thr Glu Leu Gln Ala Ile Met Leu Ala
785 790 795 800

Leu His Glu Gln Asn Gln Glu Gln Lys Arg Ala Ala Gln Arg Ala Ala
805 810 815

Gly Pro Ser Val Ala Ser Arg Ala Leu Gln Ala Ala Arg Asp Arg Phe
820 825 830

Pro Gly Leu Arg Arg Arg Arg Tyr His Asp Pro Glu Thr Ala Ala Ala
835 840 845

Leu Leu Gly Glu Ala Glu Thr Glu Phe
850 855

<210> SEQ ID NO 6
<211> LENGTH: 2573
<212> TYPE: DNA
<213> ORGANISM: Artificial Sequence
<220> FEATURE:
<223> OTHER INFORMATION: illustrative EBV (strain B958) gB sequence

<400> SEQUENCE: 6
atgactcggc gtagggtgct aagcgtggtc gtgctgctag ccgccctggc gtgccgtctc 60
ggtgcgcaga ccccagagca gcccgcaccc cccgccacca cggtgcagcc taccgccacg 120
cgtcagcaaa ccagctttcc tttccgagtc tgcgagctct ccagccacgg cgacctgttc 180
cgcttctcct cggacatcca gtgtccctcg tttggcacgc gggagaatca cacggagggc 240
ctgttgatgg tgtttaaaga caacattatt ccctactcgt ttaaggtccg ctcctacacc 300
aagatagtga ccaacattct catctacaat ggctggtacg cggactccgt gaccaaccgg 360
cacgaggaga agttctccgt tgacagctac gaaactgacc agatggatac catctaccag 420
tgctacaacg cggtcaagat gacaaaagat gggctgacgc gcgtgtatgt agaccgcgac 480
ggagttaaca tcaccgtcaa cctaaagccc accgggggcc tggccaacgg ggtgcgccgc 540

```
tacgccagcc agacggagct ctatgacgcc cccgggtggt tgatatggac ttacagaaca    600
agaactaccg tcaactgcct gataactgac atgatggcca agtccaacag ccccttcgac    660
ttctttgtga ccaccaccgg gcagactgtg gaaatgtccc ctttctatga cgggaaaaat    720
aaggaaacct tccatgagcg ggcagactcc ttccacgtga gaactaacta caagatagtg    780
gactacgaca accgagggac gaacccgcaa ggcgaacgcc gagccttcct ggacaagggc    840
acttacacgc tatcttggaa gctcgagaac aggacagcct actgcccgct tcaacactgg    900
caaacctttg actcgaccat cgccacagaa acagggaagt caatacattt tgtgactgac    960
gagggcacct ctagcttcgt gaccaacaca accgtgggca tagagctccc ggacgccttc   1020
aagtgcatcg aagagcaggt gaacaagacc atgcatgaga agtacgaggc cgtccaggat   1080
cgttacacga agggccagga agccattaca tattttataa cgagcggagg attgttatta   1140
gcttggctac ctctgacccc gcgctcgttg gccaccgtca agaacctgac ggagcttacc   1200
actccgactt cctcaccccc cagcagtcca tcgcccccag ccccatccgc ggcccgcggg   1260
agcacccccg ccgccgttct gaggcgtcgg aggcgggatg cggggaacgc caccacaccg   1320
gtgcccccca cggcccccgg gaagtccctg ggcaccctca acaatcccgc caccgtccag   1380
atccaatttg cctacgactc cctgcgccgc cagatcaacc gcatgctggg agaccttgcg   1440
cgggcctggt gcctggagca gaagaggcag aacatggtgc tgagagaact aaccaagatt   1500
aatccaacca ccgtcatgtc cagcatctac ggtaaggcgg tggcggccaa gcgcctgggg   1560
gatgtcatct cagtctccca gtgcgtgccc gttaaccagg ccaccgtcac cctgcgcaag   1620
agcatgaggg tccctggctc cgagaccatg tgctactcgc gccccctggt gtccttcagc   1680
tttatcaacg acaccaagac ctacgaggga cagctgggca ccgacaacga gatcttcctc   1740
acaaaaaaga tgacggaggt gtgccaggcg accagccagt actacttcca gtccggcaac   1800
gagatccacg tctacaacga ctaccaccac tttaaaacca tcgagctgga cggcattgcc   1860
accctgcaga ccttcatctc actaaacacc tccctcatcg agaacattga ctttgcctcc   1920
ctggagctgt actcacggga cgaacagcgt gcctccaacg tctttgacct ggagggcatc   1980
ttccgggagt acaacttcca ggcgcaaaac atcgccggcc tgcggaagga tttggacaat   2040
gcagtgtcaa acggaagaaa tcaattcgtg gacggcctgg gggaacttat ggacagtctg   2100
ggtagcgtgg gtcagtccat caccaaccta gtcagcacgg tgggggggttt gtttagcagc   2160
ctggtctctg gtttcatctc cttcttcaaa aaccccttcg gcggcatgct cattctggtc   2220
ctggtggcgg gggtggtgat cctggttatt tccctcacga ggcgcacgcg ccagatgtcg   2280
cagcagccgg tgcagatgct ctaccccggg atcgacgagc tcgctcagca acatgcctct   2340
ggtgagggtc caggcattaa tcccattagt aagacagaat tacaagccat catgttagcg   2400
ctgcatgagc aaaaccagga gcaaaagaga gcagctcaga gggcggccgg accctcagtg   2460
gccagcagag cattgcaggc agccagggac cgttttccag gcctacgcag aagacgctat   2520
cacgatccag agaccgccgc cgcactgctt ggggaggcag agactgagtt tta          2573
```

<210> SEQ ID NO 7
<211> LENGTH: 48
<212> TYPE: PRT
<213> ORGANISM: Artificial Sequence
<220> FEATURE:
<223> OTHER INFORMATION: illustrative HCMV gB AD-6 sequence

<400> SEQUENCE: 7

```
Met Ile Ala Leu Asp Ile Asp Pro Leu Glu Asn Thr Asp Phe Arg Val
1               5                   10                  15

Leu Glu Leu Tyr Ser Gln Lys Glu Leu Arg Ser Ser Asn Val Phe Asp
            20                  25                  30

Leu Glu Glu Ile Met Arg Glu Phe Asn Ser Tyr Lys Gln Arg Val Lys
        35                  40                  45


<210> SEQ ID NO 8
<211> LENGTH: 144
<212> TYPE: DNA
<213> ORGANISM: Artificial Sequence
<220> FEATURE:
<223> OTHER INFORMATION: illustrative HCMV gB AD-6 sequence

<400> SEQUENCE: 8

atgatcgccc tggatatcga cccgctggaa aataccgact tcagggtact ggaactttac      60

tcgcagaaag agctgcgttc cagcaacgtt tttgacctcg aagagatcat gcgcgaattc     120

aactcgtaca agcagcgggt aaag                                            144


<210> SEQ ID NO 9
<211> LENGTH: 48
<212> TYPE: PRT
<213> ORGANISM: Artificial Sequence
<220> FEATURE:
<223> OTHER INFORMATION: illustrative HSV-1 gB AD-6 sequence

<400> SEQUENCE: 9

Phe Ile Asp Leu Asn Ile Thr Met Leu Glu Asp His Glu Phe Val Pro
1               5                   10                  15

Leu Glu Val Tyr Thr Arg His Glu Ile Lys Asp Ser Gly Leu Leu Asp
            20                  25                  30

Tyr Thr Glu Val Gln Arg Arg Asn Gln Leu His Asp Leu Arg Phe Ala
        35                  40                  45


<210> SEQ ID NO 10
<211> LENGTH: 144
<212> TYPE: DNA
<213> ORGANISM: Artificial Sequence
<220> FEATURE:
<223> OTHER INFORMATION: illustrative HSV-1 gB AD-6 sequence

<400> SEQUENCE: 10

ttcatcgacc tcaacatcac catgctggag gatcacgagt ttgtcccct ggaggtgtac      60

acccgccacg agatcaagga cagcggcctg ctggactaca cggaggtcca gcgccgcaac     120

cagctgcacg acctgcgctt cgcc                                            144


<210> SEQ ID NO 11
<211> LENGTH: 48
<212> TYPE: PRT
<213> ORGANISM: Artificial Sequence
<220> FEATURE:
<223> OTHER INFORMATION: illustrative EBV gB AD-6 sequence

<400> SEQUENCE: 11

Phe Ile Ser Leu Asn Thr Ser Leu Ile Glu Asn Ile Asp Phe Ala Ser
1               5                   10                  15

Leu Glu Leu Tyr Ser Arg Asp Glu Gln Arg Ala Ser Asn Val Phe Asp
            20                  25                  30

Leu Glu Gly Ile Phe Arg Glu Tyr Asn Phe Gln Ala Gln Asn Ile Ala
        35                  40                  45
```

<210> SEQ ID NO 12
<211> LENGTH: 144
<212> TYPE: DNA
<213> ORGANISM: Artificial Sequence
<220> FEATURE:
<223> OTHER INFORMATION: illustrative EBV gB AD-6 sequence

<400> SEQUENCE: 12
ttcatctcac taaacacctc cctcatcgag aacattgact ttgcctccct ggagctgtac 60
tcacgggacg aacagcgtgc ctccaacgtc tttgacctgg agggcatctt ccgggagtac 120
aacttccagg cgcaaaacat cgcc 144

<210> SEQ ID NO 13
<211> LENGTH: 15
<212> TYPE: PRT
<213> ORGANISM: Artificial Sequence
<220> FEATURE:
<223> OTHER INFORMATION: Illustrative immunogenic fragment of HCMV gB AD-6

<400> SEQUENCE: 13

Val Asp Ser Met Ile Ala Leu Asp Ile Asp Pro Leu Glu Asn Thr
1 5 10 15

<210> SEQ ID NO 14
<211> LENGTH: 15
<212> TYPE: PRT
<213> ORGANISM: Artificial Sequence
<220> FEATURE:
<223> OTHER INFORMATION: Illustrative immunogenic fragment of HCMV gB AD-6

<400> SEQUENCE: 14

Ile Ala Leu Asp Ile Asp Pro Leu Glu Asn Thr Asp Phe Arg Val
1 5 10 15

<210> SEQ ID NO 15
<211> LENGTH: 15
<212> TYPE: PRT
<213> ORGANISM: Artificial Sequence
<220> FEATURE:
<223> OTHER INFORMATION: Illustrative immunogenic fragment of HCMV gB AD-6

<400> SEQUENCE: 15

Ile Asp Pro Leu Glu Asn Thr Asp Phe Arg Val Leu Glu Leu Tyr
1 5 10 15

<210> SEQ ID NO 16
<211> LENGTH: 15
<212> TYPE: PRT
<213> ORGANISM: Artificial Sequence
<220> FEATURE:
<223> OTHER INFORMATION: Illustrative immunogenic fragment of HCMV gB AD-6

<400> SEQUENCE: 16

Glu Asn Thr Asp Phe Arg Val Leu Glu Leu Tyr Ser Gln Lys Glu
1 5 10 15

<210> SEQ ID NO 17
<211> LENGTH: 15
<212> TYPE: PRT
<213> ORGANISM: Artificial Sequence
<220> FEATURE:
<223> OTHER INFORMATION: Illustrative immunogenic fragment of HCMV gB

AD-6

<400> SEQUENCE: 17

Phe Arg Val Leu Glu Leu Tyr Ser Gln Lys Glu Leu Arg Ser Ser
1 5 10 15

<210> SEQ ID NO 18
<211> LENGTH: 15
<212> TYPE: PRT
<213> ORGANISM: Artificial Sequence
<220> FEATURE:
<223> OTHER INFORMATION: Illustrative immunogenic fragment of HCMV gB AD-6

<400> SEQUENCE: 18

Glu Leu Tyr Ser Gln Lys Glu Leu Arg Ser Ser Asn Val Phe Asp
1 5 10 15

<210> SEQ ID NO 19
<211> LENGTH: 15
<212> TYPE: PRT
<213> ORGANISM: Artificial Sequence
<220> FEATURE:
<223> OTHER INFORMATION: Illustrative immunogenic fragment of HCMV gB AD-6

<400> SEQUENCE: 19

Gln Lys Glu Leu Arg Ser Ser Asn Val Phe Asp Leu Glu Glu Ile
1 5 10 15

<210> SEQ ID NO 20
<211> LENGTH: 15
<212> TYPE: PRT
<213> ORGANISM: Artificial Sequence
<220> FEATURE:
<223> OTHER INFORMATION: Illustrative immunogenic fragment of HCMV gB AD-6

<400> SEQUENCE: 20

Arg Ser Ser Asn Val Phe Asp Leu Glu Glu Ile Met Arg Glu Phe
1 5 10 15

<210> SEQ ID NO 21
<211> LENGTH: 15
<212> TYPE: PRT
<213> ORGANISM: Artificial Sequence
<220> FEATURE:
<223> OTHER INFORMATION: Illustrative immunogenic fragment of HCMV gB AD-6

<400> SEQUENCE: 21

Val Phe Asp Leu Glu Glu Ile Met Arg Glu Phe Asn Ser Tyr Lys
1 5 10 15

<210> SEQ ID NO 22
<211> LENGTH: 15
<212> TYPE: PRT
<213> ORGANISM: Artificial Sequence
<220> FEATURE:
<223> OTHER INFORMATION: Illustrative immunogenic fragment of HCMV gB AD-6

<400> SEQUENCE: 22

Glu Glu Ile Met Arg Glu Phe Asn Ser Tyr Lys Gln Arg Val Lys
1 5 10 15

<210> SEQ ID NO 23

<211> LENGTH: 15
<212> TYPE: PRT
<213> ORGANISM: Artificial Sequence
<220> FEATURE:
<223> OTHER INFORMATION: Illustrative immunogenic fragment of HCMV gB AD-6

<400> SEQUENCE: 23

Arg Glu Phe Asn Ser Tyr Lys Gln Arg Val Lys Tyr Val Glu Asp
1 5 10 15

<210> SEQ ID NO 24
<211> LENGTH: 15
<212> TYPE: PRT
<213> ORGANISM: Artificial Sequence
<220> FEATURE:
<223> OTHER INFORMATION: Illustrative immunogenic fragment of HCMV gB AD-6

<400> SEQUENCE: 24

Ser Tyr Lys Gln Arg Val Lys Tyr Val Glu Asp Lys Val Val Asp
1 5 10 15

<210> SEQ ID NO 25
<211> LENGTH: 11
<212> TYPE: PRT
<213> ORGANISM: Artificial Sequence
<220> FEATURE:
<223> OTHER INFORMATION: Illustrative immunogenic fragment of HCMV gB AD-6

<400> SEQUENCE: 25

Glu Leu Tyr Ser Gln Lys Glu Leu Arg Ser Ser
1 5 10

<210> SEQ ID NO 26
<211> LENGTH: 11
<212> TYPE: PRT
<213> ORGANISM: Artificial Sequence
<220> FEATURE:
<223> OTHER INFORMATION: Illustrative immunogenic fragment of HCMV gB AD-6

<400> SEQUENCE: 26

Ser Tyr Lys Gln Arg Val Lys Tyr Val Glu Asp
1 5 10

<210> SEQ ID NO 27
<211> LENGTH: 907
<212> TYPE: PRT
<213> ORGANISM: Human cytomegalovirus

<400> SEQUENCE: 27

Met Glu Ser Arg Ile Trp Cys Leu Val Val Cys Val Asn Leu Cys Ile
1 5 10 15

Val Cys Leu Gly Ala Ala Val Ser Ser Ser Ser Thr Arg Gly Thr Ser
20 25 30

Ala Thr His Ser His His Ser Ser His Thr Thr Ser Ala Ala His Ser
35 40 45

Arg Ser Gly Ser Val Ser Gln Arg Val Thr Ser Ser Gln Thr Val Ser
50 55 60

His Gly Val Asn Glu Thr Ile Tyr Asn Thr Thr Leu Lys Tyr Gly Asp
65 70 75 80

Val Val Gly Val Asn Thr Thr Lys Tyr Pro Tyr Arg Val Cys Ser Met
85 90 95

-continued

```
Ala Gln Gly Thr Asp Leu Ile Arg Phe Glu Arg Asn Ile Val Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
    130                 135                 140

Lys Val Leu Thr Phe Arg Arg Ser Tyr Ala Tyr Ile His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190

Ile Ala Gly Thr Val Phe Val Ala Tyr His Arg Asp Ser Tyr Glu Asn
        195                 200                 205

Lys Thr Met Gln Leu Met Pro Asp Asp Tyr Ser Asn Thr His Ser Thr
    210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Val Thr Ile Thr Thr
                245                 250                 255

Ala Arg Ser Lys Tyr Pro Tyr His Phe Phe Ala Thr Ser Thr Gly Asp
            260                 265                 270

Val Val Asp Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
    290                 295                 300

Ile Val Ser Asp Phe Gly Arg Pro Asn Ser Ala Leu Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
    370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Thr Gly Gly Leu Val Val Phe Trp Gln
            420                 425                 430

Gly Ile Lys Gln Lys Ser Leu Val Glu Leu Glu Arg Leu Ala Asn Arg
        435                 440                 445

Ser Ser Leu Asn Leu Thr His Asn Arg Thr Lys Arg Ser Thr Asp Gly
    450                 455                 460

Asn Asn Ala Thr His Leu Ser Asn Met Glu Ser Val His Asn Leu Val
465                 470                 475                 480

Tyr Ala Gln Leu Gln Phe Thr Tyr Asp Thr Leu Arg Gly Tyr Ile Asn
                485                 490                 495

Arg Ala Leu Ala Gln Ile Ala Glu Ala Trp Cys Val Asp Gln Arg Arg
            500                 505                 510
```

```
Thr Leu Glu Val Phe Lys Glu Leu Ser Lys Ile Asn Pro Ser Ala Ile
        515                 520                 525

Leu Ser Ala Ile Tyr Asn Lys Pro Ile Ala Ala Arg Phe Met Gly Asp
    530                 535                 540

Val Leu Gly Leu Ala Ser Cys Val Thr Ile Asn Gln Thr Ser Val Lys
545                 550                 555                 560

Val Leu Arg Asp Met Asn Val Lys Glu Ser Pro Gly Arg Cys Tyr Ser
                565                 570                 575

Arg Pro Val Val Ile Phe Asn Phe Ala Asn Ser Ser Tyr Val Gln Tyr
            580                 585                 590

Gly Gln Leu Gly Glu Asp Asn Glu Ile Leu Leu Gly Asn His Arg Thr
        595                 600                 605

Glu Glu Cys Gln Leu Pro Ser Leu Lys Ile Phe Ile Ala Gly Asn Ser
    610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
                645                 650                 655

Glu Asn Thr Asp Phe Arg Val Leu Glu Leu Tyr Ser Gln Lys Glu Leu
            660                 665                 670

Arg Ser Ser Asn Val Phe Asp Leu Glu Glu Ile Met Arg Glu Phe Asn
        675                 680                 685

Ser Tyr Lys Gln Arg Val Lys Tyr Val Glu Asp Lys Val Val Asp Pro
    690                 695                 700

Leu Pro Pro Tyr Leu Lys Gly Leu Asp Asp Leu Met Ser Gly Leu Gly
705                 710                 715                 720

Ala Ala Gly Lys Ala Val Gly Val Ala Ile Gly Ala Val Gly Gly Ala
                725                 730                 735

Val Ala Ser Val Val Glu Gly Val Ala Thr Phe Leu Lys Asn Pro Phe
            740                 745                 750

Gly Ala Phe Thr Ile Ile Leu Val Ala Ile Ala Val Val Ile Ile Thr
        755                 760                 765

Tyr Leu Ile Tyr Thr Arg Gln Arg Arg Leu Cys Thr Gln Pro Leu Gln
    770                 775                 780

Asn Leu Phe Pro Tyr Leu Val Ser Ala Asp Gly Thr Thr Val Thr Ser
785                 790                 795                 800

Gly Ser Thr Lys Asp Thr Ser Leu Gln Ala Pro Pro Ser Tyr Glu Glu
                805                 810                 815

Ser Val Tyr Asn Ser Gly Arg Lys Gly Pro Gly Pro Pro Ser Ser Asp
            820                 825                 830

Ala Ser Thr Ala Ala Pro Pro Tyr Thr Asn Glu Gln Ala Tyr Gln Met
        835                 840                 845

Leu Leu Ala Leu Ala Arg Leu Asp Ala Glu Gln Arg Ala Gln Gln Asn
    850                 855                 860

Gly Thr Asp Ser Leu Asp Gly Arg Thr Gly Thr Gln Asp Lys Gly Gln
865                 870                 875                 880

Lys Pro Asn Leu Leu Asp Arg Leu Arg His Arg Lys Asn Gly Tyr Arg
                885                 890                 895

His Leu Lys Asp Ser Asp Glu Glu Glu Asn Val
            900                 905
```

<210> SEQ ID NO 28
<211> LENGTH: 2724
<212> TYPE: DNA

<213> ORGANISM: Human cytomegalovirus

<400> SEQUENCE: 28

```
atggaatcca ggatctggtg cctggtagtc tgcgttaact tgtgtatcgt ctgtctgggt     60
gctgcggttt cctcatcttc tactcgtgga acttctgcta ctcacagtca ccattcctct    120
catacgacgt ctgctgctca ctctcgatcc ggttcagtct ctcaacgcgt aacttcttcc    180
caaacggtca gccatggtgt taacgagacc atctacaaca ctaccctcaa gtacggagat    240
gtggtggggg tcaataccac caagtacccc tatcgcgtgt gttctatggc ccagggtacg    300
gatcttattc gctttgaacg taatatcgtc tgcacctcga tgaagcccat caatgaagac    360
ctggacgagg gcatcatggt ggtctacaaa cgcaacatcg tcgcgcacac ctttaaggta    420
cgagtctacc agaaggtttt gacgtttcgt cgtagctacg cttacatcca caccacttat    480
ctgctgggca gcaacacgga atacgtggcg cctcctatgt gggagattca tcatatcaac    540
agccacagtc agtgctacag ttcctacagc cgcgttatag caggcacggt tttcgtggct    600
tatcataggg acagctatga aaacaaaacc atgcaattaa tgcccgacga ttattccaac    660
acccacagta cccgttacgt gacggtcaag gatcaatggc acagccgcgg cagcacctgg    720
ctctatcgtg agacctgtaa tctgaattgt atggtgacca tcactactgc gcgctccaaa    780
tatccttatc atttttcgc cacttccacg ggtgacgtgg ttgacatttc tcctttctac    840
aacggaacca atcgcaatgc cagctacttt ggagaaaacg ccgacaagtt tttcattttt    900
ccgaactaca ctatcgtctc cgactttgga agaccgaatt ctgcgttaga gacccacagg    960
ttggtggctt ttcttgaacg tgcggactcg gtgatctcct gggatataca ggacgaaaag   1020
aatgtcactt gtcaactcac tttctgggaa gcctcggaac gcaccattcg ttccgaagcc   1080
gaggactcgt atcacttttc ttctgccaaa atgaccgcca ctttcttatc taagaagcaa   1140
gaggtgaaca tgtccgactc tgcgctggac tgcgtacgtg atgaggctat aaataagtta   1200
cagcagattt tcaatacttc atacaatcaa acatatgaaa aatatggaaa cgtgtccgtc   1260
tttgaaacca ctggtggttt ggtagtgttc tggcaaggta tcaagcaaaa atctctggtg   1320
gaactcgaac gtttggccaa ccgctccagt ctgaatctta ctcataatag aaccaaaaga   1380
agtacagatg gcaacaatgc aactcattta tccaacatgg aatcggtgca caatctggtc   1440
tacgcccagc tgcagttcac ctatgacacg ttgcgcggtt acatcaaccg ggcgctggcg   1500
caaatcgcag aagcctggtg tgtggatcaa cggcgcaccc tagaggtctt caaggaactc   1560
agcaagatca acccgtcagc cattctctcg gccatttaca acaaaccgat tgccgcgcgt   1620
ttcatgggtg atgtcttggg cctggccagc tgcgtgacca tcaaccaaac cagcgtcaag   1680
gtgctgcgtg atatgaacgt gaaggagtcg ccaggacgct gctactcacg acccgtggtc   1740
atctttaatt tcgccaacag ctcgtacgtg cagtacggtc aactgggcga ggacaacgaa   1800
atcctgttgg gcaaccaccg cactgaggaa tgtcagcttc ccagcctcaa gatcttcatc   1860
gccgggaact cggcctacga gtacgtggac tacctcttca aacgcatgat tgacctcagc   1920
agtatctcca ccgtcgacag catgatcgcc ctggatatcg acccgctgga aaataccgac   1980
ttcagggtac tggaacttta ctcgcagaaa gagctgcgtt ccagcaacgt ttttgacctc   2040
gaagagatca tgcgcgaatt caactcgtac aagcagcggg taaagtacgt ggaggacaag   2100
gtagtcgacc cgctaccgcc ctacctcaag ggtctggacg acctcatgag cggcctgggc   2160
gccgcgggaa aggccgttgg cgtagccatt ggggccgtgg gtggcgcggt ggcctccgtg   2220
gtcgaaggcg ttgccacctt cctcaaaaac cccttcggag cgttcaccat catcctcgtg   2280
```

-continued

```
gccatagctg tagtcattat cacttatttg atctatactc gacagcggcg tttgtgcacg   2340

cagccgctgc agaacctctt tccctatctg gtgtccgccg acgggaccac cgtgacgtcg   2400

ggcagcacca aagacacgtc gttacaggct ccgccttcct acgaggaaag tgtttataat   2460

tctggtcgca aaggaccggg accaccgtcg tctgatgcat ccacggcggc tccgccttac   2520

accaacgagc aggcttacca gatgcttctg gccctggccc gtctggacgc agagcagcga   2580

gcgcagcaga acggtacaga ttctttggac ggacggactg gcacgcagga caagggacag   2640

aagcccaacc tactagaccg actgcgacat cgcaaaaacg gctaccgaca cttgaaagac   2700

tctgacgaag aagagaacgt ctga                                          2724
```

IMMUNOGENIC PEPTIDE

INCORPORATION BY REFERENCE OF MATERIAL SUBMITTED ELECTRONICALLY

This application contains, as a separate part of the disclosure, a Sequence Listing in computer-readable form (filename: 59323_Seqlisting.txt; 51,989 bytes; created Jun. 9, 2023), which is incorporated by reference in its entirety.

FIELD OF THE INVENTION

The invention relates to a human herpesvirus immunogenic peptide comprising a novel antigenic domain (AD) of glycoprotein B, termed AD-6. The invention also relates to a nucleic acid sequence encoding said immunogenic peptide and an inhibitor that binds to said immunogenic peptide. Also provided are an immunogenic composition, a pharmaceutical composition and a vaccine comprising said immunogenic peptide, nucleic acid sequence or inhibitor, and methods of treating or preventing a human herpesvirus infection.

BACKGROUND TO THE INVENTION

Human herpesviruses can establish lifelong latent infections, and over 50 percent of the world's population are infected by such viruses. Reactivations of herpesvirus infection are usually controlled by a competent immune system; however, in persons with compromised or immature immune systems (e.g. immunosuppressed transplant patients, neonates or young children) herpesviruses can cause more serious disease and substantial morbidity is seen in multiple such patient populations. For example, the herpesvirus human cytomegalovirus (HCMV) is a leading cause of disease in congenital infection and immunosuppressed transplant patients and is also the most common viral cause of sensorineural hearing loss.

Treatment of infections caused by herpesviruses typically involves the use of systemic antiviral treatment, often administered orally or parenterally if there is a risk of disseminated or severe disease. For example, the main strategy for treating HCMV infections is the use of the nucleoside analogue antiviral drug ganciclovir (GCV) or its oral prodrug valganciclovir. Although GCV is effective at inhibiting HCMV DNA replication, it is associated with significant haematological and nephrological toxicity and there is increasing antiviral resistance to GCV. Alternative antivirals include Foscavir, which is given to individuals with GCV-resistant HCMV, but this also has notable nephrotoxicity. Another antiviral drug called letermovir has recently been licensed for prophylactic use immediately after stem cell transplant. Limitations of antiviral treatment alongside the financial and healthcare burden associated with HCMV infection has led the US Institute of Medicine to define HCMV as one of the 3 viral pathogens with the highest priority for vaccine and new therapeutic interventions.

One alternative treatment for herpesvirus infections is the use of immunoglobulin from seropositive individuals (cytomegalovirus immune globulin, CMVIG) to increase the immune response against HCMV. However, this treatment does not appear to work in all HCMV patient populations, for example paediatric lung transplant recipients.

Vaccines have been licensed for the prevention of certain herpesviruses, such as varicella zoster virus (VZV). However, there are no vaccines currently licensed for the prevention of other herpesviruses such as HCMV.

A candidate vaccine against HCMV that has recently been investigated is a composition of recombinant HCMV glycoprotein B (gB) with MF59 adjuvant. The gB protein elicits a strong humoral immune response in humans, although the majority of anti-gB antibodies produced are non-neutralising. Neutralising antibodies are the focus of conventional antibody-based vaccine research since they are expected to significantly reduce viral infectivity, whereas non-neutralising antibodies are typically not considered the most desirable response for protection against viral pathogens. In three patient populations (young mothers, Pass et al. 1999, J Infect Dis 180(4) 970-5; solid organ transplant recipients, Griffiths et al. 2011 Lancet 377 1256-63; and adolescent girls, Bernstein et al. 2016, Vaccine 34(3) 313-9) the gB with MF59 adjuvant candidate vaccine has been shown to be safe, immunogenic and generally well tolerated. However, with only approximately 40 to 50 percent efficacy or less the protection is not sufficient for licensing as an effective vaccine.

Thus, there is a need in the art for vaccines and treatments that induce an effective immune response against human herpesviruses.

SUMMARY OF THE INVENTION

The present inventors have surprisingly identified a protective antibody response to a novel antigenic domain, termed antigenic domain (AD)-6, of HCMV gB. This antibody response is present in seronegative individuals vaccinated with recombinant HCMV gB protein but is rarely detected in seropositive (i.e. naturally infected) individuals. Surprisingly, the anti-AD-6 antibody response identified by the present inventors is capable of reducing the cell-to-cell spread of HCMV but is not a classical neutralising antibody. An immunogenic peptide that presents AD-6 to the immune system (e.g. in the context of an AD-6 subunit vaccine), particularly in the absence of other ADs of gB, has the potential to both focus the humoral response against AD-6 and prevent competing and potentially deleterious responses against other gB domains (e.g. other known ADs such as AD1-5). In other words, this approach is considered to be advantageous in promoting seronegative vaccine recipients to develop a robust antibody response against AD6. Furthermore, without wishing to be bound by theory, it is considered that such an immunogenic peptide will avoid the potential issue of original 'antigenic sin' that is seen with the candidate gB vaccine comprising recombinant HCMV gB and MF59 adjuvant in HCMV seropositive patients. This may be sufficient to improve the efficacy of a gB-based vaccine that can be utilised in both seronegative and seropositive individuals. Thus, the present invention is predicated upon the identification of a novel antigenic domain of gB that is considered to be effective for the prevention and treatment of herpesvirus infection.

In one aspect, the invention provides a human herpesvirus immunogenic peptide comprising SEQ ID NO: 7, SEQ ID NO: 9 or SEQ ID NO: 11, or a sequence having at least 75% (suitably, at least 80%, at least 85%, at least 90%, at least 95%, at least 96%, at least 97%, at least 98% or at least 99%) identity thereto, or an immunogenic fragment thereof.

In some embodiments, the human herpesvirus immunogenic peptide comprises SEQ ID NO: 7, a sequence having at least 75% (suitably, at least 80%, at least 85%, at least 90%, at least 95%, at least 96%, at least 97%, at least 98% or at least 99%) identity thereto, or an immunogenic fragment thereof.

In some embodiments, the human herpesvirus immunogenic peptide comprises SEQ ID NO: 9, a sequence having at least 75% (suitably, at least 80%, at least 85%, at least 90%, at least 95%, at least 96%, at least 97%, at least 98% or at least 99%) identity thereto, or an immunogenic fragment thereof.

In some embodiments, the human herpesvirus immunogenic peptide comprises SEQ ID NO: 11, a sequence having at least 75% (suitably, at least 80%, at least 85%, at least 90%, at least 95%, at least 96%, at least 97%, at least 98% or at least 99%) identity thereto, or an immunogenic fragment thereof.

In a further aspect, the invention provides an inhibitor of human herpesvirus glycoprotein-B which is capable of binding to human herpesvirus glycoprotein-B on the surface of a cell.

In some embodiments, said inhibitor binds within SEQ ID NO: 7, SEQ ID NO: 9 or SEQ ID NO: 11, or a sequence having at least 75% identity thereto, or a fragment thereof.

In a further aspect, the invention provides an inhibitor of human herpesvirus glycoprotein-B which is capable of binding to human herpesvirus glycoprotein-B, wherein the inhibitor binds within SEQ ID NO: 7, SEQ ID NO: 9 or SEQ ID NO: 11, or a sequence having at least 75% identity thereto, or a fragment thereof.

In some embodiments, said sequence has at least 80% identity to SEQ ID NO: 7, to SEQ ID NO: 9 or to SEQ ID NO: 11.

In some embodiments, said immunogenic fragment or said fragment is about 47 or fewer amino acids in length.

In some embodiments, said immunogenic fragment or said fragment is selected from SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 or SEQ ID NO: 26, or a variant thereof having one, two or three amino acid substitutions and/or having one, two or three amino acid deletions at the N- or C-terminus.

In some embodiments, said immunogenic fragment or said fragment is SEQ ID NO: 25 or SEQ ID NO: 26 or a variant thereof having one, two or three amino acid substitutions and/or having one, two or three amino acid deletions at the N- or C-terminus.

In some embodiments, said human herpesvirus is human cytomegalovirus (HCMV), herpes simplex virus-1 (HSV-1), or Epstein-Barr virus (EBV)

In some embodiments, said human herpesvirus is HCMV.

In some embodiments, said inhibitor binds within any one of SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 or SEQ ID NO: 26, or a fragment thereof, or a variant thereof having one, two or three amino acid substitutions and/or having one, two or three amino acid deletions at the N- and/or C-terminus.

In some embodiments, said inhibitor binds within SEQ ID NO: 25 or SEQ ID NO: 26, or a variant thereof having one, two or three amino acid substitutions and/or having one, two or three amino acid deletions at the N- or C-terminus.

In some embodiments, said inhibitor is selected from an antibody, an Ig fusion protein, a polypeptide, a peptide, a polynucleotide, a small molecule, a non-antibody scaffold, an aptamer, or combinations thereof.

In some embodiments, said inhibitor is an antibody.

In some embodiments, said antibody is a monoclonal antibody, a humanised antibody, a single-chain antibody, or an antibody fragment.

In a further aspect, the invention provides a nucleic acid sequence encoding the human herpesvirus immunogenic peptide of the invention.

In a further aspect, the invention provides a vector comprising the nucleic acid sequence of the invention.

In a further aspect, the invention provides an immunogenic composition comprising a human herpesvirus immunogenic peptide of the invention.

In a further aspect, the invention provides an immunogenic composition comprising a nucleic acid sequence of the invention or a vector of the invention.

In a further aspect, the invention provides a pharmaceutical composition comprising an inhibitor of the invention.

In a further aspect, the invention provides a vaccine comprising a human herpesvirus immunogenic peptide of the invention.

In a further aspect, the invention provides a vaccine comprising a nucleic acid sequence of the invention or a vector of the invention.

In a further aspect, the invention provides a vaccine comprising an inhibitor of the invention.

In a further aspect, the invention provides an immunogenic composition comprising a human herpesvirus immunogenic peptide of the invention for use in the treatment or prevention of human herpesvirus infection in a subject.

In a further aspect, the invention provides an immunogenic composition comprising a nucleic acid sequence of the invention or a vector of the invention for use in the treatment or prevention of human herpesvirus infection in a subject.

In a further aspect, the invention provides a pharmaceutical composition comprising an inhibitor of the invention for use in the treatment or prevention of human herpesvirus infection in a subject.

In a further aspect, the invention provides a vaccine comprising a human herpesvirus immunogenic peptide of the invention for use in the treatment or prevention of human herpesvirus infection in a subject.

In a further aspect, the invention provides a vaccine comprising a nucleic acid sequence of the invention or a vector of the invention for use in the treatment or prevention of human herpesvirus infection in a subject.

In a further aspect, the invention provides a vaccine comprising an inhibitor of the invention for use in the treatment or prevention of human herpesvirus infection in a subject.

In a further aspect, the invention provides an inhibitor of the invention for use in the treatment or prevention of human herpesvirus infection in a subject.

In some embodiments, the subject is:

a) an individual awaiting a solid organ transplant;

b) a solid organ transplant recipient;

c) a woman of childbearing age;

d) a pregnant woman; and/or e) a child.

In some embodiments, the cell-to-cell spread of the human herpesvirus is inhibited.

In some embodiments, the immunogenic composition, pharmaceutical composition, vaccine or inhibitor is for use in the prevention of human herpesvirus infection in the subject.

In some embodiments, the human herpesvirus is human cytomegalovirus (HCMV), herpes simplex virus-1 (HSV-1), or Epstein-Barr virus (EBV)

In some embodiments, the human herpesvirus is HCMV.

In some embodiments, the immunogenic composition, pharmaceutical composition, vaccine or inhibitor is administered to the subject in combination with at least one further pharmaceutically active agent.

In some embodiments, the at least one further pharmaceutically active agent is selected from an antiviral, a herpesvirus vaccine, an immunostimulatory cytokine, a checkpoint inhibitor, TCR-gene-engineered T cells, activators of innate immunity, monoclonal or bispecific antibodies, CAR cells, soluble T cell receptors, or any combination thereof.

In some embodiments, the immunogenic composition, pharmaceutical composition, vaccine or inhibitor is administered simultaneously, sequentially or separately with the at least one further pharmaceutically active agent.

DETAILED DESCRIPTION OF THE INVENTION

Immunogenic Peptide

Figure 1:
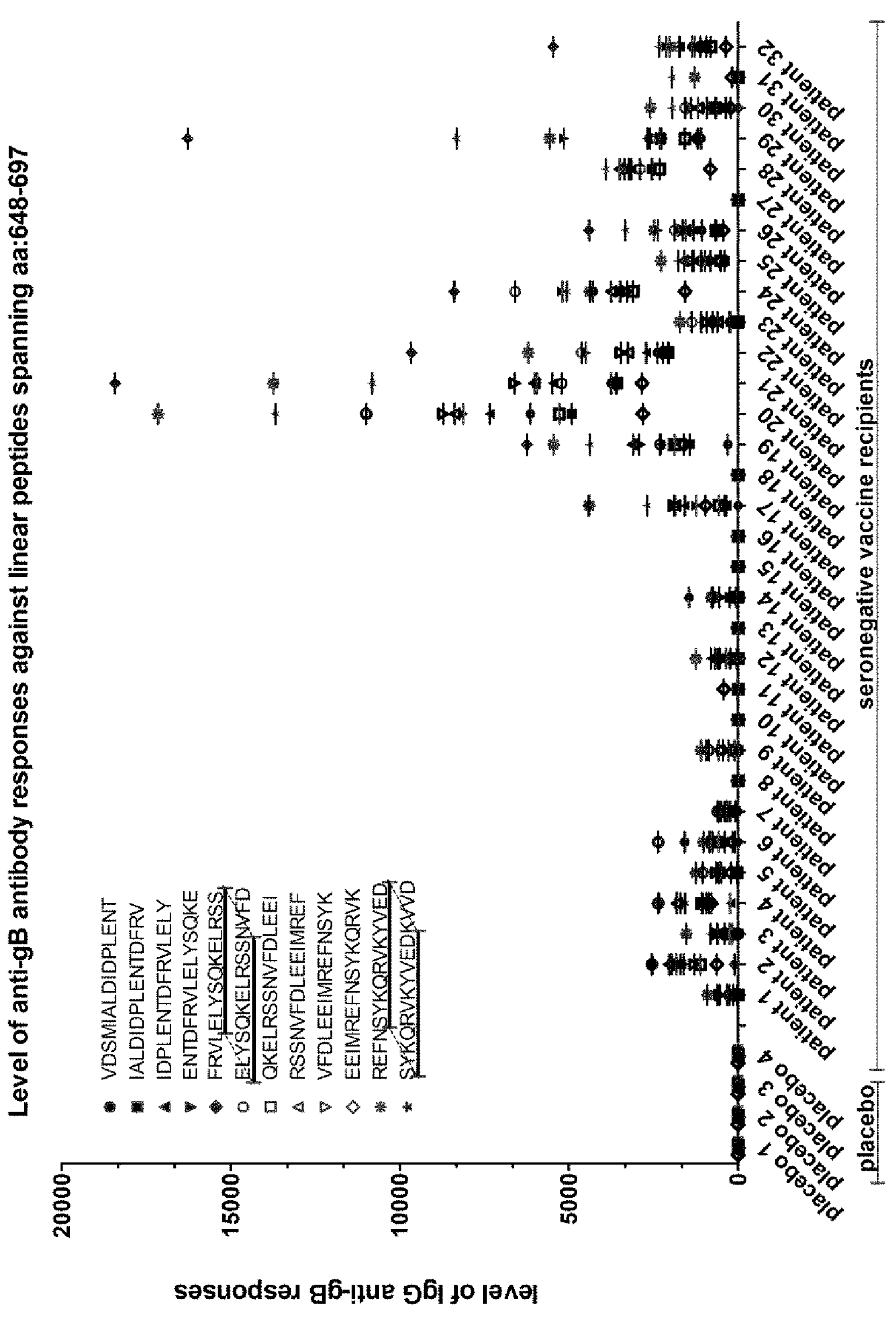
FIG. 1: Level of anti-gB antibody responses against linear peptides spanning aa648:697

The Herpesvirus family contains over 100 known viruses. There are nine herpesviruses that infect humans. Such human herpesviruses include herpes simplex virus-1 (HSV-1), Epstein-Barr virus (EBV) and human cytomegalovirus (HCMV).

Herpesviruses are double-stranded DNA enveloped viruses that can grow both cell-free and cell-associated. The viral life cycle involves the following major steps: viral attachment and entry into the host cell, viral gene expression, viral genome replication, virion assembly, and encapsidation and viral egress by exocytosis. Herpesviruses encode many viral glycoproteins, and many of these are critical for viral entry into the cell. Herpesvirus glycoprotein B (gB), a class III viral fusogen, is essential for viral entry into all host cell types and mediates the fusion of the viral envelope with the host cell membrane during entry and cell spread. The gB protein therefore has pre- and post-fusion conformations.

gB is the most highly conserved of all herpesvirus glycoproteins and occurs in all members of the herpesvirus family. The gB sequences of the human herpesviruses are known in the art.

An illustrative HCMV (strain AD169) gB amino acid sequence is provided by UniProtKB Accession Number P06473 and shown as SEQ ID NO: 1.

```
                                        SEQ ID NO: 1
MESRIWCLVVCVNLCIVCLGAAVSSSSTSHATSSTHNGSHTSRTTSAQTR

SVYSQHVTSSEAVSHRANETIYNTTLKYGDVVGVNTTKYPYRVCSMAQGT

DLIRFERNIICTSMKPINEDLDEGIMVVYKRNIVAHTFKVRVYQKVLTFR

RSYAYIYTTYLLGSNTEYVAPPMWEIHHINKFAQCYSSYSRVIGGTVFVA

YHRDSYENKTMQLIPDDYSNTHSTRYVTVKDQWHSRGSTWLYRETCNLNC

MLTITTARSKYPYHFFATSTGDVVYISPFYNGTNRNASYFGENADKFFIF

PNYTIVSDFGRPNAAPETHRLVAFLERADSVISWDIQDEKNVTCQLTFWE

ASERTIRSEAEDSYHFSSAKMTATFLSKKQEVNMSDSALDCVRDEAINKL

QQIFNTSYNQTYEKYGNVSVFETSGGLVVFWQGIKQKSLVELERLANRSS

LNITHRTRRSTSDNNTTHLSSMESVHNLVYAQLQFTYDTLRGYINRALAQ

IAEAWCVDQRRTLEVFKELSKINPSAILSAIYNKPIAARFMGDVLGLASC

VTINQTSVKVLRDMNVKESPGRCYSRPVVIFNFANSSYVQYGQLGEDNEI

LLGNHRTEECQLPSLKIFIAGNSAYEYVDYLFKRMIDLSSISTVDSMIAL

DIDPLENTDFRVLELYSQKELRSSNVFDLEEIMREFNSYKQRVKYVEDKV

VDPLPPYLKGLDDLMSGLGAAGKAVGVAIGAVGGAVASVVEGVATFLKNP

FGAFTIILVAIAVVIITYLIYTRQRRLCTQPLQNLFPYLVSADGTTVTSG
```

STKDTSLQAPPSYEESVYNSGRKGPGPPSSDASTAAPPYTNEQAYQMLLA

LARLDAEQRAQQNGTDSLDGQTGTQDKGQKPNLLDRLRHRKNGYRHLKDS

DEEENV

An illustrative HCMV (strain AD169) gB polynucleotide sequence is provided by EMBL-EBI ENA Number AAA46009.1 and shown as SEQ ID NO: 2.

SEQ ID NO: 2

ATGGAATCCAGGATCTGGTGCCTGGTAGTCTGCGTTAACCTGTGTATCGT

CTGTCTGGGTGCTGCGGTTTCCTCTTCTAGTACTTCCCATGCAACTTCTT

CTACTCACAATGGAAGCCATACTTCTCGTACGACGTCTGCTCAAACCCGG

TCAGTCTATTCTCAACACGTAACGTCTTCTGAAGCCGTCAGTCATAGAGC

CAACGAGACTATCTACAACACTACCCTCAAGTACGGAGATGTGGTGGGAG

TCAACACTACCAAGTACCCCTATCGCGTGTGTTCTATGGCCCAGGGTACG

GATCTTATTCGCTTTGAACGTAATATCATCTGCACCTCGATGAAGCCTAT

CAATGAAGACTTGGATGAGGGCATCATGGTGGTCTACAAGCGCAACATCG

TGGCGCACACCTTTAAGGTACGGGTCTACCAAAAGGTTTTGACGTTTCGT

CGTAGCTACGCTTACATCTACACCACTTATCTGCTGGGCAGCAATACGGA

ATACGTGGCGCCTCCTATGTGGGAGATTCATCACATCAACAAGTTTGCTC

AATGCTACAGTTCCTACAGCCGCGTTATAGGAGGCACGGTTTTCGTGGCA

TATCATAGGGACAGTTATGAAAACAAAACCATGCAATTAATTCCCGACGA

TTATTCCAACACCCACAGTACCCGTTACGTGACGGTCAAGGATCAGTGGC

ACAGCCGCGGCAGCACCTGGCTCTATCGTGAGACCTGTAATCTGAACTGT

ATGCTGACCATCACTACTGCGCGCTCCAAGTATCCTTATCATTTTTTTGC

AACTTCCACGGGTGATGTGGTTTACATTTCTCCTTTCTACAACGGAACCA

ATCGCAATGCCAGCTACTTTGGAGAAAACGCCGACAAGTTTTTCATTTTC

CCGAACTACACCATCGTTTCCGACTTTGGAAGACCCAACGCTGCGCCAGA

AACCCATAGGTTGGTGGCTTTTCTCGAACGTGCCGACTCGGTGATCTCTT

GGGATATACAGGACGAGAAGAATGTCACCTGCCAGCTCACCTTCTGGGAA

GCCTCGGAACGTACTATCCGTTCCGAAGCCGAAGACTCGTACCACTTTTC

TTCTGCCAAAATGACTGCAACTTTTCTGTCTAAGAAACAAGAAGTGAACA

TGTCCGACTCCGCGCTGGACTGCGTACGTGATGAGGCTATAAATAAGTTA

CAGCAGATTTTCAATACTTCATACAATCAAACATATGAAAAATACGGAAA

CGTGTCCGTCTTCGAAACCAGCGGCGGTCTGGTGGTGTTCTGGCAAGGCA

TCAAGCAAAAATCTTTGGTGGAATTGGAACGTTTGGCCAATCGATCCAGT

CTGAATATCACTCATAGGACCAGAAGAAGTACGAGTGACAATAATACAAC

TCATTTGTCCAGCATGGAATCGGTGCACAATCTGGTCTACGCCCAGCTGC

AGTTCACCTATGACACGTTGCGCGGTTACATCAACCGGGCGCTGGCGCAA

ATCGCAGAAGCCTGGTGTGTGGATCAACGGCGCACCCTAGAGGTCTTCAA

GGAACTCAGCAAGATCAACCCGTCAGCCATTCTCTCGGCCATTTACAACA

AACCGATTGCCGCGCGTTTCATGGGTGATGTCTTGGGCCTGGCCAGCTGC

GTGACCATCAACCAAACCAGCGTCAAGGTGCTGCGTGATATGAACGTGAA

GGAATCGCCAGGACGCTGCTACTCACGACCCGTGGTCATCTTTAATTTCG

CCAACAGCTCGTACGTGCAGTACGGTCAACTGGGCGAGGACAACGAAATC

CTGTTGGGCAACCACCGCACTGAGGAATGTCAGCTTCCCAGCCTCAAGAT

CTTCATCGCCGGGAACTCGGCCTACGAGTACGTGGACTACCTCTTCAAAC

GCATGATTGACCTCAGCAGTATCTCCACCGTCGACAGCATGATCGCCCTG

GATATCGACCCGCTGGAAAATACCGACTTCAGGGTACTGGAACTTTACTC

GCAGAAAGAGCTGCGTTCCAGCAACGTTTTTGACCTCGAAGAGATCATGC

GCGAATTCAACTCGTACAAGCAGCGGGTAAAGTACGTGGAGGACAAGGTA

GTCGACCCGCTACCGCCCTACCTCAAGGGTCTGGACGACCTCATGAGCGG

CCTGGGCGCCGCGGGAAAGGCCGTTGGCGTAGCCATTGGGGCCGTGGGTG

GCGCGGTGGCCTCCGTGGTCGAAGGCGTTGCCACCTTCCTCAAAAACCCC

TTCGGAGCCTTCACCATCATCCTCGTGGCCATAGCCGTAGTCATTATCAC

TTATTTGATCTATACTCGACAGCGGCGTCTGTGCACGCAGCCGCTGCAGA

ACCTCTTTCCCTATCTGGTGTCCGCCGACGGGACCACCGTGACGTCGGGC

AGCACCAAAGACACGTCGTTACAGGCTCCGCCTTCCTACGAGGAAAGTGT

TTATAATTCTGGTCGCAAAGGACCGGGACCACCGTCGTCTGATGCATCCA

CGGCGGCTCCGCCTTACACCAACGAGCAGGCTTACCAGATGCTTCTGGCC

CTGGCCCGTCTGGACGCAGAGCAGCGAGCGCAGCAGAACGGTACAGATTC

TTTGGACGGACAGACTGGCACGCAGGACAAGGGACAGAAGCCTAACCTGC

TAGACCGGCTGCGACATCGCAAAAACGGCTACAGACACTTGAAAGACTCC

GACGAAGAAGAGAACGTCTGA

A further illustrative HCMV (strain Merlin) gB amino acid sequence is provided by UniProtKB Accession Number F5HB53 and shown as SEQ ID NO: 27.

SEQ ID NO: 27

MESRIWCLVVCVNLCIVCLGAAVSSSSTRGTSATHSHHSSHTTSAAHSRS

GSVSQRVTSSQTVSHGVNETIYNTTLKYGDVVGVNTTKYPYRVCSMAQGT

DLIRFERNIVCTSMKPINEDLDEGIMVVYKRNIVAHTFKVRVYQKVLTFR

RSYAYIHTTYLLGSNTEYVAPPMWEIHHINSHSQCYSSYSRVIAGTVFVA

YHRDSYENKTMQLMPDDYSNTHSTRYVTVKDQWHSRGSTWLYRETCNLNC

MVTITTARSKYPYHFFATSTGDVVDISPFYNGTNRNASYFGENADKFFIF

PNYTIVSDFGRPNSALETHRLVAFLERADSVISWDIQDEKNVTCQLTFWE

ASERTIRSEAEDSYHFSSAKMTATFLSKKQEVNMSDSALDCVRDEAINKL

QQIFNTSYNQTYEKYGNVSVFETTGGLVVFWQGIKQKSLVELERLANRSS

LNLTHNRTKRSTDGNNATHLSNMESVHNLVYAQLQFTYDTLRGYINRALA

QIAEAWCVDQRRTLEVFKELSKINPSAILSAIYNKPIAARFMGDVLGLAS

CVTINQTSVKVLRDMNVKESPGRCYSRPVVIFNFANSSYVQYGQLGEDNE

ILLGNHRTEECQLPSLKIFIAGNSAYEYVDYLFKRMIDLSSISTVDSMIA

LDIDPLENTDFRVLELYSQKELRSSNVFDLEEIMREFNSYKQRVKYVEDK

VVDPLPPYLKGLDDLMSGLGAAGKAVGVAIGAVGGAVASVVEGVATFLKN

PFGAFTIILVAIAVVIITYLIYTRORRLCTQPLQNLFPYLVSADGTTVTS

-continued

GSTKDTSLQAPPSYEESVYNSGRKGPGPPSSDASTAAPPYTNEQAYQMLL

ALARLDAEQRAQQNGTDSLDGRTGTQDKGQKPNLLDRLRHRKNGYRHLKD

SDEEENV

A further illustrative HCMV (strain Merlin) gB polynucleotide sequence is provided by EMBL-EBI ENA Number AAR31620.1 and shown as SEQ ID NO: 28.

SEQ ID NO: 28

ATGGAATCCAGGATCTGGTGCCTGGTAGTCTGCGTTAACTTGTGTATCGT

CTGTCTGGGTGCTGCGGTTTCCTCATCTTCTACTCGTGGAACTTCTGCTA

CTCACAGTCACCATTCCTCTCATACGACGTCTGCTGCTCACTCTCGATCC

GGTTCAGTCTCTCAACGCGTAACTTCTTCCCAAACGGTCAGCCATGGTGT

TAACGAGACCATCTACAACACTACCCTCAAGTACGGAGATGTGGTGGGGG

TCAATACCACCAAGTACCCCTATCGCGTGTGTTCTATGGCCCAGGGTACG

GATCTTATTCGCTTTGAACGTAATATCGTCTGCACCTCGATGAAGCCCAT

CAATGAAGACCTGGACGAGGGCATCATGGTGGTCTACAAACGCAACATCG

TCGCGCACACCTTTAAGGTACGAGTCTACCAGAAGGTTTTGACGTTTCGT

CGTAGCTACGCTTACATCCACACCACTTATCTGCTGGGCAGCAACACGGA

ATACGTGGCGCCTCCTATGTGGGAGATTCATCATATCAACAGCCACAGTC

AGTGCTACAGTTCCTACAGCCGCGTTATAGCAGGCACGGTTTTCGTGGCT

TATCATAGGGACAGCTATGAAAACAAAACCATGCAATTAATGCCCGACGA

TTATTCCAACACCCACAGTACCCGTTACGTGACGGTCAAGGATCAATGGC

ACAGCCGCGGCAGCACCTGGCTCTATCGTGAGACCTGTAATCTGAATTGT

ATGGTGACCATCACTACTGCGCGCTCCAAATATCCTTATCATTTTTTCGC

CACTTCCACGGGTGACGTGGTTGACATTTCTCCTTTCTACAACGGAACCA

ATCGCAATGCCAGCTACTTTGGAGAAAACGCCGACAAGTTTTTCATTTTT

CCGAACTACACTATCGTCTCCGACTTTGGAAGACCGAATTCTGCGTTAGA

GACCCACAGGTTGGTGGCTTTTCTTGAACGTGCGGACTCGGTGATCTCCT

GGGATATACAGGACGAAAAGAATGTCACTTGTCAACTCACTTTCTGGGAA

GCCTCGGAACGCACCATTCGTTCCGAAGCCGAGGACTCGTATCACTTTTC

TTCTGCCAAAATGACCGCCACTTTCTTATCTAAGAAGCAAGAGGTGAACA

TGTCCGACTCTGCGCTGGACTGCGTACGTGATGAGGCTATAAATAAGTTA

CAGCAGATTTTCAATACTTCATACAATCAAACATATGAAAAATATGGAAA

CGTGTCCGTCTTTGAAACCACTGGTGGTTTGGTAGTGTTCTGGCAAGGTA

TCAAGCAAAAATCTCTGGTGGAACTCGAACGTTTGGCCAACCGCTCCAGT

CTGAATCTTACTCATAATAGAACCAAAAGAAGTACAGATGGCAACAATGC

AACTCATTTATCCAACATGGAATCGGTGCACAATCTGGTCTACGCCCAGC

TGCAGTTCACCTATGACACGTTGCGCGGTTACATCAACCGGGCGCTGGCG

CAAATCGCAGAAGCCTGGTGTGTGGATCAACGGCGCACCCTAGAGGTCTT

CAAGGAACTCAGCAAGATCAACCCGTCAGCCATTCTCTCGGCCATTTACA

ACAAACCGATTGCCGCGCGTTTCATGGGTGATGTCTTGGGCCTGGCCAGC

TGCGTGACCATCAACCAAACCAGCGTCAAGGTGCTGCGTGATATGAACGT

-continued

GAAGGAGTCGCCAGGACGCTGCTACTCACGACCCGTGGTCATCTTTAATT

TCGCCAACAGCTCGTACGTGCAGTACGGTCAACTGGGCGAGGACAACGAA

ATCCTGTTGGGCAACCACCGCACTGAGGAATGTCAGCTTCCCAGCCTCAA

GATCTTCATCGCCGGGAACTCGGCCTACGAGTACGTGGACTACCTCTTCA

AACGCATGATTGACCTCAGCAGTATCTCCACCGTCGACAGCATGATCGCC

CTGGATATCGACCCGCTGGAAAATACCGACTTCAGGGTACTGGAACTTTA

CTCGCAGAAAGAGCTGCGTTCCAGCAACGTTTTTGACCTCGAAGAGATCA

TGCGCGAATTCAACTCGTACAAGCAGCGGGTAAAGTACGTGGAGGACAAG

GTAGTCGACCCGCTACCGCCCTACCTCAAGGGTCTGGACGACCTCATGAG

CGGCCTGGGCGCCGCGGGAAAGGCCGTTGGCGTAGCCATTGGGGCCGTGG

GTGGCGCGGTGGCCTCCGTGGTCGAAGGCGTTGCCACCTTCCTCAAAAAC

CCCTTCGGAGCGTTCACCATCATCCTCGTGGCCATAGCTGTAGTCATTAT

CACTTATTTGATCTATACTCGACAGCGGCGTTTGTGCACGCAGCCGCTGC

AGAACCTCTTTCCCTATCTGGTGTCCGCCGACGGGACCACCGTGACGTCG

GGCAGCACCAAAGACACGTCGTTACAGGCTCCGCCTTCCTACGAGGAAAG

TGTTTATAATTCTGGTCGCAAAGGACCGGGACCACCGTCGTCTGATGCAT

CCACGGCGGCTCCGCCTTACACCAACGAGCAGGCTTACCAGATGCTTCTG

GCCCTGGCCCGTCTGGACGCAGAGCAGCGAGCGCAGCAGAACGGTACAGA

TTCTTTGGACGGACGGACTGGCACGCAGGACAAGGGACAGAAGCCCAACC

TACTAGACCGACTGCGACATCGCAAAAACGGCTACCGACACTTGAAAGAC

TCTGACGAAGAAGAGAACGTCTGA

An illustrative HSV-1 (strain KOS) gB amino acid sequence is provided by UniProtKB Accession Number P06437 and shown as SEQ ID NO: 3.

SEQ ID NO: 3

MHQGAPSWGRRWFVVWALLGLTLGVLVASAAPTSPGTPGVAAATQAANGG

PATPAPPPLGAAPTGDPKPKKNKKPKNPTPPRPAGDNATVAAGHATLREH

LRDIKAENTDANFYVCPPPTGATVVQFEQPRRCPTRPEGQNYTEGIAVVF

KENIAPYKFKATMYYKDVTVSQVWFGHRYSQFMGIFEDRAPVPFEEVIDK

INAKGVCRSTAKYVRNNLETTAFHRDDHETDMELKPANAATRTSRGWHTT

DLKYNPSRVEAFHRYGTTVNCIVEEVDARSVYPYDEFVLATGDFVYMSPF

YGYREGSHTEHTTYAADRFKQVDGFYARDLTTKARATAPTTRNLLTTPKF

TVAWDWVPKRPSVCTMTKWQEVDEMLRSEYGGSFRFSSDAISTTFTTNLT

EYPLSRVDLGDCIGKDARDAMDRIFARRYNATHIKVGQPQYYQANGGFLI

AYQPLLSNTLAELYVREHLREQSRKPPNPTPPPPGASANASVERIKTTSS

IEFARLQFTYNHIQRHVNDMLGRVAIAWCELQNHELTLWNEARKLNPNAI

ASVTVGRRVSARMLGDVMAVSTCVPVAADNVIVQNSMRISSRPGACYSRP

LVSFRYEDQGPLVEGQLGENNELRLTRDAIEPCTVGHRRYFTFGGGYVYF

EEYAYSHQLSRADITTVSTFIDLNITMLEDHEFVPLEVYTRHEIKDSGLL

DYTEVQRRNQLHDLRFADIDTVIHADANAAMFAGLGAFFEGMGDLGRAVG

KVVMGIVGGVVSAVSGVSSFMSNPFGALAVGLLVLAGLAAAFFAFRYVMR

-continued

LQSNPMKALYPLTTKELKNPTNPDASGEGEEGGDFDEAKLAEAREMIRYM

ALVSAMERTEHKAKKKGTSALLSAKVTDMVMRKRRNTNYTQVPNKDGDAD

EDDL

An illustrative HSV-1 (strain KOS) gB polynucleotide sequence is provided by EMBL-EBI ENA Number AAA45774.1 and shown as SEQ ID NO: 4.

SEQ ID NO: 4

ATGCACCAGGGCGCCCCCTCGTGGGGGCGCCGGTGGTTCGTCGTATGGGC

GCTCTTGGGGTTGACGCTGGGGGTCCTGGTGGCGTCGGCGGCTCCGACTT

CCCCCGGCACGCCTGGGGTCGCGGCCGCGACCCAGGCGGCGAACGGGGGC

CCTGCCACTCCGGCGCCGCCGCCCCTTGGCGCCGCCCCAACGGGGGACCC

GAAACCGAAGAAGAACAAAAAACCGAAAAACCCAACGCCACCACGCCCCG

CCGGCGACAACGCGACCGTCGCCGCGGGCCACGCCACCCTGCGCGAGCAC

CTGCGGGACATCAAGGCGGAGAACACCGATGCAAACTTTTACGTGTGCCC

ACCCCCCACGGGCGCCACGGTGGTGCAGTTCGAGCAGCCGCGCCGCTGCC

CGACCCGGCCCGAGGGTCAGAACTACACGGAGGGCATCGCGGTGGTCTTC

AAGGAGAACATCGCCCCGTACAAGTTCAAGGCCACCATGTACTACAAAGA

CGTCACCGTTTCGCAGGTGTGGTTCGGCCACCGCTACTCCCAGTTTATGG

GGATCTTTGAGGACCGCGCCCCCGTCCCCTTCGAGGAGGTGATCGACAAG

ATCAACGCCAAGGGGGTCTGTCGGTCCACGGCCAAGTACGTGCGCAACAA

CCTGGAGACCACCGCGTTTCACCGGGACGACCACGAGACCGACATGGAGC

TGAAACCGGCCAACGCCGCGACCCGCACGAGCCGGGGCTGGCACACCACC

GACCTCAAGTACAACCCCTCGCGGGTGGAGGCGTTCCACCGGTACGGGAC

GACGGTAAACTGCATCGTCGAGGAGGTGGACGCGCGCTCGGTGTACCCGT

ACGACGAGTTTGTGCTGGCGACTGGCGACTTTGTGTACATGTCCCCGTTT

TACGGCTACCGGGAGGGGTCGCACACCGAACACACCACGTACGCCGCCGA

CCGCTTCAAGCAGGTCGACGGCTTCTACGCGCGCGACCTCACCACCAAGG

CCCGGGCCACGGCGCCGACCACCCGGAACCTGCTCACGACCCCCAAGTTC

ACCGTGGCCTGGGACTGGGTGCCAAAGCGCCCGTCGGTCTGCACCATGAC

CAAGTGGCAGGAAGTGGACGAGATGCTGCGCTCCGAGTACGGCGGCTCCT

TCCGATTCTCCTCCGACGCCATATCCACCACCTTCACCACCAACCTGACC

GAGTACCCGCTCTCGCGCGTGGACCTGGGGGACTGCATCGGCAAGGACGC

CCGCGACGCCATGGACCGCATCTTCGCCCGCAGGTACAACGCGACGCACA

TCAAGGTGGGCCAGCCGCAGTACTACCAGGCCAATGGGGGCTTTCTGATC

GCGTACCAGCCCCTTCTCAGCAACACGCTCGCGGAGCTGTACGTGCGGGA

ACACCTCCGAGAGCAGAGCCGCAAGCCCCCAAACCCCACGCCCCCGCCGC

CCGGGGCCAGCGCCAACGCGTCCGTGGAGCGCATCAAGACCACCTCCTCC

ATCGAGTTCGCCCGGCTGCAGTTTACGTACAACCACATACAGCGCCATGT

CAACGATATGTTGGGCCGCGTTGCCATCGCGTGGTGCGAGCTACAGAATC

ACGAGCTGACCCTGTGGAACGAGGCCCGCAAGCTGAACCCCAACGCCATC

GCCTCGGTCACCGTGGGCCGGCGGGTGAGCGCGCGGATGCTCGGCGACGT

-continued

GATGGCCGTCTCCACGTGCGTGCCGGTCGCCGCGGACAACGTGATCGTCC

AAAACTCGATGCGCATCAGCTCGCGGCCCGGGGCCTGCTACAGCCGCCCC

CTGGTCAGCTTTCGGTACGAAGACCAGGGCCCGTTGGTCGAGGGGCAGCT

GGGGGAGAACAACGAGCTGCGGCTGACGCGCGATGCGATCGAGCCGTGCA

CCGTGGGACACCGGCGCTACTTCACCTTCGGTGGGGGCTACGTGTACTTC

GAGGAGTACGCGTACTCCCACCAGCTGAGCCGCGCCGACATCACCACCGT

CAGCACCTTCATCGACCTCAACATCACCATGCTGGAGGATCACGAGTTTG

TCCCCCTGGAGGTGTACACCCGCCACGAGATCAAGGACAGCGGCCTGCTG

GACTACACGGAGGTCCAGCGCCGCAACCAGCTGCACGACCTGCGCTTCGC

CGACATCGACACGGTCATCCACGCCGACGCCAACGCCGCCATGTTCGCGG

GCCTGGGCGCGTTCTTCGAGGGGATGGGCGACCTGGGGCGCGCGGTCGGC

AAGGTGGTGATGGGCATCGTGGGCGGCGTGGTATCGGCCGTGTCGGGCGT

GTCCTCCTTCATGTCCAACCCCTTTGGGGCGCTGGCCGTGGGTCTGTTGG

TCCTGGCCGGCCTGGCGGCGGCCTTCTTCGCCTTTCGTTACGTCATGCGG

CTGCAGAGCAACCCCATGAAGGCCCTGTACCCTCTAACCACCAAGGAGCT

CAAGAACCCCACCAACCCGGACGCGTCCGGGGAGGGCGAGGAGGGCGGCG

ACTTTGACGAGGCCAAGCTAGCCGAGGCCAGGGAGATGATACGGTACATG

GCCCTGGTGTCGGCCATGGAGCGCACGGAACACAAGGCCAAGAAGAAGGG

CACGAGCGCGCTGCTCAGCGCCAAGGTCACCGACATGGTCATGCGCAAGC

GCCGCAACACCAACTACACCCAAGTTCCCAACAAAGACGGTGACGCCGAC

GAGGACGACCTGTGA

An illustrative EBV (strain B958) gB amino acid sequence is provided by Uniprot Accession Number Q777130 and shown as SEQ ID NO: 5.

SEQ ID NO: 5

MTRRRVLSVVVLLAALACRLGAQTPEQPAPPATTVQPTATRQQTSFPFRV

CELSSHGDLFRFSSDIQCPSFGTRENHTEGLLMVFKDNIIPYSFKVRSYT

KIVTNILIYNGWYADSVTNRHEEKFSVDSYETDQMDTIYQCYNAVKMTKD

GLTRVYVDRDGVNITVNLKPTGGLANGVRRYASQTELYDAPGWLIWTYRT

RTTVNCLITDMMAKSNSPFDFFVTTTGQTVEMSPFYDGKNKETFHERADS

FHVRTNYKIVDYDNRGTNPQGERRAFLDKGTYTLSWKLENRTAYCPLQHW

QTFDSTIATETGKSIHFVTDEGTSSFVTNTTVGIELPDAFKCIEEQVNKT

MHEKYEAVQDRYTKGQEAITYFITSGGLLLAWLPLTPRSLATVKNLTELT

TPTSSPPSSPSPPAPSAARGSTPAAVLRRRRRDAGNATTPVPPTAPGKSL

GTLNNPATVQIQFAYDSLRRQINRMLGDLARAWCLEQKRQNMVLRELTKI

NPTTVMSSIYGKAVAAKRLGDVISVSQCVPVNQATVTLRKSMRVPGSETM

CYSRPLVSFSFINDTKTYEGQLGTDNEIFLTKKMTEVCQATSQYYFQSGN

EIHVYNDYHHFKTIELDGIATLQTFISLNTSLIENIDFASLELYSRDEQR

ASNVFDLEGIFREYNFQAQNIAGLRKDLDNAVSNGRNQFVDGLGELMDSL

GSVGQSITNLVSTVGGLFSSLVSGFISFFKNPFGGMLILVLVAGVVILVI

SLTRRTRQMSQQPVQMLYPGIDELAQQHASGEGPGINPISKTELQAIMLA

-continued

LHEQNQEQKRAAQRAAGPSVASRALQAARDRFPGLRRRRYHDPETAAALL

GEAETEF

An illustrative EBV (strain B958) gB polynucleotide sequence is provided by EMBL-EBI ENA Number CAA24806.1 and shown as SEQ ID NO: 6.

SEQ ID NO: 6

ATGACTCGGCGTAGGGTGCTAAGCGTGGTCGTGCTGCTAGCCGCCCTGGC

GTGCCGTCTCGGTGCGCAGACCCCAGAGCAGCCCGCACCCCCCGCCACCA

CGGTGCAGCCTACCGCCACGCGTCAGCAAACCAGCTTTCCTTTCCGAGTC

TGCGAGCTCTCCAGCCACGGCGACCTGTTCCGCTTCTCCTCGGACATCCA

GTGTCCCTCGTTTGGCACGCGGGAGAATCACACGGAGGGCCTGTTGATGG

TGTTTAAAGACAACATTATTCCCTACTCGTTTAAGGTCCGCTCCTACACC

AAGATAGTGACCAACATTCTCATCTACAATGGCTGGTACGCGGACTCCGT

GACCAACCGGCACGAGGAGAAGTTCTCCGTTGACAGCTACGAAACTGACC

AGATGGATACCATCTACCAGTGCTACAACGCGGTCAAGATGACAAAAGAT

GGGCTGACGCGCGTGTATGTAGACCGCGACGGAGTTAACATCACCGTCAA

CCTAAAGCCCACCGGGGGCCTGGCCAACGGGGTGCGCCGCTACGCCAGCC

AGACGGAGCTCTATGACGCCCCCGGGTGGTTGATATGGACTTACAGAACA

AGAACTACCGTCAACTGCCTGATAACTGACATGATGGCCAAGTCCAACAG

CCCCTTCGACTTCTTTGTGACCACCACCGGGCAGACTGTGGAAATGTCCC

CTTTCTATGACGGGAAAAATAAGGAAACCTTCCATGAGCGGGCAGACTCC

TTCCACGTGAGAACTAACTACAAGATAGTGGACTACGACAACCGAGGGAC

GAACCCGCAAGGCGAACGCCGAGCCTTCCTGGACAAGGGCACTTACACGC

TATCTTGGAAGCTCGAGAACAGGACAGCCTACTGCCCGCTTCAACACTGG

CAAACCTTTGACTCGACCATCGCCACAGAAACAGGGAAGTCAATACATTT

TGTGACTGACGAGGGCACCTCTAGCTTCGTGACCAACACAACCGTGGGCA

TAGAGCTCCCGGACGCCTTCAAGTGCATCGAAGAGCAGGTGAACAAGACC

ATGCATGAGAAGTACGAGGCCGTCCAGGATCGTTACACGAAGGGCCAGGA

AGCCATTACATATTTTATAACGAGCGGAGGATTGTTATTAGCTTGGCTAC

CTCTGACCCCGCGCTCGTTGGCCACCGTCAAGAACCTGACGGAGCTTACC

ACTCCGACTTCCTCACCCCCCAGCAGTCCATCGCCCCCAGCCCCATCCGC

GGCCCGCGGGAGCACCCCCGCCGCCGTTCTGAGGCGTCGGAGGCGGGATG

CGGGGAACGCCACCACACCGGTGCCCCCCACGGCCCCCGGGAAGTCCCTG

GGCACCCTCAACAATCCCGCCACCGTCCAGATCCAATTTGCCTACGACTC

CCTGCGCCGCCAGATCAACCGCATGCTGGGAGACCTTGCGCGGGCCTGGT

GCCTGGAGCAGAAGAGGCAGAACATGGTGCTGAGAGAACTAACCAAGATT

AATCCAACCACCGTCATGTCCAGCATCTACGGTAAGGCGGTGGCGGCCAA

GCGCCTGGGGGATGTCATCTCAGTCTCCCAGTGCGTGCCCGTTAACCAGG

CCACCGTCACCCTGCGCAAGAGCATGAGGGTCCCTGGCTCCGAGACCATG

TGCTACTCGCGCCCCCTGGTGTCCTTCAGCTTTATCAACGACACCAAGAC

CTACGAGGGACAGCTGGGCACCGACAACGAGATCTTCCTCACAAAAAAGA

-continued

TGACGGAGGTGTGCCAGGCGACCAGCCAGTACTACTTCCAGTCCGGCAAC

GAGATCCACGTCTACAACGACTACCACCACTTTAAAACCATCGAGCTGGA

CGGCATTGCCACCCTGCAGACCTTCATCTCACTAAACACCTCCCTCATCG

AGAACATTGACTTTGCCTCCCTGGAGCTGTACTCACGGGACGAACAGCGT

GCCTCCAACGTCTTTGACCTGGAGGGCATCTTCCGGGAGTACAACTTCCA

GGCGCAAAACATCGCCGGCCTGCGGAAGGATTTGGACAATGCAGTGTCAA

ACGGAAGAAATCAATTCGTGGACGGCCTGGGGGAACTTATGGACAGTCTG

GGTAGCGTGGGTCAGTCCATCACCAACCTAGTCAGCACGGTGGGGGGTTT

GTTTAGCAGCCTGGTCTCTGGTTTCATCTCCTTCTTCAAAAACCCCTTCG

GCGGCATGCTCATTCTGGTCCTGGTGGCGGGGGTGGTGATCCTGGTTATT

TCCCTCACGAGGCGCACGCGCCAGATGTCGCAGCAGCCGGTGCAGATGCT

CTACCCCGGGATCGACGAGCTCGCTCAGCAACATGCCTCTGGTGAGGGTC

CAGGCATTAATCCCATTAGTAAGACAGAATTACAAGCCATCATGTTAGCG

CTGCATGAGCAAAACCAGGAGCAAAAGAGAGCAGCTCAGAGGGCGGCCGG

ACCCTCAGTGGCCAGCAGAGCATTGCAGGCAGCCAGGGACCGTTTTCCAG

GCCTACGCAGAAGACGCTATCACGATCCAGAGACCGCCGCCGCACTGCTT

GGGGAGGCAGAGACTGAGTTTTA gB is a large, glycosylated protein of approximately 900 amino acids. The crystal structure of the gB ectodomain from several herpesviruses (including HSV-1, EBV and HCMV) has been solved as a trimer in its post-fusion conformation, revealing five structural domains (Domains I-V) (Heldwein E E et al. (2006), Science, 313:217-220; Backovic M et al. (2009), Proc. Natl. Acad. Sci. U.S.A, 106:2880-2885; and Burke, HG and Heldwein, EE (2015), PLoS Pathogens, 11(10):e1005300). Domain III (also known as the core domain) is a long helix that forms a central triple coiled coil within gB trimer, whilst Domain V spans almost the full length of the gB ectodomain and fits into a groove formed by Domain III and Domain I of the other two gB monomers within the trimer structure. The pre-fusion conformation of a herpesvirus gB has not yet been characterised by crystallography. Despite the relatively low sequence identity between the various human herpesvirus gBs, the crystal structures of the gB ectodomains are very similar.

The major antigenic domains (AD) of HSV-1 and HCMV gB during natural infection have been identified, and in both cases multiple competing ADs exist. The five major ADs identified in HCMV gB protein are: AD-1, AD-2, AD-3, AD-4 and AD-5. Of these, AD-2, AD-4 and AD-5, have been considered the most promising candidates for production of therapeutic immunoglobulins (Burke, HG and Heldwein, EE (2015), PLoS Pathogens, 11(10):e1005300). None of AD-1 to AD-5 are located within Domain III or Domain V of HCMV gB, and no antibodies against Domains III or V of HCMV gB have been previously isolated.

As used herein, the term "antigenic domain (AD)" means a target sequence or structure within an antigen, e.g. within gB, that is recognised by antibodies. Thus, an antigenic domain contains a limited number of neighbouring epitopes recognised by antibodies, for example, in infected or vaccinated individuals.

gB is the dominant antigenic protein within the herpesvirus envelope and elicits a strong humoral immune response in humans, although the majority of anti-gB antibodies are non-neutralising and target the immunodominant antigenic site AD-1. Neutralising antibodies are the focus of conventional antibody-based vaccine research since they are expected to significantly reduce viral infectivity, whereas non-neutralising antibodies are typically not thought to offer significant protection against viral pathogens. The lack of neutralising antibodies to gB has been attributed to the diversion of the immune response towards production of non-neutralising antibodies at multiple competing antigenic sites by herpesviruses. This can be achieved, for example, by glycan shielding of certain epitopes to protect them from the immune system—whilst HCMV gB is heavily glycosylated, there is limited glycosylation of Domain IV which contains the immunodominant site AD-1.

The present inventors have surprisingly identified a novel AD of gB, referred to as "AD-6" or "AD6" herein. This novel AD is recognised by antibodies in vaccinated seronegative individuals, but only rarely in vaccinated seropositive (i.e. naturally infected) individuals. In some embodiments, AD-6 maps to amino acids 647 to 694 of SEQ ID NO: 1 or to amino acids 648 to 695 of SEQ ID NO: 27, and so spans two structural domains, Domain III and Domain V, of HCMV gB.

An immunogenic peptide of the invention that presents AD-6 to the immune system (e.g. in the context of an AD-6 subunit vaccine) has the potential to be effective, particularly if the presentation of other ADs of gB is absent. This would allow the immune system to focus on generating humoral responses against the novel AD-6 epitope rather than potential "decoy" epitopes (e.g. AD-1, AD-2, AD-3, AD-4 and/or AD-5) present in gB, i.e. to avoid the issue of original 'antigenic sin' that is seen in HCMV seropositive patients with the candidate gB vaccine comprising recombinant HCMV gB and MF59 adjuvant (Baraniak et al. 2019 J. Infect. Dis. 220(2) 228-232). Thus, an immunogenic peptide that presents AD-6 to the immune system (e.g. in the context of an AD-6 subunit vaccine) would both focus the humoral response against AD-6 and prevent deleterious response against other gB domains. This may be sufficient to improve the efficacy of a gB-based vaccine.

The identification of a virus having a protein with an AD-6 domain can be performed using methods known in the art. For example, a suitable virus can be identified by the ability of an anti-AD-6 antibody to prevent virus infection and replication in vitro, for example using an assay as described herein (see Example 2). The assay may be performed in any cell type that supports lytic HCMV replication (e.g. HFF, ARPE, U373, dendritic cell, macrophage, endothelial cell). It is within the capabilities of the skilled person to select a suitable cell type.

The identification of an AD-6 domain can be performed using methods known in the art. Suitably, the ability of an anti-AD-6 antibody to bind the candidate domain (e.g. a candidate gB protein) may be determined using an isolated candidate domain (e.g. recombinant protein). Suitable methods for determining binding will be known to those of skill in the art. For example, binding may be assessed by ELISA, flow cytometry, immunohistochemistry, Western blotting and surface plasmon resonance. Preferably, binding may be assessed by ELISA. An anti-AD-6 antibody may be generated using methods known in the art, for example as described herein (see Example 2). It is within the ambit of the skilled person to select and implement a suitable assay to determine if a candidate domain is an AD-6 domain.

An illustrative HCMV gB AD-6 amino acid sequence is shown as SEQ ID NO: 7.

SEQ ID NO: 7
MIALDIDPLENTDFRVLELYSQKELRSSNVFDLEEIMREFNSYKQRVK

An illustrative HCMV gB AD-6 nucleic acid sequence is shown as SEQ ID NO: 8.

SEQ ID NO: 8
ATGATCGCCCTGGATATCGACCCGCTGGAAAATACCGACTTCAGGGTACT

GGAACTTTACTCGCAGAAAGAGCTGCGTTCCAGCAACGTTTTTGACCTCG

AAGAGATCATGCGCGAATTCAACTCGTACAAGCAGCGGGTAAAG

An illustrative HSV-1 gB AD-6 amino acid sequence is shown as SEQ ID NO: 9.

SEQ ID NO: 9
FIDLNITMLEDHEFVPLEVYTRHEIKDSGLLDYTEVQRRNQLHDLRFA

An illustrative HSV-1 gB AD-6 nucleic acid sequence is shown as SEQ ID NO: 10.

SEQ ID NO: 10
TTCATCGACCTCAACATCACCATGCTGGAGGATCACGAGTTTGTCCCCCT

GGAGGTGTACACCCGCCACGAGATCAAGGACAGCGGCCTGCTGGACTACA

CGGAGGTCCAGCGCCGCAACCAGCTGCACGACCTGCGCTTCGCC

An illustrative EBV gB AD-6 amino acid sequence is shown as SEQ ID NO: 11.

SEQ ID NO: 11
FISLNTSLIENIDFASLELYSRDEQRASNVfDLEGIFREYNFQAQNIA

An illustrative EBV gB AD-6 nucleic acid sequence is shown as SEQ ID NO: 12.

SEQ ID NO: 12
TTCATCTCACTAAACACCTCCCTCATCGAGAACATTGACTTTGCCTCCCT

GGAGCTGTACTCACGGGACGAACAGCGTGCCTCCAACGTCTTTGACCTGG

AGGGCATCTTCCGGGAGTACAACTTCCAGGCGCAAAACATCGCC

Accordingly, in one aspect, the invention provides a human herpesvirus immunogenic peptide comprising SEQ ID NO: 7, SEQ ID NO: 9 or SEQ ID NO: 11, or a sequence having at least 75% (suitably, at least 80%, at least 85%, at least 90%, at least 95%, at least 96%, at least 97%, at least 98% or at least 99%) identity thereto, or an immunogenic fragment thereof.

In another aspect, the invention provides an isolated human herpesvirus immunogenic peptide comprising SEQ ID NO: 7, SEQ ID NO: 9 or SEQ ID NO: 11, or a sequence having at least 75% (suitably, at least 80%, at least 85%, at least 90%, at least 95%, at least 96%, at least 97%, at least 98% or at least 99%) identity thereto, or an immunogenic fragment thereof.

In some embodiments, the human herpesvirus immunogenic peptide consists of SEQ ID NO: 7, SEQ ID NO: 9 or SEQ ID NO: 11, or a sequence having at least 75% (suitably, at least 80%, at least 85%, at least 90%, at least 95%, at least 96%, at least 97%, at least 98% or at least 99%) identity thereto, or an immunogenic fragment thereof.

In one embodiment, the human herpesvirus immunogenic peptide comprises SEQ ID NO: 7, a sequence having at least 75% (suitably, at least 80%, at least 85%, at least 90%, at least 95%, at least 96%, at least 97%, at least 98% or at least 99%) identity thereto, or an immunogenic fragment thereof.

In one embodiment, the human herpesvirus immunogenic peptide comprises SEQ ID NO: 9, a sequence having at least 75% (suitably, at least 80%, at least 85%, at least 90%, at least 95%, at least 96%, at least 97%, at least 98% or at least 99%) identity thereto, or an immunogenic fragment thereof.

In one embodiment, the human herpesvirus immunogenic peptide comprises SEQ ID NO: 11, a sequence having at least 75% (suitably, at least 80%, at least 85%, at least 90%, at least 95%, at least 96%, at least 97%, at least 98% or at least 99%) identity thereto, or an immunogenic fragment thereof.

In some embodiments, the human herpesvirus immunogenic peptide comprises SEQ ID NO: 7 or a sequence having at least 75% (suitably, at least 80%, at least 85%, at least 90%, at least 95%, at least 96%, at least 97%, at least 98% or at least 99%) identity thereto.

In some embodiments, the human herpesvirus immunogenic peptide comprises SEQ ID NO: 9 or a sequence having at least 75% (suitably, at least 80%, at least 85%, at least 90%, at least 95%, at least 96%, at least 97%, at least 98% or at least 99%) identity thereto.

In some embodiments, the human herpesvirus immunogenic peptide comprises SEQ ID NO: 11 or a sequence having at least 75% (suitably, at least 80%, at least 85%, at least 90%, at least 95%, at least 96%, at least 97%, at least 98% or at least 99%) identity thereto.

The human herpesvirus immunogenic peptide or immunogenic fragment of the invention comprises at least one immunogenic peptide epitope.

The immunogenic peptide epitope induces an immune response when administered to a subject. The immunogenic peptide epitope may induce a T cell response (e.g. a cytotoxic T cell response) and/or a humoral immune response in a subject. Preferably, the immunogenic peptide epitope may induce a memory humoral immune response in a subject. Suitably, the present immunogenic peptide or immunogenic fragment thereof is capable of inducing a humoral response comprising an antibody response that is capable of reducing or inhibiting at least part of the human herpesvirus lifecycle in a host organism/tissue/cell. For example, the antibody may reduce the cell-to-cell spread of the human herpesvirus—as described herein.

Methods for determining if a peptide is immunogenic, i.e. induces an immune response, are well-known in the art and include, for example, immune cell activation assays using $CD4^+$ and/or $CD8^+$ T cells or B cells. Suitable markers for activation may include cell proliferation and/or signature cytokines (e.g. for T cells—IFNγ, TNFα, IL-2, IL-13 and/or IL-17) production using methods such as ELISpot. Suitably, a peptide may be assayed for the production of antibodies, for example, using the method described herein.

An immunogenic peptide epitope refers to a peptide which is recognised by either a T cell receptor (TCR) or a B cell receptor (BCR)/antibody. Suitably, the immunogenic peptide epitope is a T cell epitope or a B cell epitope.

In an adaptive immune response, T cells are capable of recognising internal epitopes of a protein antigen, e.g. of AD-6. Antigen presenting cells (APC) take up protein antigens and degrade them into short peptide fragments. A peptide may bind to a major histocompatibility complex (MHC) class II molecule within the cell and be carried to the cell surface. When presented at the cell surface in the context of an MHC molecule, the peptide may be recognised by a T cell (via the TCR), in which case the peptide is a T cell epitope.

In one embodiment, the peptide epitope is a T cell epitope. Suitably, a peptide epitope may be capable of being recognised by a TCR when presented at the cell surface in the context of a MHC molecule. Peptides which bind to MHC class II molecules are typically between 8 and 20 amino acids in length, more usually between 10 and 17 amino acids in length, and can be longer (for example up to 40 amino acids). These peptides lie in an extended conformation along the MHC II peptide-binding groove which (unlike the MHC class I peptide-binding groove) is open at both ends. The peptide is held in place mainly by main-chain atom contacts with conserved residues that line the peptide-binding groove.

Peptides that bind to MHC class I are typically 7 to 13, more usually 8 to 10 amino acids in length. The binding of the peptide is stabilised at its two ends by contacts between atoms in the main chain of the peptide and invariant sites in the peptide-binding groove of all MHC class I molecules. There are invariant sites at both ends of the groove which bind the amino and carboxy termini of the peptide. Variations in peptide length are accommodated by a kinking in the peptide backbone, often at proline or glycine residues that allow flexibility.

A T cell epitope may thus be a peptide derivable from an antigen which is capable of binding to the peptide-binding groove of an MHC molecule and being recognised by a T cell in the context of an MHC molecule.

The minimal T cell epitope is the shortest fragment derivable from a T cell epitope, which is capable of binding to the peptide-binding grove of an MHC class I or II molecule and being recognised by a T cell in the contact of an MHC molecule. For a given immunogenic region, e.g. AD-6, it is typically possible to generate a "nested set" of overlapping peptides which act as epitopes, all of which contain the minimal epitope but differ in their flanking regions.

Thus, it is possible to identify the minimal T cell epitope for a particular MHC molecule: T cell combination by measuring the response to truncated peptides, i.e. peptide fragments. For example, if a response is obtained to the peptide comprising residues 1-20 in the overlapping library, sets which are truncated at both ends (i.e. 1-19, 1-18, 1-17 etc. and 2-20, 3-20, 4-20 etc.) can be used to identify the minimal epitope.

Methods for identifying T cell epitopes within a protein or peptide sequence are known in the art and include, but are not limited to MHC binding assays and/or immune cell activation assays using $CD4^+$ and/or $CD8^+$ T cells. Suitable markers for activation may include cell proliferation and/or signature cytokines (e.g. for T cells—IFNγ, TNFα, IL-13 and/or IL-17) production using methods such as ELISpot.

Bioinformatics methods for predicting T cell epitopes from a protein are known in the art and include, but are not limited to, EpiDOCK, MotifScan, Rankpep, SYFPEITHI, MAPPP, PREDIVAC, PEPVAC, EPISOPT, Vaxign, MHCPred, EpiTOP, BIMAS, TEPITOPE, Propred, E[iJen, IEDB-MHCI, IEDB-MHCII, MULTIPRED2, MHC2PRED, NetMHC, NetMHCII, NetMHCpan, NetMHCIIpan, nHLApred, SVMHC, SVRMHC, NetCTL and WAPP.

In one embodiment, the peptide epitope is a B cell epitope. A B cell epitope refers to a peptide which is capable of binding to a B cell receptor (BCR)/antibody. B cell epitopes are generally divided into two categories, linear epitopes and conformational epitopes, based on their structure and interaction with the antibody. A linear epitope is formed by the 3D conformation adopted by the interaction of contiguous amino acid residues. In contrast, a conformational epitope is formed by the 3D conformation adopted by the interaction of discontiguous amino acid residues.

Suitably, the peptide epitope may be a linear B cell epitope. Suitably, the peptide epitope may be a conformational B cell epitope.

Bioinformatics methods for predicting B cell epitopes from a protein are known in the art and include, but are not limited to, linear B cell epitope predictors such as PEOPLE, BepiPred, ABCpred, LBtope, BCPREDS and SVMtrip and conformational B cell epitope predictors such as CEP, DiscoTope, ElliPro, PEPITO, SEPPA, EPITOPIA, EPSVR, EPIPRED, PEASE, MIMOX, PEPITOPE, EpiSearch, MIMOPRO and CBTOPE.

Suitably, B cell epitopes may be identified from epitopes bound by antibodies isolated from a subject previously infected/recovered from a human herpesvirus infection and/or previously vaccinated with an antigen from the human herpesvirus. Methods for determining the epitope bound by an antibody (i.e. a B cell epitope) include, but are not limited to, X-ray crystallography, cryogenic electron microscopy, array-based oligo-peptide screening, site-directed mutagenesis mapping, high-throughput mutagenesis mapping, hydrogen-deuterium exchange and cross-linking-coupled mass spectrometry.

The human herpesvirus immunogenic peptide or immunogenic fragment may comprise at least one B cell epitope and/or at least one T cell epitope as defined herein. Suitably, the human herpesvirus immunogenic peptide or immunogenic fragment may comprise at least one B cell epitope and at least one T cell epitope as defined herein.

The peptide epitope(s) may independently be at least 7, at least 10, at least 15, at least 20, at least 30, at least 40 or at least 50 amino acids in length.

The peptide epitope(s) may independently be about 7 to about 50 or about 7 to about 20 amino acids in length.

It will be appreciated by one skilled in the art that an AD-6 immunogenic peptide provided herein (e.g. an AD-6 immunogenic peptide of SEQ ID NO: 7, SEQ ID NO: 9 or SEQ ID NO: 11) may comprise additional amino acids at the N- and/or C-terminus (e.g. at the N- and/or C-terminus of SEQ ID NO: 7, SEQ ID NO: 9 or SEQ ID NO: 11). In particular, the skilled person will appreciate that an AD-6 immunogenic peptide provided herein (e.g. an AD-6 immunogenic peptide of SEQ ID NO: 7, SEQ ID NO: 9 or SEQ ID NO: 11) having a small number of amino acids added to the N- and/or C-terminus can retain the ability to produce an immune response. For example, one, two or three additional amino acids may be present at the N- and/or C-terminus of an AD-6 immunogenic peptide provided herein (e.g. an AD-6 immunogenic peptide of SEQ ID NO: 7, SEQ ID NO: 9 or SEQ ID NO: 11).

In some embodiments, the human herpesvirus immunogenic peptide is about 50 (suitably, about 49, about 48, about 47 or about 46) or fewer amino acids in length. In some preferred embodiments, the human herpesvirus immunogenic peptide is about 48 or fewer amino acids in length.

It will be appreciated by one skilled in the art that a fragment of AD-6 (e.g. a fragment of SEQ ID NO: 7, SEQ ID NO: 9 or SEQ ID NO: 11) can retain the ability to produce an immune response. Thus, in some embodiments, the human herpesvirus immunogenic peptide comprises a fragment of any one of SEQ ID NO: 7, SEQ ID NO: 9 or SEQ ID NO: 11.

In some embodiments, said immunogenic fragment is about 47 (suitably, about 45, about 40, about 35, about 30, about 25, about 20, about 19, about 18, about 17, about 16, about 15, about 14, about 13, about 12, about 11, about 10) or fewer amino acids in length. Preferably, said immunogenic fragment is about 20 (suitably, about 19, about 18, about 17, about 16, about 15, about 14, about 13, about 12, about 11, about 10) or fewer amino acids in length. More preferably, said immunogenic fragment is about 15 (suitably, about 14, about 13, about 12, about 11, about 10) or fewer amino acids in length.

Illustrative immunogenic fragments of HCMV gB AD-6 are shown below:

(SEQ ID NO: 13)
VDSMIALDIDPLENT (SEQ ID NO: 14)
IALDIDPLENTDFRV (SEQ ID NO: 15)
IDPLENTDFRVLELY (SEQ ID NO: 16)
ENTDFRVLELYSQKE (SEQ ID NO: 17)
FRVLELYSQKELRSS (SEQ ID NO: 18)
ELYSQKELRSSNVFD (SEQ ID NO: 19)
QKELRSSNVFDLEEI (SEQ ID NO: 20)
RSSNVFDLEEIMREF (SEQ ID NO: 21)
VFDLEEIMREFNSYK (SEQ ID NO: 22)
EEIMREFNSYKQRVK (SEQ ID NO: 23)
REFNSYKQRVKYVED (SEQ ID NO: 24)
SYKQRVKYVEDKVVD (SEQ ID NO: 25)
ELYSQKELRSS (SEQ ID NO: 26)
SYKQRVKYVED

In some embodiments, said immunogenic fragment is selected from SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 and/or SEQ ID NO: 26.

In some embodiments, said immunogenic fragment is selected from SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 or SEQ ID NO: 26.

In some preferred embodiments, said immunogenic fragment is SEQ ID NO: 25 and/or SEQ ID NO: 26.

Preferably, said immunogenic fragment is SEQ ID NO: 25.

As used herein, the term "immunogenic fragment" means a fragment of the specified sequence which retains the ability to induce an immune response.

It will be appreciated by one skilled in the art that a variant of any one of SEQ ID NO: 13 to SEQ ID NO: 26 can retain the ability to produce an immune response. The variant may have one, two or three amino acid substitutions. Thus, in some embodiments, the human herpesvirus immunogenic peptide comprises a variant of any one of SEQ ID NO: 13 to SEQ ID NO: 26 having one, two or three amino acid substitutions. Suitably, the human herpesvirus immunogenic peptide comprises a variant of SEQ ID NO: 25 or SEQ ID NO: 26 having one, two or three amino acid substitutions. Suitably, the human herpesvirus immunogenic peptide comprises a variant of SEQ ID NO: 25 having one, two or three amino acid substitutions.

It will be appreciated by one skilled in the art that a shorter fragment of SEQ ID NO: 7 than the immunogenic fragments set forth in SEQ ID NO: 13 to SEQ ID NO: 26 can retain the ability to produce an immune response. Thus, in some embodiments, the human herpesvirus immunogenic peptide comprises a variant of any one of SEQ ID NO: 13 to SEQ ID NO: 26, having one, two or three amino acid deletions at the N- or C-terminus. Suitably, the human herpesvirus immunogenic peptide comprises a variant of SEQ ID NO: 25 or SEQ ID NO: 26 having one, two or three amino acid deletions at the N- or C-terminus. Suitably, the human herpesvirus immunogenic peptide comprises a variant of SEQ ID NO: 25 having one, two or three amino acid deletions at the N- or C-terminus.

It will be appreciated by one skilled in the art that a variant which is also a shorter fragment of SEQ ID NO: 7 than the immunogenic fragments set forth in SEQ ID NO: 13 to SEQ ID NO: 26 can retain the ability to produce an immune response. Thus, in some embodiments, the human herpesvirus immunogenic peptide comprises a variant of any one of SEQ ID NO: 13 to SEQ ID NO: 26, having one, two or three amino acid substitutions and having one, two or three amino acid deletions at the N- or C-terminus. Suitably, the human herpesvirus immunogenic peptide comprises a variant of SEQ ID NO: 25 or SEQ ID NO: 26 having one, two or three amino acid substitutions, and having one, two or three amino acid deletions at the N- or C-terminus. Suitably, the human herpesvirus immunogenic peptide comprises a variant of SEQ ID NO: 25 having one, two or three amino acid substitutions, and having one, two or three amino acid deletions at the N- or C-terminus.

Suitably, whether a peptide retains the ability to produce an immune response may be determined using the methods for determining if a peptide is immunogenic as described herein.

In some embodiments, said immunogenic fragment is selected from SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, or a variant thereof.

In some preferred embodiments, said immunogenic fragment is SEQ ID NO: 25 or SEQ ID NO: 26, or a variant thereof.

In some preferred embodiments, said immunogenic fragment is SEQ ID NO: 25 or SEQ ID NO: 26, or a variant thereof.

In some preferred embodiments, said immunogenic fragment is SEQ ID NO: 25 or SEQ ID NO: 26.

In some embodiments, said immunogenic fragment is SEQ ID NO: 13 or a variant thereof.

In some embodiments, said immunogenic fragment is SEQ ID NO: 14 or a variant thereof.

In some embodiments, said immunogenic fragment is SEQ ID NO: 15 or a variant thereof.

In some embodiments, said immunogenic fragment is SEQ ID NO: 16 or a variant thereof.

In some embodiments, said immunogenic fragment is SEQ ID NO: 17, or a variant thereof.

In some embodiments, said immunogenic fragment is SEQ ID NO: 18, or a variant thereof.

In some embodiments, said immunogenic fragment is SEQ ID NO: 19, or a variant thereof.

In some embodiments, said immunogenic fragment is SEQ ID NO: 20, or a variant thereof.

In some embodiments, said immunogenic fragment is SEQ ID NO: 21, or a variant thereof.

In some embodiments, said immunogenic fragment is SEQ ID NO: 22, or a variant thereof.

In some embodiments, said immunogenic fragment is SEQ ID NO: 23, or a variant thereof.

In some embodiments, said immunogenic fragment is SEQ ID NO: 24, or a variant thereof.

In some embodiments, said immunogenic fragment is SEQ ID NO: 25, or a variant thereof.

In some embodiments, said immunogenic fragment is SEQ ID NO: 26, or a variant thereof.

The variant may have one, two or three amino acid substitutions and/or may have one, two or three amino acid deletions at the N- and/or C-terminus. Suitably, the variant may have one, two or three amino acid substitutions and one, two or three amino acid deletions at the N- and/or C-terminus.

The variant may have one, two or three amino acid substitutions.

The variant may have one, two or three amino acid deletions at the N- and/or C-terminus. Suitably, the variant may have one, two or three amino acid deletions at the N- and C-terminus. Suitably, the variant may have one, two or three amino acid deletions at the N-terminus. Suitably, the variant may have one, two or three amino acid deletions at the C-terminus.

In some preferred embodiments, said amino acid substitutions are conservative amino acid substitutions.

Amino acids with similar biochemical properties may be defined as amino acids which can be substituted via a conservative substitution.

Conservative amino acid substitutions may be made on the basis of similarity in polarity, charge, solubility, hydrophobicity, hydrophilicity, and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to Table 1 below. Amino acids in the same block in the second column and preferably in the same line in the third column may be substituted for each other:

TABLE 1

| | | |
|---|---|---|
| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

The present invention also encompasses homologous substitution (substitution and replacement are both used herein to mean the interchange of an existing amino acid residue, with an alternative residue) i.e. like-for-like substitution such as basic for basic, acidic for acidic, polar for polar etc.

An aliphatic, non-polar amino acid may be a glycine, alanine, proline, isoleucine, leucine or valine residue.

An aliphatic, polar uncharged amino may be a cysteine, serine, threonine, methionine, asparagine or glutamine residue.

An aliphatic, polar charged amino acid may be an aspartic acid, glutamic acid, lysine or arginine residue.

An aromatic amino acid may be a histidine, phenylalanine, tryptophan or tyrosine residue.

Suitably, a conservative substitution may be made between amino acids in the same line in Table 1.

In some embodiments, said human herpesvirus is HCMV, HSV-1, and/or EBV.

In one preferred embodiment, said human herpesvirus is HCMV.

In one embodiment, said human herpesvirus is HSV-1.

In one embodiment, said human herpesvirus is EBV.

Nucleic Acid Sequence

In a further aspect, the present invention provides a nucleic acid sequence encoding a human herpesvirus immunogenic peptide of the invention.

In some embodiments, said nucleic acid sequence is selected from SEQ ID NO: 8, SEQ ID NO: 10 and SEQ ID NO: 12.

In one embodiment, said nucleic acid sequence is SEQ ID NO: 8.

In one embodiment, said nucleic acid sequence is SEQ ID NO: 10.

In one embodiment, said nucleic acid sequence is SEQ ID NO: 12.

The term "nucleic acid sequence" in relation to the present invention can be a double stranded or single stranded molecule and includes genomic DNA, cDNA, synthetic DNA, RNA and a chimeric DNA/RNA molecule. Preferably, it means a DNA sequence encoding a human herpesvirus immunogenic peptide of the present invention.

Typically, the nucleic acid sequence encompassed by the scope of the present invention is prepared using recombinant DNA techniques (i.e. recombinant DNA), as described herein.

In a preferred embodiment, the nucleic acid sequence encoding a human herpesvirus immunogenic peptide of the invention is an expression cassette.

In a further aspect, the present invention provides a vector comprising a nucleic acid sequence of the invention.

A vector is a tool that allows or facilitates the transfer of an entity from one environment to another. In accordance with the present invention, and by way of example, some vectors used in recombinant nucleic acid techniques allow entities, such as a nucleic acid of the invention, to be transferred into and expressed by a target cell. The vector may facilitate the integration of the nucleic acid sequence of the invention to maintain the nucleic acid sequence of the invention and its expression within the target cell.

The vector may be or may include an expression cassette (also termed an expression construct). Expression cassettes as described herein comprise regions of nucleic acid containing sequences capable of being transcribed. Thus, sequences encoding mRNA, tRNA and rRNA are included within this definition.

The term "cassette"—which is synonymous with "construct"—includes a nucleic acid sequence directly or indirectly attached to a promoter. The expression cassettes for use in the invention comprise a promoter for the expression of the nucleic acid sequence of the invention. Preferably, the cassette comprises at least a nucleic acid sequence of the invention operably linked to a promoter. The choice of expression cassette, e.g. plasmid or viral vector, will often depend on the host cell into which it is to be introduced.

The vector may contain one or more selectable marker genes (e.g. a kanamycin resistance gene) and/or traceable marker gene(s) (e.g. a gene encoding green fluorescent protein (GFP)).

Inhibitor

Herpesviruses grow in vivo both as a cell free and cell associated virus. gB is present in the virion and virally infected cells express gB at the cell surface. Thus, an inhibitor of gB may bind to gB in the virion or on the surface of infected cells, i.e. the inhibitor (e.g. an antibody) may recognise infected cells.

Accordingly, in a further aspect, the invention provides an inhibitor of human herpesvirus glycoprotein-B which is capable of binding to human herpesvirus glycoprotein-B on the surface of a cell.

In a further aspect, the invention provides an inhibitor of human herpesvirus glycoprotein-B which is capable of binding to human herpesvirus glycoprotein-B within SEQ ID NO: 7, SEQ ID NO: 9 or SEQ ID NO: 11, or a sequence having at least 75% identity thereto, or a fragment thereof.

Binding of gB on the surface of a cell may be determined using a method known in the art, including but not limited to cell-based binding assays using FACS or surface plasmon resonance. Suitably, binding of gB on the cell surface may be performed using the assay described herein (see Example 2). Suitably, the method may employ HFF cells infected with HCMV. After 72 hours, cells are stained with the AD-6 antibody and then incubated with fluorochrome-conjugated secondary antibody that recognises the AD-6 antibody. This assay can be performed in any cell type that supports lytic HCMV replication (e.g. HFF, ARPE, U373, dendritic cell, macrophage, endothelial cell).

In some preferred embodiments, the inhibitor binds to said human herpesvirus gB within a human herpesvirus immunogenic peptide as described herein. Preferably, the inhibitor may be capable of binding to an immunogenic peptide epitope within a human herpesvirus immunogenic peptide as described herein.

The inhibitor may be selected from one or more of the following: an antibody, an Ig fusion protein, a polypeptide, a peptide, a polynucleotide, a small molecule, a non-antibody scaffold, an aptamer, or combinations thereof.

The inhibitor may reduce or inhibit at least part of the human herpesvirus lifecycle in a host organism/tissue/cell. For example, the inhibitor may reduce the cell-to-cell spread of the human herpesvirus. Models of cell-to-cell spread are known in the art. For example, a cell line (e.g. human fibroblast or epithelial cell line) may be infected with a human herpesvirus and treated with the inhibitor and complement. A reduction in cell-to-cell spread may be determined by a reduction of cell infection (which is measured by enumerating the % of infected cells) compared to a control experiment which has not been treated with inhibitor.

The inhibitor may reduce viral cell-to-cell spread by at least 1.5-fold (suitably, at least 2-fold, at least 2.5-fold, at least 3-fold, at least 4-fold or at least 5-fold) relative to viral cell-to-cell spread in the absence of inhibitor.

The inhibitor may reduce viral cell-to-cell spread by at least 10% (suitably, at least 20%, at least 30%, at least 40%, at least 50% or at least 100%) relative to viral cell-to-cell spread in the absence of inhibitor. Preferably, the inhibitor may reduce viral cell-to-cell spread by at least 20% relative to viral cell-to-cell spread in the absence of the immunogenic composition. More preferably, the inhibitor may reduce viral cell-to-cell spread by at least 30% relative to viral cell-to-cell spread in the absence of inhibitor.

The inhibitor (e.g. an antibody) may be capable of selectively binding to a human herpesvirus gB (e.g. a human herpesvirus immunogenic peptide as described herein) and thus may have a greater binding affinity for a human herpesvirus gB as compared to its binding affinity for other proteins/molecules. Preferably, the inhibitor does not bind to other proteins or binds with a greatly reduced affinity compared to the binding to said human herpesvirus gB (e.g. with an affinity of at least 10, 50, 100, 500, 1000 or 10000 times less than its affinity for said human herpesvirus gB). Thus, the inhibitor as referred to herein may bind to said human herpesvirus gB (e.g. a human herpesvirus immunogenic peptide as described herein) with at least 10, 50, 100, 500, 1000 or 10000 times the affinity of its binding to other proteins. The binding affinity of the inhibitor can be determined using methods well known in the art, such as with the Biacore system.

The inhibitor may have a high binding affinity for said human herpesvirus gB (e.g. a human herpesvirus immunogenic peptide as described herein), i.e. may have a $K_d$ in the range of $10^{-5}$ M, $10^{-6}$ M, $10^{-7}$ M or $10^{-9}$ M or less. The anti-gB binding domain of the inhibitor may have a binding affinity for said human herpesvirus gB (e.g. a human herpesvirus immunogenic peptide as described herein) that corresponds to a $K_d$ of less than 30 nM, 20 nM, 15 nM or 10 nM, more preferably of less than 10, 9.5, 9, 8.5, 8, 7.5, 7, 6.5, 6, 5.5, 5, 4.5, 4, 3.5, 3, 2.5, 2, 1.5 or 1 nM, most preferably less than 0.9, 0.8, 0.7, 0.6, 0.5, 0.4, 0.3, 0.2 or 0.1 nM.

Any appropriate method of determining $K_d$ may be used. Preferably, the $K_d$ is determined by testing various concentrations of the test agent against various concentrations of antigen (i.e. human herpesvirus gB, e.g. a human herpesvirus immunogenic peptide as described herein) in vitro to establish a saturation curve, for example using the Lineweaver-Burk method, or by using commercially available binding model software, such as the 1:1 binding model in the BIAcore 1000 Evaluation software.

In some embodiments, said inhibitor is an antibody.

In some embodiments, said antibody is a monoclonal antibody, a humanised antibody, a single-chain antibody or an antibody fragment. Suitably antibodies include, but are not limited to, monoclonal and polyclonal antibodies, engineered antibodies including chimeric, CDR-grafted and humanised antibodies, single-chain antibodies, antibody fragments and artificially selected antibodies produced using phage display or alternative techniques.

Suitably the antibody is a monoclonal antibody.

Suitable antibody fragments capable of binding to a selected target, include Fv, ScFv, F(ab') and $F(ab')_2$. In addition, alternatives to classical antibodies may also be used in the invention, for example "avibodies", "avimers", "anticalins", "nanobodies" and "DARPins".

Reference to "scFv" or "single-chain variable fragment" as used herein includes molecules wherein the variable heavy (VH) and variable light chain (VL) of an antibody are linked via a flexible oligopeptide. A scFv is thus a fusion between at least one variable heavy and at least one variable light chain.

Reference to a "complementarity determining region" or "CDR" as used herein refers to the regions of hypervariability within antibodies which bind to the specific antigen e.g. to CLEC14A. The CDRs of an antibody thus usually provide an antibody with its binding specificity. Three CDRs may be present in the variable region of each heavy chain of an intact antibody molecule (i.e. comprising two full length heavy and two full length light chains) and three CDRs may be present in the variable region of each light chain (heavy chain CDRs 1, 2 and 3 and light chain CDRs 1, 2 and 3, numbered from the amino to the carboxy terminus). The CDRs of the variable regions of a heavy and light chain of an antibody can be predicted from the heavy and light chain variable region sequences of the antibody, using prediction software known in the art, including but not limited to the Abysis algorithm (www.bioinf.org.uk/abysis/sequence_input/key_annotation/key_annotation.cgi) and IMGT/V-QUEST software, e.g. the IMGT algorithm (ImMunoGeneTics) (www.IMGT.org; Lefranc et al, 2009 NAR 37:D1006-D1012; and Lefranc 2003, Leukemia 17:260-266). CDRs may vary in length, depending on the antibody from which they are predicted and between the heavy and light chains. A CDR for example, may range from 2 amino acids in length to 20 amino acids in length, e.g. from 3-14 amino acids in length. The Kabat nomenclature is followed herein in order to define the positioning of the CDRs (Kabat et al., 1991, $5^{th}$ Ed. Public Health Service, National Institutes of Health, Bethesda, MD, 647-669, incorporated herein by reference).

The term "heavy chain variable region" (VH domain) as used herein refers to the variable region of a heavy chain of an antibody molecule.

The term "light chain variable region" (VL domain) as used herein refers to the variable region of a light chain of an antibody molecule.

Antibodies capable of binding to human herpesvirus gB (e.g. within a human herpesvirus immunogenic peptide as described herein) can be produced using any method known in the art. Methods for the production of monoclonal antibodies, recombinant antibodies and aptamers are reviewed in Groff et al. (Biotechnology Advances 2015, 33(8):1787-1798) and Dangi et al. (Front Pharmacol. 2018; 9:630)—each of which is incorporated herein by reference.

Antibodies capable of inhibiting gB may be identified using any method known in the art, including an assay for binding of gB on the surface of a cell or a viral cell-to-cell spread assay as described herein.

Immunogenic Composition and Pharmaceutical Composition

In a further aspect, the invention provides an immunogenic composition comprising a human herpesvirus immunogenic peptide of the invention.

In a further aspect, the invention provides an immunogenic composition comprising a nucleic acid sequence of the invention or a vector of the invention.

In a further aspect, the invention provides a pharmaceutical composition comprising an inhibitor of the invention.

The immunogenic composition may induce an immune response when administered to a subject. The immunogenic composition may induce a T cell response (e.g. a cytotoxic T cell response) and/or a humoral immune response in a subject. Preferably, the immunogenic composition may induce a memory humoral immune response in a subject. Suitably, the present immunogenic composition is capable of inducing a humoral response comprising an antibody response that is capable of reducing or inhibiting at least part of the human herpesvirus lifecycle in a host organism/tissue/cell. For example, the antibody may reduce the cell-to-cell spread of the human herpesvirus—as described herein.

Methods for determining if an immunogenic composition induces an immune response are well-known in the art and include, for example, immune cell activation assays using $CD4^+$ and/or $CD8^+$ T cells or B cells as described herein above.

Suitably, the induction of humoral immunity to a human herpesvirus may refer to B cell activity. The activity of B cells may be determined using methods which are known in the art. For example, the activity of B cells may be determined by determining antibody (e.g. IgG or IgM) production or antiviral cytokine production (e.g. IFNγ or IL-6) following treatment with the immunogenic composition. Enhancement of B cell activity may be determined by an increase in antibody or effector cytokine (e.g. percentage of effector cytokine positive cells) as determined by flow cytometry or amount of effector cytokine mRNA or protein as determined by qPCR, ELISA or ELISPOT, respectively) compared to a control experiment which has not been treated with the immunogenic composition.

For example, levels of antiviral cytokine production in B-cells treated with an immunogenic composition may be increased by at least 10%, at least 20%, at least 30%, at least 40%, at least 50%, at least 75% or at least 100% compared to control cells which have not been treated with the immunogenic composition.

Suitably, the induction of T cell immunity (e.g. of humoral immunity) to a human herpesvirus may refer to $CD4^+$ T cell activity. The activity of $CD4^+$ T cells may be determined using methods which are known in the art. For example, $CD4^+$ T cell activity may be assessed by determining effector cytokine production (i.e. IFNγ, IL-21 or IL-4) following treatment with the immunogenic composition. Enhancement of $CD4^+$ T cell activity may be determined by an increase in effector cytokine (e.g. percentage of effector cytokine positive cells as determined by flow cytometry or amount of effector cytokine mRNA or protein as determined by qPCR, ELISA or ELISPOT, respectively) compared to a control experiment which has not been treated with the immunogenic composition.

For example, levels of effector cytokine in $CD4^+$ T cell treated with an immunogenic composition may be increased by at least 10%, at least 20%, at least 30%, at least 40%, at least 50%, at least 75% or at least 100% compared to control cells which have not been treated with the immunogenic composition.

Suitably, induced T cell immunity to a human herpesvirus may refer to CD8+ T cell activity. The activity of $CD8^+$ T cells may be determined using methods which are known in the art. For example, $CD8^+$ T cell activity may be assessed by determining effector cytokine production (i.e. IFNγ/TNF/IL-2) following treatment with the immunogenic composition. Enhancement of $CD8^+$ T cell activity may be determined by an increase in effector cytokine (e.g. percentage of effector cytokine positive cells as determined by flow cytometry or amount of effector cytokine mRNA or protein as determined by qPCR or ELISA or ELISPOT, respectively) compared to a control experiment which has not been treated with the immunogenic composition. Proliferative expansion of antigen-specific $CD8^+$ T cells can also be assessed by staining with MHC/peptide multimers.

For example, levels of effector cytokine in $CD8^+$ T cells treated with an immunogenic composition may be increased by at least 10%, at least 20%, at least 30%, at least 40%, at least 50%, at least 75% or at least 100% compared to control cells which have not been treated with the immunogenic composition.

The pharmaceutical composition may reduce or inhibit at least part of the human herpesvirus lifecycle in a host organism/tissue/cell. For example, the pharmaceutical composition may reduce the cell-to-cell spread of the human herpesvirus. Models of cell-to-cell spread are known in the art and described herein above.

The pharmaceutical composition may reduce viral cell-to-cell spread by at least 1-fold (suitably, at least 1.5-fold, at least 2-fold, at least 2.5-fold, at least 3-fold, at least 4-fold or at least 5-fold) relative to viral cell-to-cell spread in the absence of the immunogenic composition. The immunogenic composition may reduce viral cell-to-cell spread by at least 10% (suitably, at least 20%, at least 30%, at least 40%, at least 50% or at least 100%) relative to viral cell-to-cell spread in the absence of the immunogenic composition. Preferably, the immunogenic composition may reduce viral cell-to-cell spread by at least 20% relative to viral cell-to-cell spread in the absence of the immunogenic composition. More preferably, the immunogenic composition may reduce viral cell-to-cell spread by at least 30% relative to viral cell-to-cell spread in the absence of the immunogenic composition.

In the context of the present invention, an immunogenic composition is administered to a subject in order to enhance the subject's immune response to human herpesvirus infection. The subject may be seronegative or seropositive for a human herpesvirus. Preferably, the subject is seronegative for a human herpesvirus.

In the context of the present invention, a pharmaceutical composition is administered to a subject in order to treat and/or prevent a human herpesvirus infection. The subject may be seronegative or seropositive for a human herpesvirus.

Suitably, the immunogenic composition or pharmaceutical composition will be formulated for administration by injection, for example by intramuscular, intradermal, intravenous or sub-cutaneous injection.

An immunogenic composition or a pharmaceutical composition will generally be administered in admixture with a pharmaceutical carrier, excipient or diluent, particularly for human therapy. Suitably, an immunogenic composition or a pharmaceutical composition may be administered in admixture with an adjuvant, particularly for human therapy.

Vaccine

In a further aspect, the invention provides a vaccine comprising a human herpesvirus immunogenic peptide of the invention.

In a further aspect, the invention provides a vaccine comprising a nucleic acid sequence of the invention or a vector of the invention.

In a further aspect, the invention provides a vaccine comprising an inhibitor of the invention.

The vaccine may induce a protective immune response when administered to a subject, i.e. an immune response that is protective against subsequent challenge with a human herpesvirus. The vaccine may induce a protective T cell response (e.g. a cytotoxic T cell response) and/or a protective humoral immune response in a subject. Preferably, the vaccine may induce a memory humoral immune response in a subject. Suitably, the present vaccine is capable of inducing a humoral response comprising an antibody response that is capable of reducing or inhibiting at least part of the human herpesvirus lifecycle in a host organism/tissue/cell. For example, the antibody may reduce the cell-to-cell spread of the human herpesvirus—as described herein.

Methods for determining if a vaccine induces a protective immune response are well-known in the art and include, for example, vaccination of a subject and subsequent challenge (either natural or deliberate) with a human herpesvirus.

In the context of the present invention, a vaccine is administered to a subject in order to enhance the subject's immune response to human herpesvirus infection. The subject may be seronegative or seropositive for a human herpesvirus. Preferably, the subject is seronegative for a human herpesvirus. The subject may be seropositive for a human herpesvirus.

Suitably, the vaccine will be formulated for administration by injection, for example by intramuscular, intradermal, intravenous or sub-cutaneous injection.

A vaccine will generally be administered in admixture with a pharmaceutical carrier, excipient or diluent, particularly for human therapy. Suitably, a vaccine may be administered in admixture with an adjuvant, particularly for human therapy.

Treatment or Prevention of Human Herpesvirus Infection

Original antigenic sin means that the immune system does not make new antibody responses if it is presented with an antigen that contains epitopes it has already seen; instead it boosts what it already knows. A human herpesvirus immunogenic peptide of the invention that presents AD-6 to the immune system (e.g. in the context of an AD-6 subunit vaccine) has the potential to be effective, particularly if the presentation of other ADs of gB is absent. This would allow the immune system to focus on generating humoral responses against the novel AD-6 epitope rather than potential "decoy" epitopes (other ADs e.g. AD-1, AD-2, AD-3, AD-4 and/or AD-5) present in gB, i.e. to avoid the issue of original 'antigenic sin' that is seen in HCMV seropositive patients with the current gB vaccine, i.e. the candidate gB vaccine comprising recombinant HCMV gB and MF59 adjuvant (Baraniak et al. 2019 J. Infect. Dis. 220(2) 228-232). In other words, this would enable the vaccination of individuals who are already infected (e.g. with a herpesvirus such as HCMV) as well as uninfected individuals. This ability is important for the treatment of herpesvirus infection, and particular HCMV infection, due to the prevalence of these infections, with approximately 50% of the world's population already seropositive for HCMV and at risk from disease caused by reactivation.

Thus, the presentation of an AD-6 immunogenic peptide as described herein (e.g. in the context of an AD-6 subunit vaccine) to the immune system would both focus the humoral response against AD-6 and prevent deleterious response against other gB domains. This may be sufficient to improve the efficacy of a gB-based vaccine, for example, in both seropositive and seronegative individuals.

In a further aspect, the invention provides an immunogenic composition of the invention for use in the treatment or prevention of human herpesvirus infection in a subject.

In a further aspect, the invention provides a pharmaceutical composition of the invention for use in the treatment or prevention of human herpesvirus infection in a subject.

In a further aspect, the invention provides a vaccine of the invention for use in the treatment or prevention of human herpesvirus infection in a subject.

In a further aspect, the invention provides an inhibitor of the invention for use in the treatment or prevention of human herpesvirus infection in a subject.

Also provided is a method for the treatment and/or prevention of a human herpesvirus infection, comprising administering an immunogenic composition of the invention, a pharmaceutical composition of the invention, a vaccine of the invention or an inhibitor of the invention to a subject in need thereof.

Also provided is a method for the treatment of a human herpesvirus infection, comprising administering an immunogenic composition of the invention, a pharmaceutical composition of the invention, a vaccine of the invention or an inhibitor of the invention to a subject in need thereof.

Also provided is a method for the prevention of a human herpesvirus infection, comprising administering an immunogenic composition of the invention, a pharmaceutical composition of the invention, a vaccine of the invention or an inhibitor of the invention to a subject in need thereof.

In some embodiments, the cell-to-cell spread of the human herpesvirus is inhibited.

In some embodiments, the immunogenic composition, pharmaceutical composition, vaccine or inhibitor is for use in the prevention of human herpesvirus infection in the subject.

In some embodiments, the immunogenic composition, pharmaceutical composition, vaccine or inhibitor is for use in the treatment of human herpesvirus infection in the subject.

In some embodiments, the human herpesvirus is HCMV, HSV-1, and/or EBV.

In one preferred embodiment, the human herpesvirus is HCMV.

In some embodiments, the human herpesvirus is HSV-1.

In some embodiments, the human herpesvirus is EBV.

The term "treat/treatment/treating" may refer generally to administering an immunogenic composition, vaccine, inhibitor or pharmaceutical composition of the invention to a subject having an existing disease or condition in order to reduce, alleviate or eliminate one or more symptoms associated with the disease, disorder or condition which is being treated and/or to slow down, reduce or block the progression of the disease, disorder or condition which is being treated.

The term "prevent/prevention/prophylaxis" may refer generally to administering an immunogenic composition, vaccine, inhibitor or pharmaceutical composition of the invention to a subject having an existing disease or condition or at risk of developing a disease or condition in order to delay or prevent the onset of the symptoms of the disease, disorder or condition. Prevention may be absolute (such that no disease occurs) or may be effective only in some individuals or for a limited amount of time.

Combinations

The immunogenic composition of the invention, pharmaceutical composition of the invention, vaccine of the invention or inhibitor of the invention may be administered to the subject in combination with at least one further pharmaceutically active agent.

In one embodiment, the immunogenic composition of the invention may be administered to the subject in combination with at least one further pharmaceutically active agent.

In one embodiment, the pharmaceutical composition of the invention may be administered to the subject in combination with at least one further pharmaceutically active agent.

In one embodiment, the vaccine of the invention may be administered to the subject in combination with at least one further pharmaceutically active agent.

In one embodiment, the inhibitor of the invention may be administered to the subject in combination with at least one further pharmaceutically active agent.

Suitably, "in combination" may mean that the immunogenic composition, pharmaceutical composition, vaccine or inhibitor of the invention and the further pharmaceutically active agent are administered to the subject in a simultaneous, combined, sequential or separate manner.

By "simultaneous", it is to be understood that the two agents are administered concurrently, whereas the term "combined" is used to mean they are administered, if not simultaneously, then "sequentially" within a time frame that they both are available to act therapeutically within the same time frame. Thus, administration "sequentially" may permit one agent to be administered within 5 minutes, 10 minutes or a matter of hours after the other provided the circulatory half-life of the first administered agent is such that they are both concurrently present in therapeutically effective amounts. The time delay between administration of the components will vary depending on the exact nature of the components, the interaction there-between, and their respective half-lives.

In contrast to "combined" or "sequential", "separate" may be understood as meaning that the gap between administering one agent and the other agent is significant, i.e. the first administered agent may no longer be present in the bloodstream in a therapeutically effective amount when the second agent is administered.

Suitably, the immunogenic composition, pharmaceutical composition, vaccine or inhibitor of the invention and further pharmaceutically active agent are administered in a simultaneous, combined, or sequential manner to a subject.

Suitably, the immunogenic composition, pharmaceutical composition, vaccine or inhibitor of the invention and further pharmaceutically active agent may be administered as a single composition. For example, the immunogenic composition may comprise a nucleic acid construct encoding a human herpesvirus immunogenic peptide—as described herein—and be provided as part of a vaccine as described herein.

Suitably, the immunogenic composition, pharmaceutical composition, vaccine or inhibitor of the invention may be administered as a separate composition to the further pharmaceutically active agent. For example, the inhibitor may be a small molecule administered orally and the further pharmaceutically active agent may be a HCMV vaccine administered by intramuscular, subcutaneous or intradermal or intravenous injection. Alternatively, the inhibitor may be a small molecule administered orally or an antibody administered by intramuscular, subcutaneous or intradermal or intravenous injection and the further pharmaceutically active agent may be an antiviral (e.g. GCV) administered by intravenous injection.

The at least one further pharmaceutically active agent may be selected from an antiviral, a herpesvirus vaccine, an immunostimulatory cytokine, a checkpoint inhibitor, TCR-gene-engineered T cells, activators of innate immunity, monoclonal or bispecific antibodies, CAR cells, soluble T cell receptors, or any combination thereof.

Suitably, the at least one further pharmaceutically active agent may be selected from an antiviral, a herpesvirus vaccine, an immunostimulatory cytokine, TCR-gene-engineered T cells, activators of innate immunity, monoclonal or bispecific antibodies, CAR cells, soluble T cell receptors, or any combination thereof.

Antivirals include, but are not limited to, antivirals that target the viral DNA polymerase. Further antivirals include agents which interfere or inhibit the ability of the herpesvirus to enter host cells and others such as capsid assembly inhibitors, anti-HCMV siRNA, etc. Suitable antivirals include ganciclovir (GCV), foscavir, foscarnet, cidofovir, acyclovir (Zovirax), famciclovir (Famvir), valacyclovir (Valtrex), penciclovir, maribavir, letermovir.

Current antivirals are generally not considered to be suitable for all patients, e.g. pregnant women or neonates, because of the level of toxicity.

Suitable immunostimulatory cytokines include, but are not limited to, IFN-α, pegylated IFN-α, IFN-λ, IFNγ, GM-CSF, IL-7, IL-12, IL-15, IL-18 and IL-21.

Suitable checkpoint inhibitors include, but are not limited to, both inhibitory and activatory molecules, and interventions may apply to either or both types of molecule. Immune checkpoint inhibitors include, but are not limited to, PD-1 inhibitors, PD-L1 inhibitors, Lag-3 inhibitors, Tim-3 inhibitors, TIGIT inhibitors, BTLA inhibitors and CTLA-4 inhibitors, for example. Co-stimulatory antibodies deliver positive signals through immune-regulatory receptors including but not limited to ICOS, CD137, CD27 OX-40 and GITR.

Suitably, the checkpoint inhibitor may be a PD-1 or PD-L1 inhibitor.

Examples of suitable immune checkpoint interventions which prevent, reduce or minimize the inhibition of immune cell activity include pembrolizumab, nivolumab, atezolizumab, durvalumab, avelumab, tremelimumab and ipilimumab.

A TCR-gene-engineered cell refers to a cell, preferably a T cell, which has been engineered to introduce an exogenous nucleic acid encoding an exogenous TCR into the cell and thus redirect the specificity of cell to a target antigen of interest. In the context of the present invention, the cell is suitably redirected to a human herpesvirus target antigen of interest. TCR-gene-engineered cells and anti-HCMV T cells are described in the art, for example see Schub et al. (J Immunol 2009; 183:6819-6830) and Wagner et al. (J Biol. Chem. 2019; 294:5790-5804); each of which is incorporated herein by reference.

The present invention also encompasses administering an immunogenic composition, a pharmaceutical composition, a vaccine or an inhibitor of the invention in combination with human herpesvirus-specific (e.g. HCMV-specific) T cells which have been isolated, and preferably enriched, from a subject. The subject is suitably the same subject with human herpesvirus infection who is to be treated according to the invention.

Soluble T cell receptors (sTCR) typically comprise the variable domain and at least part of the TCR constant domain but lack the transmembrane domain and intracellular, cytoplasmic domain. Suitably, the sTCR does not comprise a transmembrane domain. Suitably, the sTCR is not anchored on the surface of cell. In the context of the present invention, the sTCR is directed to a human herpesvirus target antigen of interest.

A classical CAR is a chimeric type I trans-membrane protein which connects an extracellular antigen-recognizing domain (binder) to an intracellular signalling domain (endodomain). The binder is typically a single-chain variable fragment (scFv) derived from a monoclonal antibody (mAb), but it can be based on other formats which comprise an antibody-like antigen binding site. A spacer domain is usually necessary to isolate the binder from the membrane and to allow it a suitable orientation. A common spacer domain used is the Fc of IgG1. More compact spacers can suffice e.g. the stalk from CD8α and even just the IgG1 hinge alone, depending on the antigen. A trans-membrane domain anchors the protein in the cell membrane and connects the spacer to the endodomain.

When the CAR binds the target-antigen, this results in the transmission of an activating signal to the T-cell it is expressed on. Thus, the CAR directs the specificity and cytotoxicity of the T cell towards cells expressing the targeted antigen.

CARs typically therefore comprise: (i) an antigen-binding domain; (ii) a spacer; (iii) a transmembrane domain; and (iii) an intracellular domain which comprises or associates with a signalling domain.

The antigen binding domain is the portion of the CAR which recognizes antigen. Numerous antigen-binding domains are known in the art, including those based on the antigen binding site of an antibody, antibody mimetics, and T-cell receptors. For example, the antigen-binding domain may comprise: a single-chain variable fragment (scFv) derived from a monoclonal antibody; a natural ligand of the target antigen; a peptide with sufficient affinity for the target; a single domain antibody; an artificial single binder such as a Darpin (designed ankyrin repeat protein); or a single-chain derived from a T-cell receptor.

The antigen binding domain may comprise a domain which is not based on the antigen binding site of an antibody. For example, the antigen binding domain may comprise a domain based on a protein/peptide which is a soluble ligand for a tumour cell surface receptor (e.g. a soluble peptide such as a cytokine or a chemokine); or an extracellular domain of a membrane anchored ligand or a receptor for which the binding pair counterpart is expressed on the tumour cell. The antigen binding domain may be based on a natural ligand of the antigen.

The antigen binding domain may comprise an affinity peptide from a combinatorial library or a de novo designed affinity protein/peptide.

CARs comprise a spacer sequence to connect the antigen-binding domain with the transmembrane domain and spatially separate the antigen-binding domain from the endodomain. A flexible spacer allows the antigen-binding domain to orient in different directions to facilitate binding.

The transmembrane domain is the portion of the CAR which spans the membrane. The transmembrane domain may be any protein structure which is thermodynamically stable in a membrane. This is typically an alpha helix comprising of several hydrophobic residues. The transmembrane domain of any transmembrane protein can be used to supply the transmembrane portion of the CAR. The presence and span of a transmembrane domain of a protein can be determined by those skilled in the art using the TMHMM algorithm (http://www.cbs.dtu.dk/services/TMHMM-2.0/). Alternatively, an artificially designed TM domain may be used.

The transmembrane domain may be derived from CD28, which gives good receptor stability.

The endodomain is the signal-transmission portion of the CAR. It may be part of or associate with the intracellular domain of the CAR. After antigen recognition, receptors cluster, native CD45 and CD148 are excluded from the synapse and a signal is transmitted to the cell. The most commonly used endodomain component is that of CD3-zeta which contains 3 ITAMs. This transmits an activation signal to the T cell after antigen is bound. CD3-zeta may not provide a fully competent activation signal and additional co-stimulatory signaling may be needed. For example, chimeric CD28 and OX40 can be used with CD3-Zeta to transmit a proliferative/survival signal, or all three can be used together.

The endodomain may comprise:

(i) an ITAM-containing endodomain, such as the endodomain from CD3 zeta; and/or (ii) a co-stimulatory domain, such as the endodomain from CD28; and/or (iii) a domain which transmits a survival signal, for example a TNF receptor family endodomain such as OX-40 or 4-1BB.

Illustrative HCMV-specific CARs are described in Stripecke et al. (Blood. 2016; 128:5721) and Ali et al. (J. Infectious Diseases 2020; 222:853-862)—each of which is incorporated herein by reference.

Suitably, the CAR cell may be a T cell comprising an exogenous nucleic acid construct which encodes a CAR as described herein.

Methods for introducing an exogenous TCR or CAR into a cell are well known in the art and include introducing into a cell in vitro or ex vivo a polynucleotide encoding a TCR or CAR as defined herein. Suitably, the method further comprises incubating the cell under conditions causing expression of TCR or CAR. Optionally, the method may further comprise a step of purifying the engineered cells. The nucleic acid molecule encoding the TCR or CAR may be introduced into the cell using known vectors, for example a lentiviral vector. The term "vector" includes an expression vector, i.e. a construct capable of in vivo or in vitro/ex vivo expression. Also encompassed are cloning vectors.

Viral delivery systems include but are not limited to adenovirus vector, an adeno-associated viral (AAV) vector, a herpes viral vector, retroviral vector, lentiviral vector, baculoviral vector.

Retroviruses are RNA viruses with a life cycle different to that of lytic viruses. In this regard, a retrovirus is an infectious entity that replicates through a DNA intermediate. When a retrovirus infects a cell, its genome is converted to a DNA form by a reverse transcriptase enzyme. The DNA copy serves as a template for the production of new RNA genomes and virally encoded proteins necessary for the assembly of infectious viral particles.

There are many retroviruses, for example murine leukemia virus (MLV), human immunodeficiency virus (HIV), equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV) and all other retroviridiae including lentiviruses. A detailed list of retroviruses may be found in Coffin et al ("Retroviruses" 1997 Cold Spring Harbour Laboratory Press Eds: J M Coffin, S M Hughes, H E Varmus pp 758-763). Lentiviruses also belong to the retrovirus family, but they can infect both dividing and non-dividing cells (Lewis et al (1992) EMBO J. 3053-3058). The vector may be a retroviral vector. The vector may be based on or derivable from the MP71 vector backbone. The vector may lack a full-length or truncated version of the Woodchuck Hepatitis Response Element (WPRE). For efficient infection of human cells, viral particles may be packaged with amphotropic envelopes or gibbon ape leukemia virus envelopes.

Suitably, a TCR-gene-engineered cell or CAR cell as described herein may be treated in vitro or ex vivo with an immunogenic composition comprising a nucleic acid sequence or vector as described herein. Following in vitro or ex vivo treatment with the immunogenic composition, the TCR-gene-engineered cell or CAR cell may subsequently be administered to a subject to treat and/or prevent human herpesvirus infection as described herein.

Accordingly, in one aspect the present invention provides a method of treating and/or preventing a human herpesvirus infection in a subject which comprises the following steps:

(i) isolation of a cell-containing sample from a subject;
(ii) introducing a nucleic acid sequence encoding a TCR or CAR to the cells; and
(iii) administering the cells from (ii) to the subject.

Suitably the cells from (ii) may be expanded in vitro before administration to the subject.

The subject in steps (i) and (iii) may be the same or a different subject. In other words, the cells may be autologous or may be allogenic to the subject to be treated.

Step (ii) may optionally also comprise introducing a nucleic acid sequence or vector of the invention which is capable of expressing the human herpesvirus immunogenic peptide as described herein.

Suitable activators of innate immunity include, but are not limited to, toll-like receptor (TLR) agonists and RIG-I/NOD agonists. Examples of TLR agonists include TLR-7 agonists, TLR-8 agonists and TLR-9 agonists. These agonists are typically provided as small molecules in a composition for oral administration.

Dosage

The skilled person can readily determine an appropriate dose of one of the agents of the invention to administer to a subject without undue experimentation. Typically, a physician will determine the actual dosage which will be most suitable for an individual patient and it will depend on a variety of factors including the activity of the specific agent employed, the metabolic stability and length of action of that agent, the age, body weight, general health, sex, diet, mode and time of administration, rate of excretion, drug combination, the severity of the particular condition, and the individual undergoing therapy. There can of course be individual instances where higher or lower dosage ranges are merited, and such are within the scope of the invention.

The skilled person appreciates, for example, that route of delivery (e.g. oral vs. intravenous vs. subcutaneous etc.) may impact the required dosage (and vice versa). For example, where particularly high concentrations of an agent within a particular site or location are desired, focussed delivery may be preferred. Other factors to be considered when optimizing routes and/or dosing schedule for a given therapeutic regimen may include, for example, the disease being treated (e.g. type or stage etc.), the clinical condition of a subject (e.g. age, overall health etc.), the presence or absence of combination therapy, and other factors known to medical practitioners.

The dosage is such that it is sufficient to improve symptoms or markers of the disease—as described herein.

Subject

A "subject" refers to either a human or non-human animal.

Examples of non-human animals include vertebrates, for example mammals, such as non-human primates (particularly higher primates).

Preferably, the subject is a human. The subject may be any age, gender or ethnicity.

The subject may have a human herpesvirus infection, or be thought to be at risk from contracting or developing a human herpesvirus infection, because of, for example, a compromised immune system, an immature immune system, family history of the disease or the presence of genetic or phenotypic (e.g. biomarkers) associated with the disease.

The subject may show one or more signs or symptoms of a human herpesvirus infection. The subject may have been previously characterised as having a human herpesvirus infection by other diagnostic methods.

The subject may have been previously treated with antiviral therapy (e.g. GCV), CMVIG or a human herpesvirus vaccine (e.g. a gB vaccine, such as a HCMV gB vaccine).

In some embodiments, the subject is:
a) an individual awaiting a solid organ transplant;
b) a solid organ transplant recipient;
c) a woman of childbearing age;
d) a pregnant woman; and/or
e) a child.

In one embodiment, the subject is an individual awaiting a solid organ transplant.

In one embodiment, the subject is a solid organ transplant recipient.

In one embodiment, the subject is a woman of childbearing age.

In one embodiment, the subject is a pregnant woman.

In one embodiment, the subject is a child. Suitably, a child may be an individual between 12 months and 15 years of age.

Variants, Homologues and Fragments

In addition to the specific proteins and nucleotides mentioned herein, the invention also encompasses the use of variants, derivatives, analogues, homologues and fragments thereof.

In the context of the invention, a variant of any given sequence is a sequence in which the specific sequence of residues (whether amino acid or nucleic acid residues) has been modified in such a manner that the polypeptide or polynucleotide in question substantially retains its function. A variant sequence can be obtained by addition, deletion, substitution, modification, replacement and/or variation of at least one residue present in the naturally-occurring protein.

The term "derivative" as used herein, in relation to proteins or polypeptides of the invention includes any substitution of, variation of, modification of, replacement of, deletion of and/or addition of one (or more) amino acid residues from or to the sequence providing that the resultant protein or polypeptide substantially retains at least one of its endogenous functions.

The term "analogue" as used herein, in relation to polypeptides or polynucleotides includes any mimetic, that is, a chemical compound that possesses at least one of the endogenous functions of the polypeptides or polynucleotides which it mimics.

Typically, amino acid substitutions may be made, for example from 1, 2 or 3 to 10 or 20 substitutions provided that the modified sequence substantially retains the required activity or ability. Amino acid substitutions may include the use of non-naturally occurring analogues.

Proteins used in the invention may also have deletions, insertions or substitutions of amino acid residues which produce a silent change and result in a functionally equivalent protein. Deliberate amino acid substitutions may be made on the basis of similarity in polarity, charge, solubility, hydrophobicity, hydrophilicity and/or the amphipathic nature of the residues as long as the endogenous function is retained. For example, negatively charged amino acids include aspartic acid and glutamic acid; positively charged amino acids include lysine and arginine; and amino acids with uncharged polar head groups having similar hydrophilicity values include asparagine, glutamine, serine, threonine and tyrosine.

The term "homologue" as used herein means an entity having a certain homology with the wild type amino acid sequence and the wild type nucleotide sequence. The term "homology" can be equated with "identity".

A homologous sequence may include an amino acid sequence which may be at least 50%, 55%, 60%, 65%, 70%, 75%, 80%, 85% or 90% identical, preferably at least 95% or 97% or 99% identical to the subject sequence. Typically, the homologues will comprise the same active sites etc. as the subject amino acid sequence. Although homology can also be considered in terms of similarity (i.e. amino acid residues having similar chemical properties/functions), in the context of the invention it is preferred to express homology in terms of sequence identity.

A homologous sequence may include a nucleotide sequence which may be at least 50%, 55%, 60%, 65%, 70%, 75%, 80%, 85% or 90% identical, preferably at least 95% or 97% or 99% identical to the subject sequence. Although homology can also be considered in terms of similarity, in the context of the invention it is preferred to express homology in terms of sequence identity.

Preferably, reference to a sequence which has a percent identity to any one of the SEQ ID NOs detailed herein refers to a sequence which has the stated percent identity over the entire length of the SEQ ID NO referred to.

Homology comparisons can be conducted by eye or, more usually, with the aid of readily available sequence comparison programs. These commercially available computer programs can calculate percentage homology or identity between two or more sequences.

Percentage homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion in the nucleotide sequence may cause the following codons to be put out of alignment, thus potentially resulting in a large reduction in percent homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible, reflecting higher relatedness between the two compared sequences, will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum percentage homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al. (1984) Nucleic Acids Res. 12:387). Examples of other software that can perform sequence comparisons include, but are not limited to, the BLAST package (see Ausubel et al. (1999) ibid-Ch. 18), FASTA (Atschul et al. (1990) J. Mol. Biol. 403-410) and the GENEWORKS suite of comparison tools. Both BLAST and FASTA are available for offline and online searching (see Ausubel et al. (1999) ibid, pages 7-58 to 7-60). However, for some applications, it is preferred to use the GCG Bestfit program. Another tool, called BLAST 2 Sequences is also available for comparing protein and nucleotide sequences (see FEMS Microbiol. Lett. (1999) 174:247-50; FEMS Microbiol. Lett. (1999) 177:187-8).

Although the final percent homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see the user manual for further details). For some applications, it is preferred to use the public default values for the GCG package, or in the case of other software, the default matrix, such as BLOSUM62.

Once the software has produced an optimal alignment, it is possible to calculate percent homology, preferably percent sequence identity. The software typically does this as part of the sequence comparison and generates a numerical result.

"Fragments" are also variants and the term typically refers to a selected region of the polypeptide or polynucleotide that is of interest either functionally or, for example, in an assay. "Fragment" thus refers to an amino acid or nucleic acid sequence that is a portion of a full-length polypeptide or polynucleotide.

Such variants may be prepared using standard recombinant DNA techniques such as site-directed mutagenesis. Where insertions are to be made, synthetic DNA encoding the insertion together with 5' and 3' flanking regions corresponding to the naturally-occurring sequence either side of the insertion site may be made. The flanking regions will contain convenient restriction sites corresponding to sites in the naturally-occurring sequence so that the sequence may be cut with the appropriate enzyme(s) and the synthetic DNA ligated into the cut. The DNA is then expressed in accordance with the invention to make the encoded protein. These methods are only illustrative of the numerous standard techniques known in the art for manipulation of DNA sequences and other known techniques may also be used.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The publications discussed herein are provided solely for their disclosure prior to the filing date of the present application. Nothing herein is to be construed as an admission that such publications constitute prior art to the claims appended hereto.

The invention will now be further described by way of Examples, which are meant to serve to assist one of ordinary skill in the art in carrying out the invention and are not intended in any way to limit the scope of the invention.

EXAMPLES

Example 1

A phase II randomized controlled trial of a human cytomegalovirus (HCMV) vaccine was performed in patients awaiting a solid organ transplant. The vaccine comprised of a recombinant form of the viral protein glycoprotein B (gB) delivered with MF59 adjuvant. Volunteers were vaccinated with gB/MF59 or placebo control prior to transplant and monitored for humoral immunity to gB and, post-transplant, the development of HCMV viraemia. It was demonstrated that the partial protection observed directly correlated with the levels of anti-gB antibody response elicited in response to vaccination (Griffiths et al, 2011, Lancet, 377:1256-63).

We performed an analysis in seronegative individuals of humoral responses against known antigenic domains of gB (AD-1 to AD-5), which revealed no relationship with vaccine-mediated protection suggesting that a novel response was being induced by vaccination that could be important for protection.

Figure 2:
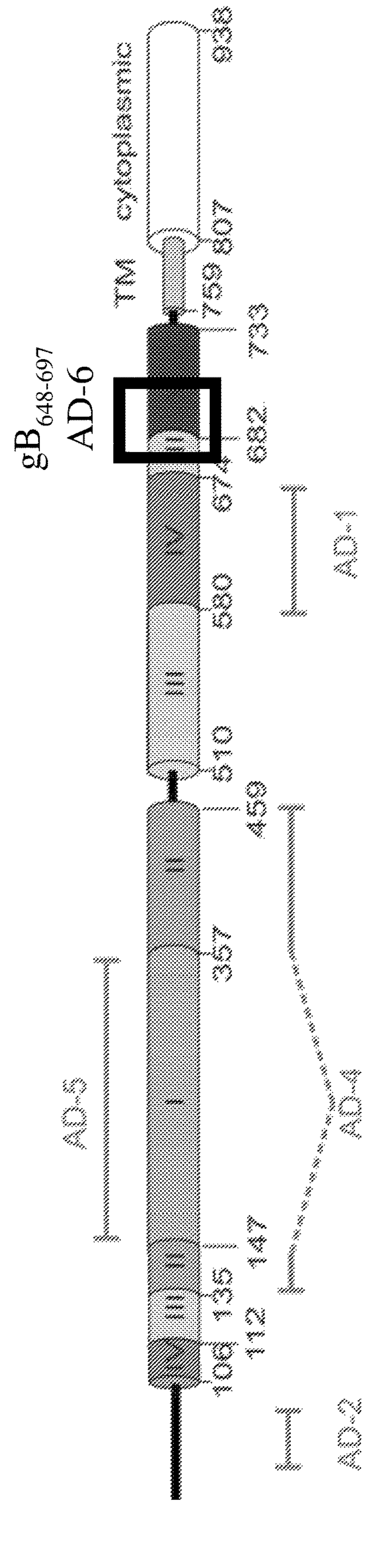
FIG. 2: Diagram of gB protein structure
Figure 3:
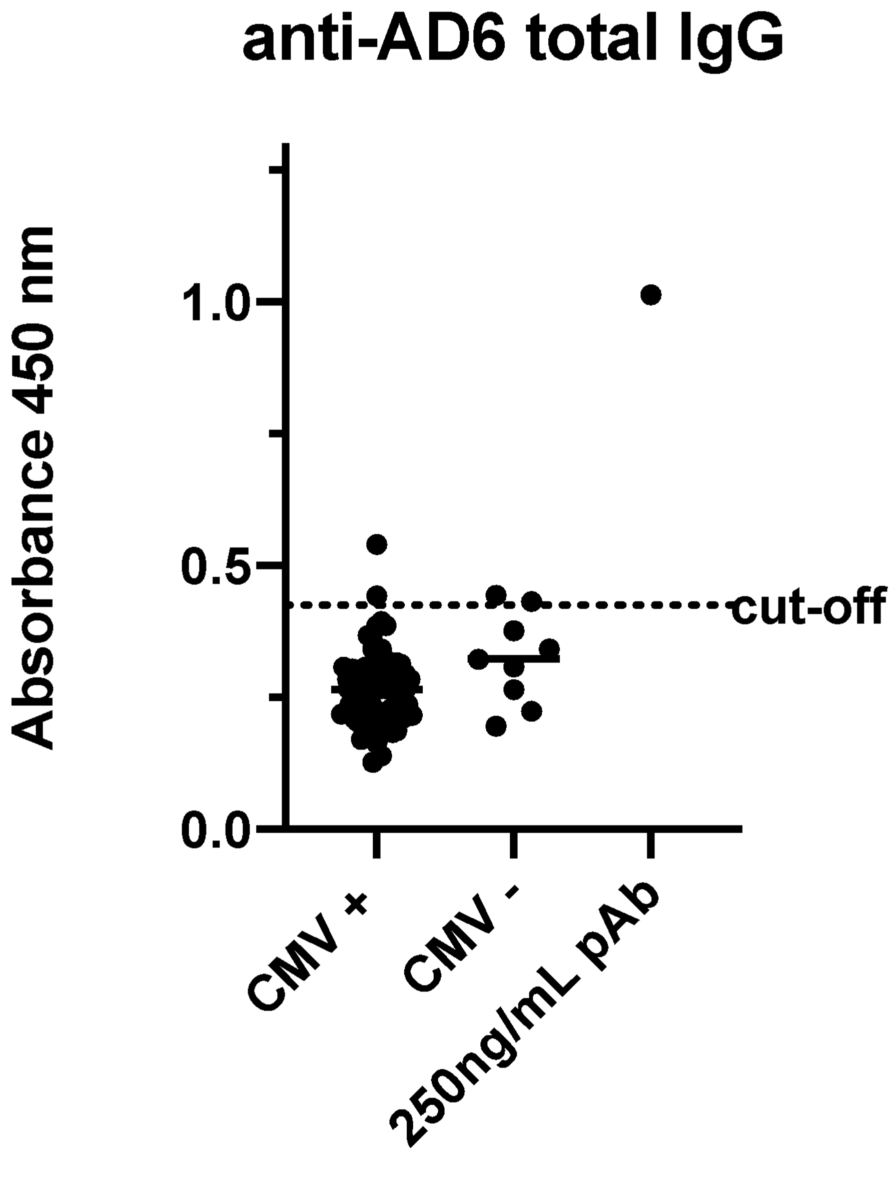
FIG. 3: Anti-AD6 antibody responses are rarely detected in naturally infected individuals

To test this, sera taken from the seronegative cohort vaccinated with gB/MF59 was analysed by gB peptide microarray (JPT Technologies). Overlapping peptides 15 amino acids in length that covered the entirety of the gB protein were used to identify novel antibody responses against linear epitopes in gB. Using this approach, strong anti-gB responses were detected in the region between amino acids 648-697 of gB (FIG. 1). These responses are against a region we are defining as AD6 (FIG. 2) and were detectable in >50% of vaccinated individuals. In contrast, this response is rarely seen in individuals naturally infected with HCMV (<5%: FIG. 3).

Figure 4:
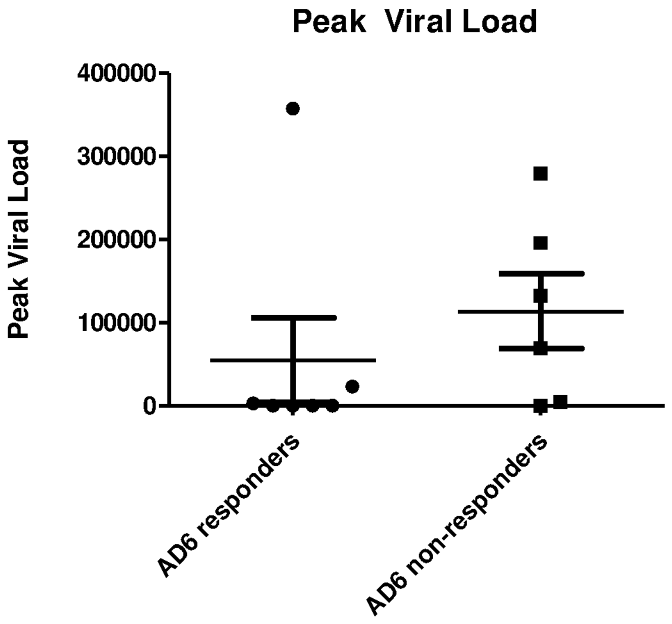
FIG. 4: Vaccinated individuals with an AD6 response have better outcomes post-transplant
Figure 4:
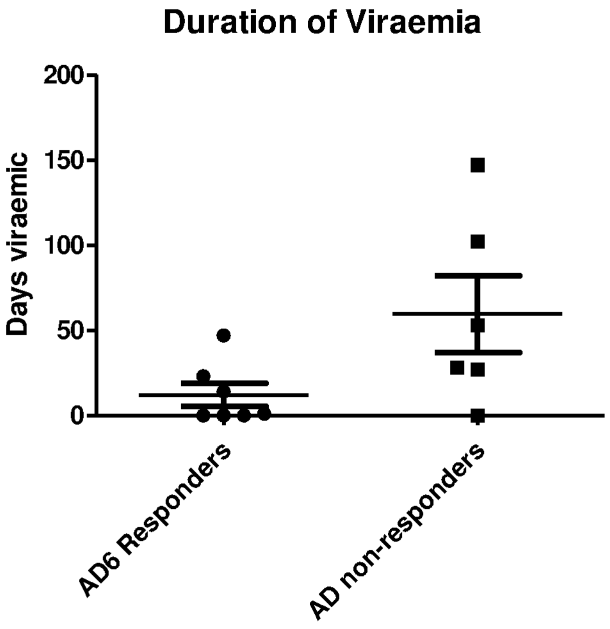

We have previously reported that antibody responses against AD1-5 do not correlate with protection in HCMV seronegative patients vaccinated with gB/MF59 (Baraniak et al, PNAS, 2018). Thus, we asked whether responses against AD6 correlated with outcome post transplant. The data show (FIG. 4) individuals with good antibody responses against AD6 post vaccination had lower peak viral loads and shorter duration of viraemia post-transplant. These data represent the first direct correlation between an epitope-specific antibody response against the gB vaccine and better outcomes post-transplant in seronegative vaccine recipients.

Example 2

Figure 5:
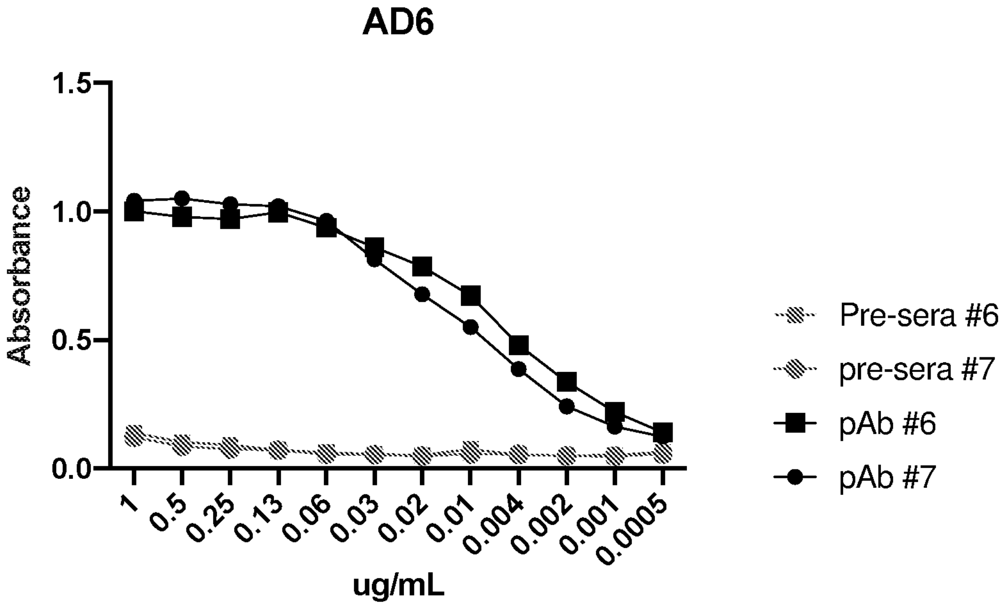
FIG. 5: Generation of an anti-AD6 antibody in rabbits
Figure 5:
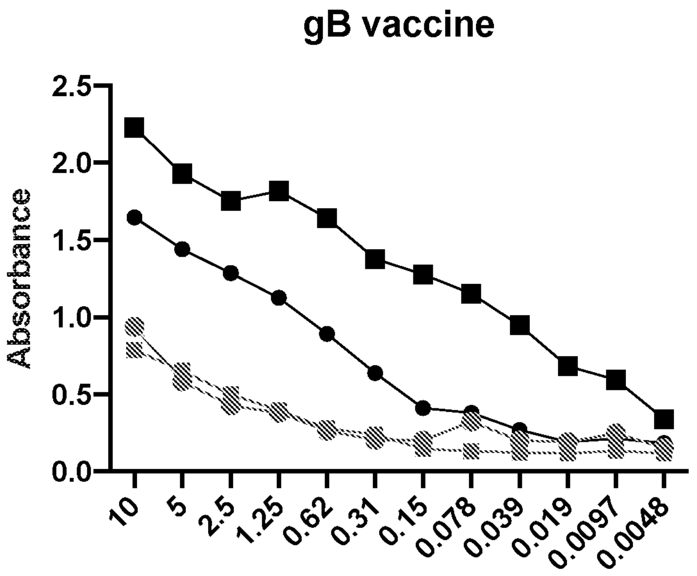
Figure 6:
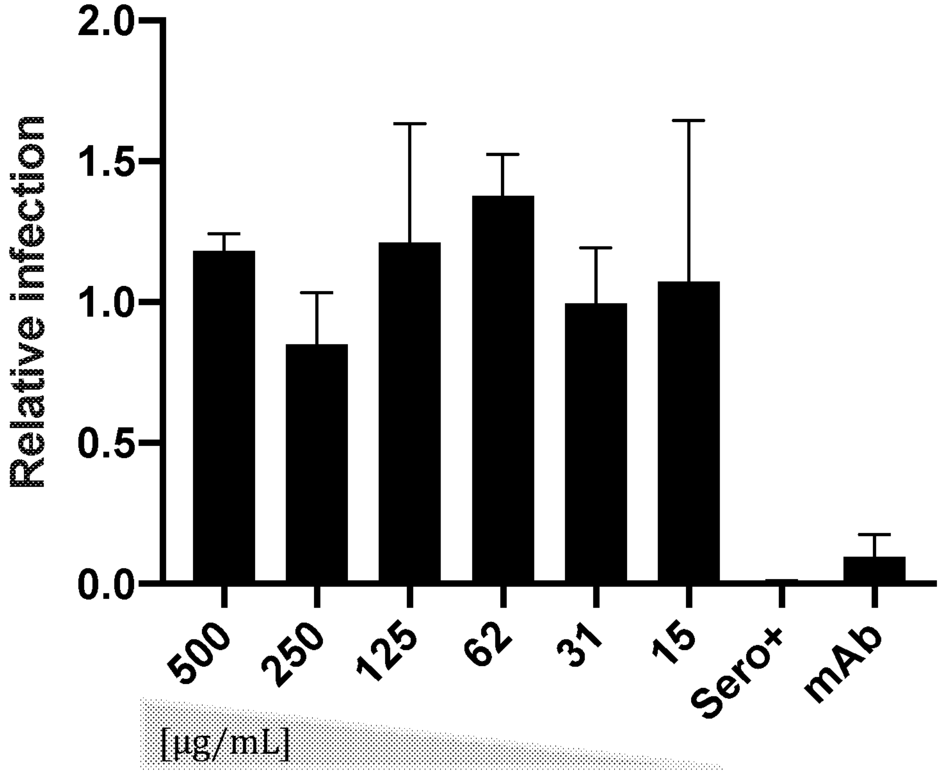
FIG. 6: Anti-AD6 antibody does not neutralize CMV infection of fibroblasts
Figure 7:
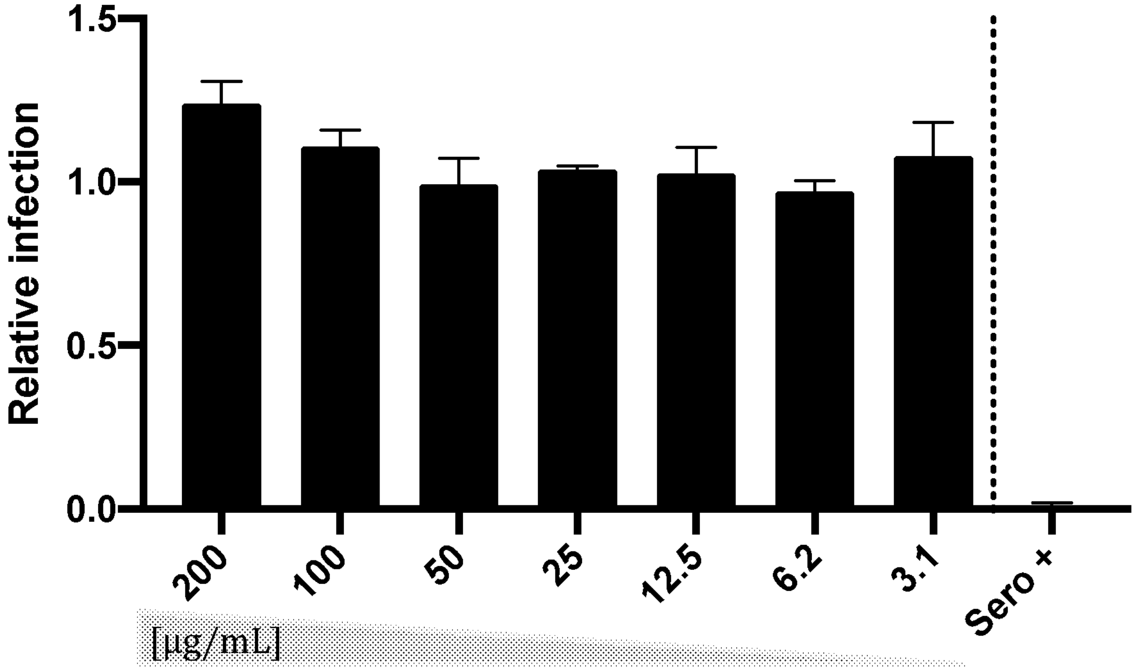
FIG. 7: Anti-AD6 antibody does not neutralize CMV infection of epithelial cells

To investigate anti-AD6 antibodies in more detail, rabbits were immunized with the AD6 peptide (SEQ ID NO: 7) to generate polyclonal sera. These sera were confirmed to recognize the AD6 peptide and also the gB vaccine protein by ELISA (FIG. 5). Having established that the sera recognizes AD6 and recombinant gB we tested whether the antibody could neutralize HCMV infection. HCMV was incubated with the antibody for 1 hour prior to the infection of cells and then infection scored by staining cells for viral gene expression—a marker of infection. The data show that the rabbit AD6 antisera does not block HCMV infection of multiple cell types including fibroblasts (FIG. 6) and epithelial cells (FIG. 7). Thus, the anti-AD6 antibodies are not neutralising antibodies.

The lack of neutralizing activity observed with an AD6 antisera is consistent with our previous report that demonstrated that vaccination with gB/MF59 did not elicit potent neutralizing antibody responses against gB (Baraniak et al, PNAS, 2018).

Figure 8:
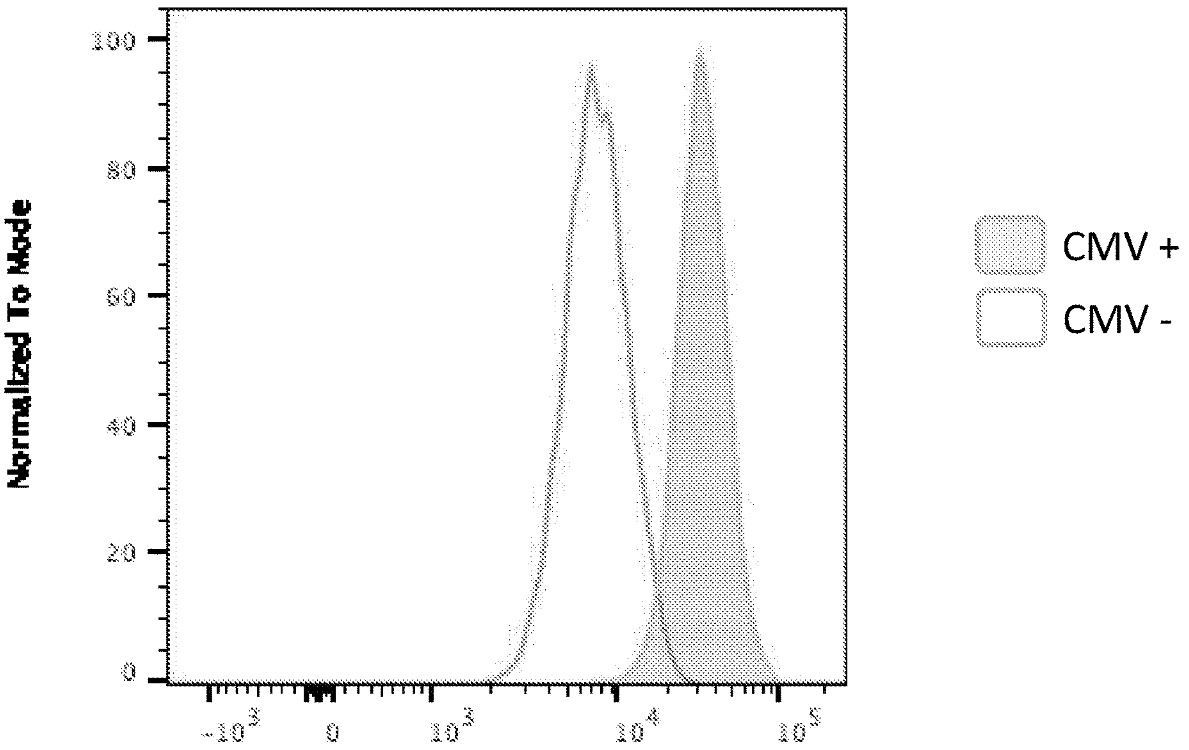
FIG. 8: AD6 polyclonal sera (pAb) recognizes CMV infected cells

HCMV can be targeted by antibodies in two ways: via direct antibody binding to the virus (classic neutralization as measured in FIGS. 6 & 7) or via the targeting of infected cells. The gB protein is expressed on the surface of virally infected cells. Furthermore, the expression of gB on the surface of cells can be detected using the AD6 antibody. Infected cells were fixed 5 days post infection with HCMV and incubated with rabbit anti-AD6 sera and analysed by flow cytometry. Cells were infected with a strain of HCMV expressing green fluorescent protein (GFP) allowing the identification of infected (CMV+) and uninfected cells (CMV−) cells. The data show that AD6 antisera detects gB on the surface of infected cells (FIG. 8).

To test whether this had any impact on HCMV replication we utilized a strain of HCMV engineered to represent the wild type sequence (NCBI Reference Sequence: NC_006273.2) to grow predominantly as a cell associated virus in viral spreading assay. Cells were infected at a low multiplicity of infection (MOI) resulting in ~5% infection at day 1. The cells were then cultured for 10 days to allow viral replication and spread into neighbouring cells which was enumerated using Hermes WiScan technology to establish a percentage infection in the assay.

Figure 9:
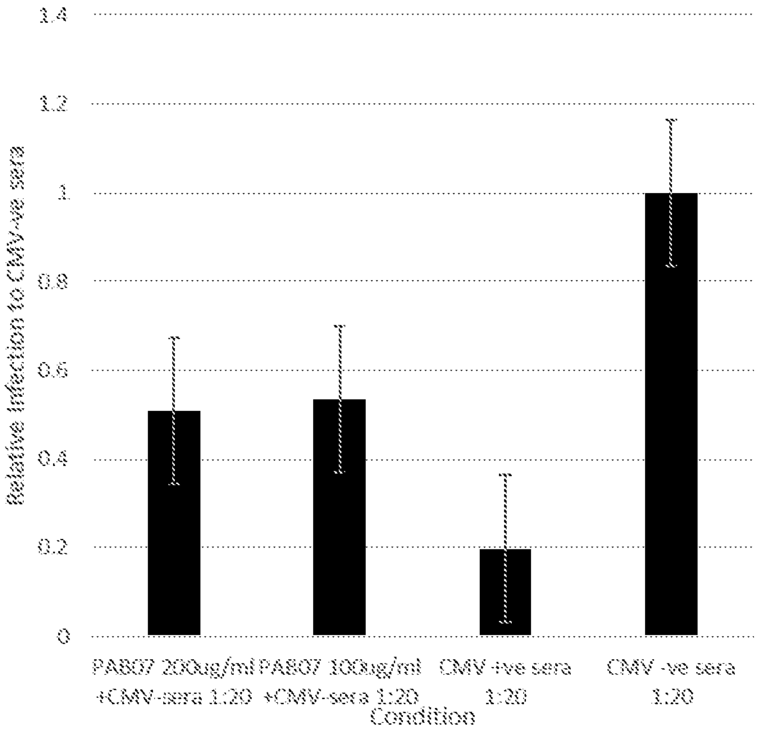
FIG. 9: Spread of HCMV is reduced in the presence of the AD6 antisera

Two days post HCMV infection, cells were further incubated with rabbit anti-AD6 sera, CMV positive donor serum or CMV negative donor serum. Rate of spread of the virus in each condition was calculated relative to the CMV negative donor serum control (no CMV specific activity). Inhibition of viral spread was calculated by enumerating % infection in test wells and comparing with control conditions. A reduction in viral spread of >20% was considered functional. The data show that the spread of HCMV is reduced in the presence of the AD6 antisera compared to the serum control (FIG. 9) evidenced by a reduced percentage of infected cells at 10 days culture. Thus, the anti-AD6 sera limits the spread of HCMV in vitro.

Figure 10:
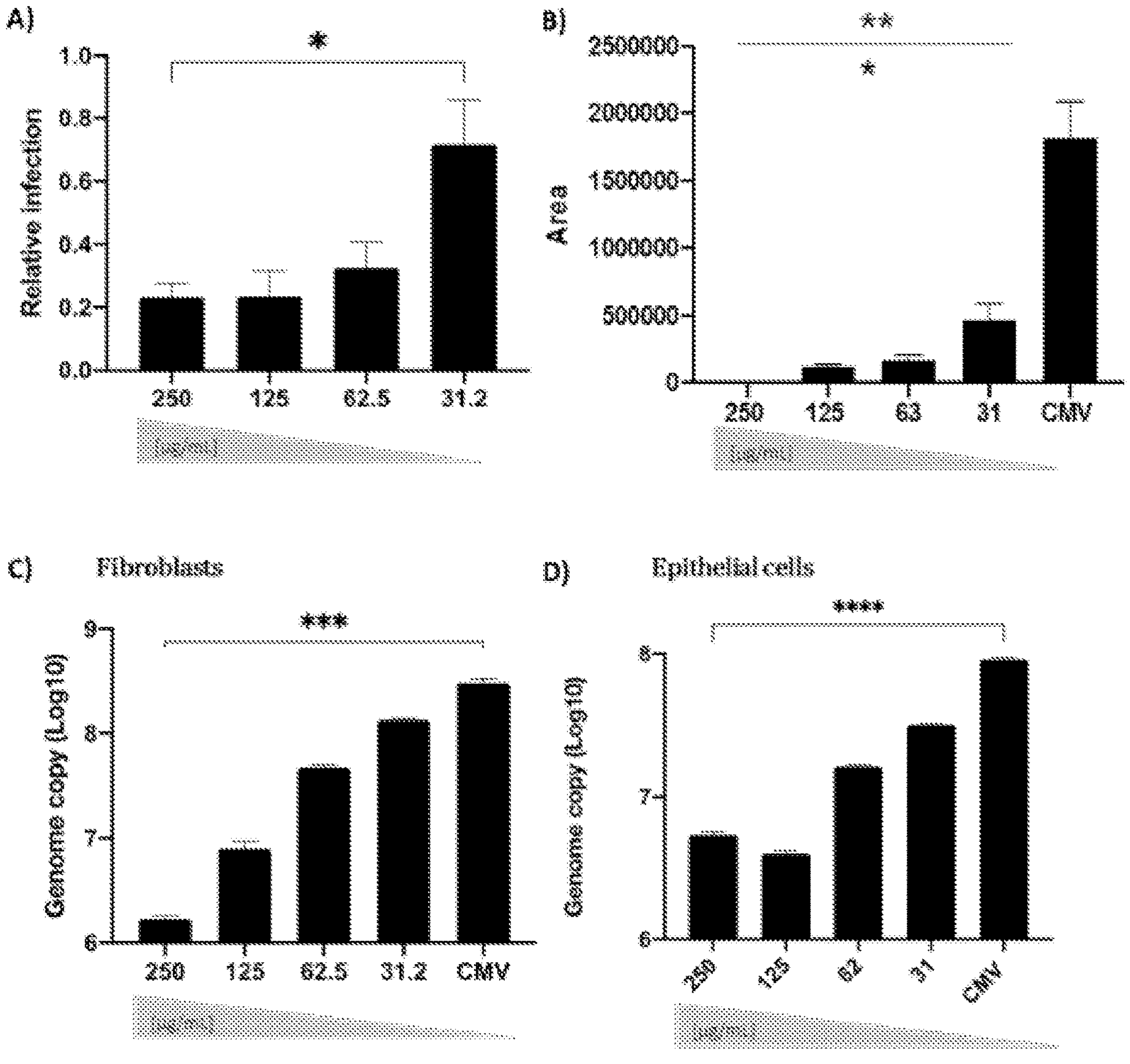
FIG. 10: Anti-AD6 antisera limits cell associated spread of CMV. To measure spread of cell associated virus in HFFs, cells were infected with HCMV (MOI=0.01). At 1 dpi and 5 dpi, anti-AD6 antibody was added at the indicated concentrations and then 10 dpi, cells were then analysed by IF or DNA-qPCR for viral spread. Percentage of infected cells (A) was measured by anti-IE stain counterstained with nuclei stain and counted by automated fluorescence microscopy (n=3) and the area of plaques was measured using Fiji software (B). Alternatively, total DNA was harvested, and CMV genome copies per $10^6$ cells assessed by qPCR (C; n=2). ARPE-19 epithelial cells were infected with pentamer positive HCMV (MOI=0.01), and total DNA harvested 20 dpi and analysed for viral genome copy number per $10^6$ cells (D). P values were calculated by a Kruskal-Wallis test with Dunn's multiple-comparison test where appropriate. **, $P<0.0001$; *, $P<0.001$; *, $P<0.01$; ns (nonsignificant), $P>0.05$. The error bars represent 1 standard deviation from the mean.

To further demonstrate that the rabbit anti-AD6 antibody blocks the spread of HCMV in vitro, we measured anti-viral control in multiple ways thereby providing a more comprehensive analysis of multiple parameters in two cell types (fibroblasts and epithelial cells). The data evidence that the anti-AD6 sera limits the spread of HCMV in vitro in both fibroblasts and epithelial cells (FIG. 10).

Figure 11:
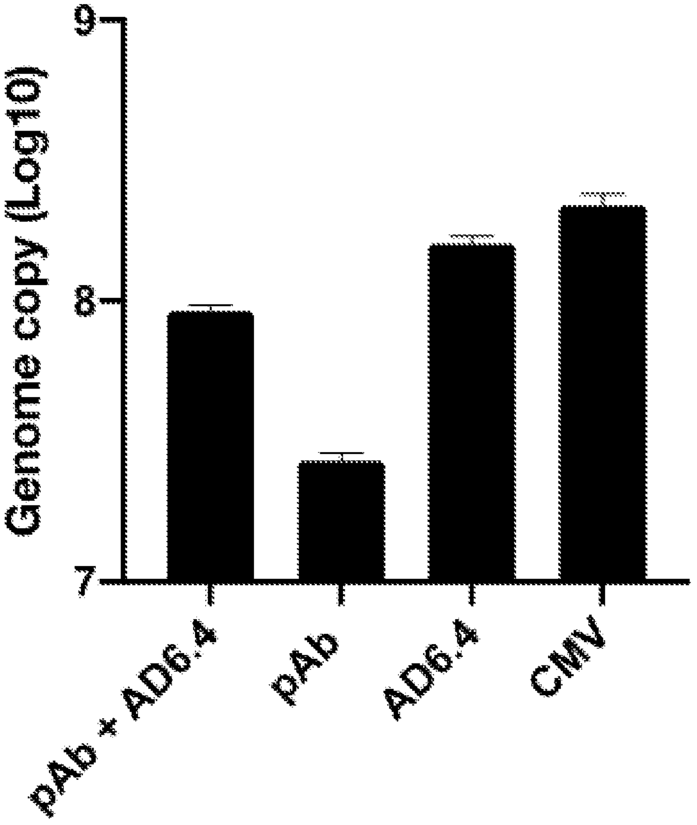
FIG. 11: A peptide within AD6 partially inhibits the activity of a polyclonal AD6 antisera against HCMV. HFFs were infected with HCMV (MOI=0.01). Then, at 1 d.p.i. and at 5 d.p.i, were incubated with anti-AD6 antibody (pAb), anti-AD6 antibody preabsorbed with AD6.4 peptide (pAb+AD6.4) or just peptide (AD6.4). The AD6.4 peptide spanned the N region of AD6 ($gB_{(661-676)}$) and was used at a 10× molar excess prior to addition to infected cells 1 d.p.i and at 5 d.p.i. Then, at 10 d.p.i. total DNA was harvested, and CMV genome copies per $10^6$ cells assessed by qPCR (n=2). The error bars represent standard error of the mean.

To further investigate the identified hotspots, a synthesised 15mer peptide that covers the ELYSQKELRSS peptide (denoted as AD6.4) (SEQ ID NO: 25) was pre-absorbed with anti-Ad6 antibody and the activity of the antisera tested. The data shows partial reversal of the activity of the rabbit polyclonal antisera suggesting that antibodies directed against this region are an important component of the control (FIG. 11).

To further investigate the role of AD6 in the control of HCMV infection, we assessed the capacity of sera and sera preabsorbed with AD6 peptide to limit viral spread using human sera from HCMV seronegative individuals who received placebo or two doses of gB/MF59 vaccine. The data in FIG. 12 show the following:

A) Sera from placebo controls have no effect on spread of HCMV in vitro (this is expected as they have no HCMV specific antibodies); and B,C) The sera from some gB/MF59 vaccine recipients can reduce the spread of HCMV in vitro and that for some patients this is blocked by preabsorbtion with AD6 protein e.g. 002-0040, 004-022, 004-024.

Figure 12:
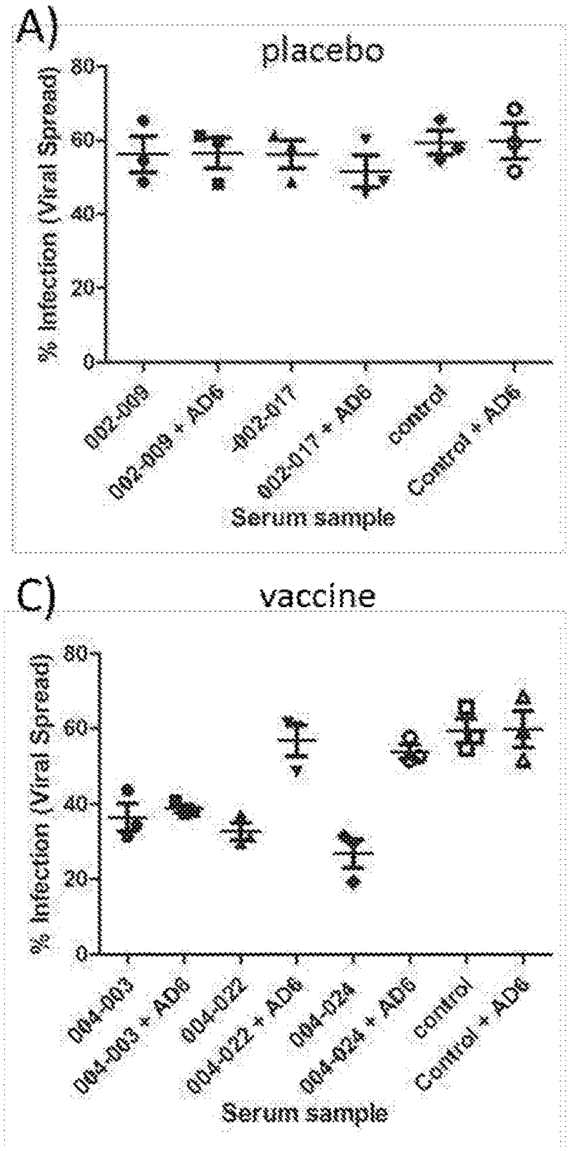
FIG. 12: Vaccine sera from patients with AD6 responses reduces viral spread and this is reversed by AD6 in some individuals. HFFs were infected with HCMV (MOI=0.01). Then, at 1 d.p.i. and at 5 d.p.i, we incubated with human sera from HCMV seronegative individuals who received placebo (A) or two doses of gB/MF59 vaccine (B,C). The capacity of sera and sera preabsorbed with AD6 peptide to limit viral spread was assessed at 10 d.p.i. when cells were analysed by IF to measure spread of the virus. Control represents spread of HCMV without the addition of sera.

Overall, the data show that complete AD6 peptide (SEQ ID NO: 7) reverses the activity of human vaccine sera and its capacity to block cell spread (FIG. 12). Thus, these data provide evidence that human AD6 antibodies are active against HCMV.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. An immunogenic composition comprising a human herpesvirus immunogenic peptide comprising SEQ ID NO: 7, SEQ ID NO: 9 or SEQ ID NO: 11, or a sequence having at least 90% identity thereto, wherein the human herpesvirus immunogenic peptide is about 50 or fewer amino acids in length;

and wherein the composition does not comprise other antigenic domains of glycoprotein B (gB).

2. An immunogenic composition comprising a human herpesvirus immunogenic peptide, wherein the immunogenic peptide consists of SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 or SEQ ID NO: 26.

3. The immunogenic composition according to claim 2, wherein the immunogenic peptide consists of SEQ ID NO: 25 or SEQ ID NO: 26.

4. The immunogenic composition according to claim 1, wherein the human herpesvirus is human cytomegalovirus (HCMV), herpes simplex virus-1 (HSV-1), or Epstein-Barr virus (EBV).

5. The immunogenic composition according to claim 4, wherein the human herpesvirus is HCMV.

6. An immunogenic composition comprising a nucleic acid sequence encoding the human herpesvirus immunogenic peptide as defined in claim 1 or a vector comprising said nucleic acid sequence.

7. A vaccine comprising an immunogenic composition as defined in claim 1.

8. A method for the treatment and/or prevention of a human herpesvirus infection, comprising administering: a) an immunological composition or vaccine comprising a human herpesvirus immunogenic peptide as defined in claim 1, to a subject in need thereof.

9. The method according to claim 8, wherein the subject is:

a) an individual awaiting a solid organ transplant;

b) a solid organ transplant recipient;

c) a woman of childbearing age;

d) a pregnant woman; or e) a child.

10. The method according to claim 8, wherein the human herpesvirus is human cytomegalovirus (HCMV), herpes simplex virus-1 (HSV-1), or Epstein-Barr virus (EBV).

11. The method according to claim 10, wherein the human herpesvirus is HCMV.

* * * * *